(12) United States Patent
Longo et al.

(10) Patent No.: US 6,486,322 B1
(45) Date of Patent: Nov. 26, 2002

(54) AZAINDOLE DERIVATIVES, PROCESS FOR THEIR PREPARATION, AND THEIR USE AS ANTITUMOR AGENTS

(75) Inventors: Antonio Longo, Milan (IT); Maria Gabriella Brasca, Cusago (IT); Paolo Orsini, Gallarate (IT); Gabriella Traquandi, Milan (IT); Valeria Pittalà, Catania (IT); Anna Vulpetti, Brugherio (IT); Mario Varasi, Milan (IT); Paolo Pevarello, Pavia (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 09/968,042

(22) Filed: Oct. 2, 2001

Related U.S. Application Data

(62) Division of application No. 09/597,274, filed on Jun. 19, 2000, now Pat. No. 6,335,342.

(51) Int. Cl.⁷ .............................................. C07D 471/04
(52) U.S. Cl. ...................................................... 546/113
(58) Field of Search ......................................... 546/113

(56) References Cited

U.S. PATENT DOCUMENTS

| | | | |
|---|---|---|---|
| 5,663,346 A | 9/1997 | Buzzeti et al. | 546/113 |
| 5,719,135 A | 2/1998 | Buzzeti et al. | 546/113 |
| 5,952,355 A | 9/1999 | Ikeda et al. | 514/339 |
| 5,977,131 A * | 11/1999 | Nagel | 514/300 |
| 6,335,342 B1 | 1/2002 | Longo et al. | 514/253 |

FOREIGN PATENT DOCUMENTS

WO  WO 94/14808  7/1994

* cited by examiner

*Primary Examiner*—Bernard Dentz
(74) *Attorney, Agent, or Firm*—Oblon, Spivak, McClelland, Maier & Neustadt

(57) ABSTRACT

Novel 1H-pyrrolo[2,3-b]pyridines which are represented by formula (I):

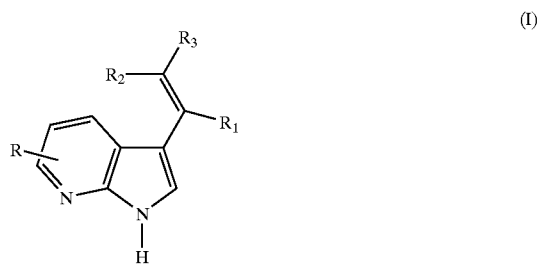

wherein R is a hydrogen or halogen atom or a group selected from —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, or —(CH$_2$)$_n$NHSO$_2$R$_4$, wherein n is either 0 or 1, R$_4$ and R$_5$ are as described in the specification; R$_1$ is hydrogen or an optionally substituted alkyl group; R$_2$ is an optionally substituted group selected from alkyl or aryl; R$_3$ is hydrogen or a group selected from —CONR$_4$R$_5$, —COOR$_4$, —CONHOR$_4$, —SO$_2$NHR$_4$, alkylsulphonylaminocarbonyl or perfluorinated alkylsulphonylaminocarbonyl; or a pharmaceutically acceptable salt thereof, are disclosed.

These compounds are useful for treating cell proliferative disorders associated with an altered cell dependent kinase activity.

19 Claims, No Drawings

AZAINDOLE DERIVATIVES, PROCESS FOR THEIR PREPARATION, AND THEIR USE AS ANTITUMOR AGENTS

This application is a Divisional application of U.S. application Ser. No. 09/597,274 now U.S. Pat. No. 6,335,342 B1 filed Jun. 19, 2000.

The present invention relates to azaindole derivatives and, more in particular, to 1H-pyrrolo[2,3-b]pyridine derivatives, to a process for their preparation, to pharmaceutical compositions comprising them and to their use as therapeutic agents, particularly in the treatment of cancer and cell proliferative disorders.

Several cytotoxic drugs such as, e.g. fluorouracil (5-FU), doxorubicin and camptothecins result to damage DNA or to affect cellular metabolic pathways and thus cause, in many cases, an indirect block of the cell cycle.

Therefore, by producing an irreversible damage to both normal and tumor cells, these agents result in a significant toxicity and side-effects.

In this respect, compounds capable of being highly specific antitumor agents by selectively leading to tumor cell arrest and apoptosis, with comparable efficacy but reduced toxicity than the currently available drugs, are desirable.

It is well known in the art that progression through the cell cycle is governed by a series of checkpoint controls, otherwise referred to as restriction points, which are regulated by a family of enzymes known as the cyclin-dependent kinases (cdk).

In their turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of metaphases.

For a general reference to cyclins and cyclin-dependent kinases see, for instance, Kevin R. Webster et al. in Exp. Opin. Invest. Drugs, 1998, Vol. 7(6), 865–887.

Checkpoint controls are defective in tumor cells due, in part, to disregulation of cdk activity. For example, altered expression of cyclin E and cdk's has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

It has now been found that the 1H-pyrrolo{2,3-b]pyridine derivatives of the invention are endowed with cdk/cyclin kinase inhibitory activity and are thus useful in therapy as antitumor agents whilst lacking, in terms of both toxicity and side effects, the aforementioned drawbacks known for currently available antitumor drugs.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of yeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation, these azaindoles are also useful in the treatment of a variety of cell proliferative disorders such as, for instance, benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be useful in the treatment of Alzheimer's disease, as suggested by the fact that cdk5 is involved in the phosphorylation of tau protein (*J. Biochem.*, 117, 741–749, 1995; *FEBS Lett.*, 459, 421–426, 1999).

The compounds of this invention, as modulators of apoptosis, could be useful in the treatment of cancer, viral infections, prevention of AIDS development in HIV-infected individuals, autoimmune diseases and neurodegenerative disorder.

The compounds of this invention could be useful in inhibiting tumor angiogenesis and metastasis.

The compounds of this invention may also act as inhibitors of other protein kinases, e.g. protein kinase C, her2, raf1, MEK1, MAP kinase, EGF receptor, VEGF receptor, PDGF receptor, IGF receptor, PI3 kinase, weel kinase, Src, Abl and thus be effective in the treatment of diseases associated with other protein kinases.

The compounds of the invention are also useful in the treatment and/or prevention of chemotherapy-induced or radiotherapy-induced alopecia.

Several 1H-pyrrolo[2,3-b]pyridines are known in the art as therapeutic agents. Among them are some cyanoacrylamido derivatives active as tyrosine kinase inhibitors as reported in WO 96/00226, in the name of the applicant. Some other acrylamido-1H-pyrrolo[2,3-b]pyridines are disclosed as antiallergic agents, as reported in Chem. Pharm. Bull., 37(3), 684–7 (1989).

Accordingly, the present invention provides a method for treating cell proliferative disorders associated with an altered cell dependent kinase activity, by administering to a mammal in need thereof an effective amount of a 1H-pyrrolo[2,3-b]pyridine represented by formula (I):

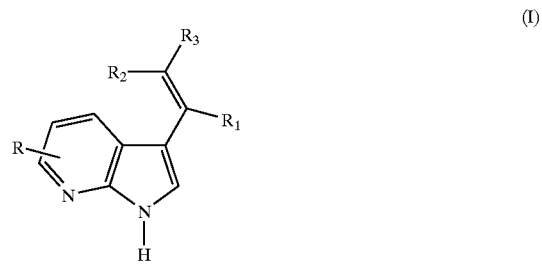

wherein

R is a hydrogen or halogen atom or a group selected from —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, or —(CH$_2$)$_n$NHSO$_2$R$_4$, wherein n is either 0 or 1, R$_4$ and R$_5$ are, independently from each other, hydrogen or an optionally substituted group selected from alkyl, alkenyl, alkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, aryl, arylalkyl, arylalkenyl, arylalkynyl or, taken together to the nitrogen atom to which they are bonded, form an optionally substituted heterocyclyl group such as pyrrolidine, piperidine, piperazine and morpholine;

R$_1$ is hydrogen or an optionally substituted alkyl group;

R$_2$ is an optionally substituted group selected from alkyl or aryl;

R$_3$ is hydrogen or a group selected from —CONR$_4$R$_5$, —COOR$_4$, —CONHOR$_4$, —SO$_2$NHR$_4$, alkylsulphonylaminocarbonyl or perfluorinated alkylsulphonylaminocarbonyl; wherein R$_4$ and R$_5$ have the above reported meanings;

or a pharmaceutically acceptable salt thereof.

In a preferred embodiment of the method described above, the cell proliferative disorder is selected from the group consisting of cancer, Alzheimer's disease, viral infections, auto-immune diseases and neurodegenerative disorders.

Specific types of cancer that may be treated include carcinoma, hematopoietic tumors of lymphoid lineage, hematopoietic tumors of myeloid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

In another preferred embodiment of the method described above, the cell proliferative disorder is selected from benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, the inventive method provides tumor angiogenesis and metastasis inhibition.

The compounds of this invention may also act as inhibitors of other protein kinases, e.g. protein kinase C, her2, raf1, MEK1, MAP kinase, EGF receptor, VEGF receptor, PDGF receptor, IGF receptor, PI3 kinase, wee1 kinase, Src, Abl and thus be effective in the treatment of diseases associated with other protein kinases.

The present invention further provides a compound which is a 1H-pyrrolo{2,3-b]pyridine derivative represented by formula (I):

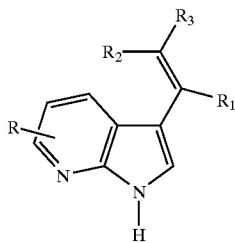

(I)

wherein

R is a hydrogen or halogen atom or a group selected from —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, or —(CH$_2$)$_n$NHSO$_2$R$_4$, wherein n is either 0 or 1, R$_4$ and R$_5$ are, independently from each other, hydrogen or an optionally substituted group selected from alkyl, alkenyl, alkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, aryl, arylalkyl, arylalkenyl, arylalkynyl or, taken together to the nitrogen atom to which they are bonded, form an optionally substituted heterocyclyl group such as pyrrolidine, piperidine, piperazine and morpholine;

R$_1$ is hydrogen or an optionally substituted alkyl group;

R$_2$ is an optionally substituted group selected from alkyl or aryl;

R$_3$ is hydrogen or a group selected from —CONR$_4$R$_5$, —COOR$_4$, —CONHOR$_4$, —SO$_2$NHR$_4$, alkylsulphonylaminocarbonyl or perfluorinated alkylsulphonylaminocarbonyl; wherein R$_4$ and R$_5$ have the above reported meanings;

or a pharmaceutically acceptable salt thereof.

In the present description, unless otherwise specified, with the term halogen atom we intend a fluorine, chlorine, bromine or iodine atom.

As used herein and unless otherwise indicated, alkyl stands for straight or branched lower $C_1$–$C_6$ alkyl groups such as, for instance, methyl, ethyl, n-propyl, isopropyl, n-butyl, isobutyl, sec-butyl, t-butyl, n-pentyl, n-hexyl, and the like.

Unless otherwise specified, the terms alkenyl and alkynyl refer to a straight or branched hydrocarbon chain radical with from 2 to 6 carbon atoms and at least one carbon to carbon double or triple bond, respectively.

Unless otherwise specified, with the term cycloalkyl we intend a $C_3$–$C_6$ cycloalkyl group such as, for instance, cyclopropyl, cyclobutyl, cyclopentyl and cyclohexyl as well as a bridged cycloalkyl group with from 6 to 10 carbon atoms such as adamantane.

The term aryl stands for mono-, bi- or poly-carbocyclic or heterocyclic hydrocarbons with from 1 to 4 ring moieties, either fused or linked to each other by single bonds, wherein at least one of the rings is aromatic.

The term heterocycle, hence encompassing heteroaromatic rings also referred to as aryl, relates to a 5 or 6 membered saturated or unsaturated carbocycle wherein one or more carbon atoms are replaced by one or more atoms selected from nitrogen, oxygen and sulphur.

Example of preferred aryl groups are, for instance, phenyl, 1-naphtyl, 2-naphthyl, indanyl, indenyl, biphenyl, benzocycloalkyl, e.g. bicyclo[4.2.0]octa-1,3,5,-triene, benzodioxolyl, as well as optionally benzocondensed pyrrolyl, furyl, thienyl, imidazolyl, pyrazolyl, thiazolyl, oxazolyl, isoxazolyl, pyridyl, pyrazinyl, pyrimidyl, tetrazolyl, thiadiazolyl, oxadiazolyl, triazolyl, pyridazinyl and the like.

As noted above, each of the R$_1$, R$_2$, R$_4$ and R$_5$ groups may be further substituted in any of the free positions by one or more groups, for instance 1 to 6 groups, selected from: halogen, nitro, oxo groups (═O), carboxy, cyano, alkyl, perfluorinated alkyl, perfluorinated alkoxy, alkenyl, alkynyl, cycloalkyl, aryl, heterocyclyl; amino groups and derivatives thereof such as, for instance, alkylamino, alkoxycarbonylalkylamino, dialkylamino, arylamino, diarylamino, ureido, alkylureido or arylureido; carbonylamino groups and derivatives thereof such as, for instance, hydrogenocarbonylamino (HCONH—), alkylcarbonylamino, alkenylcarbonylamino, arylcarbonylamino, alkoxycarbonylamino, aryloxycarbonylamino; oxygen-substituted oximes such as, for instance, alkoxycarbonylalkoxyimino or alkoxyimino; hydroxy groups and derivatives thereof such as, for instance, alkoxy, aryloxy, alkylcarbonyloxy, arylcarbonyloxy, alkylaminocarbonyloxy, arylaminocarbonyloxy, cycloalkyloxy, cycloalkenyloxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; arylaminocarbonyl, sulfurated derivatives such as, for instance, alkylthio, arylthio, alkylsulphonyl, arylsulphonyl, alkylsulfamoyl, arylsulfamoyl, alkylsulphinyl, arylsulphinyl, arylsulphonyloxy, aminosulfonyl, alkylaminosulphonyl, dialkylaminosulphonyl or arylaminosulphonyl.

In their turn, whenever appropriate, each of the above possible substituents may be further substituted by one or more of the aforementioned groups. Compounds of formula (I) wherein the given $R_1$, $R_2$, $R_4$ and $R_5$ groups are substituted by one or more of the aforementioned substituents which, in turn, are optionally further substituted as set forth above, are given below.

Just as an example, the compound 3-(6-{[(3-hydroxyphenyl)acetyl]amino}-1H-pyrrolo[2,3-b]pyridin-3-yl)-2-phenyl-2-propenamide is represented by formula (I) wherein $R_1$ is hydrogen; $R_2$ is aryl (e.g. phenyl); $R_3$ is $CONR_4R_5$ wherein both $R_4$ and $R_5$ are hydrogen atoms (e.g. $CONH_2$); R is —$(CH_2)_n NHCOR_4$ wherein n is 0 and $R_4$ is an alkyl group (e.g. methyl) wherein the alkyl is further substituted by aryl (e.g. phenyl) which, in turn, is substituted by hydroxy.

With the term perfluorinated alkyl and alkoxy group we intend a $C_1$–$C_6$ alkyl or alkoxy group further substituted by more than one fluorine atom such as, for instance, trifluoromethyl, 2,2,2-trifluoroethyl, 1,1,2,2,2-pentafluoroethyl, trifluoromethoxy and the like.

Pharmaceutically acceptable salts of the compounds of formula (I) are the acid addition salts with inorganic or organic, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

The compounds of formula (I) may have asymmetric carbon atoms and may therefore exist either as racemic admixtures or as individual optical isomers.

Accordingly, the use as an antitumor agent of all the possible isomers and their admixtures and of both the metabolites and the pharmaceutically acceptable bioprecursors (otherwise referred to as pro-drugs) of the compounds of formula (I) are also within the scope of the present invention.

As above reported, within the compounds of formula (I) wherein R is other than hydrogen, R itself may be in any of the free positions of the pyridine ring, hence leading to 4-, 5- or 6-substituted 1H-pyrrolo[2,3-b]pyridine derivatives.

Preferred compounds of the invention are the compounds of formula (I) wherein R is hydrogen, halogen, cyano, hydroxy or a group —$OCOR_4$, —$(CH_2)_n NH_2$, —$(CH_2)_n NHR_4$, —$(CH_2)_n NHCOR_4$, —$(CH_2)_n NHCONR_4R_5$, —$(CH_2)_n NHCOOR_4$, —$(CH_2)_n NHSO_2R_4$, wherein n is 0 or 1 and $R_4$ and $R_5$ are, each independently, hydrogen or an optionally substituted group selected from alkyl, heterocyclyl, aryl or arylalkyl or, taken together to the nitrogen atom to which they are bonded, $R_4$ and $R_5$ form an optionally substituted pyrrolidino, piperidino, piperazino or morpholino group; and $R_1$, $R_2$ and $R_3$ have the above reported meanings.

Still more preferred, within this latter class, are the compounds of formula (I) wherein $R_3$ is hydrogen or a group selected from —$CONR_4R_5$, —$COOR_4$ or —$CONHOR_4$ wherein $R_4$ is as above defined.

Examples of preferred compounds of the invention, whenever appropriate in the form of pharmaceutically acceptable salts, e.g. hydrobromide or hydrochloride salts, are the following:

1. 3-(6-amino-1H-pyrrolo[2,3-b]pyridin-3-yl)-2-phenyl-2-propenamide;
2. 3-(6-acetylamino-1H-pyrrolo[2,3-b]pyridin-3-yl)-2-phenyl-2-propenamide;
3. 3-(6-chloro-1H-pyrrolo[2,3-b]pyridin-3-yl)-2-phenyl-2-propenamide;
4. 3-(6-bromo-1H-pyrrolo[2,3-b]pyridin-3-yl)-2-phenyl-2-propenamide;
5. 3-(6-cyano-1H-pyrrolo[2,3-b]pyridin-3-yl)-2-phenyl-2-propenamide;
6. 3-(6-hydroxy-1H-pyrrolo[2,3-b]pyridin-3-yl)-2-phenyl-2-propenamide;
7. 3-[6-(aminomethyl)-1H-pyrrolo[2,3-b]pyridin-3-yl]-2-phenyl-2-propenamide;
8. 3-{6-[(methylamino)methyl]-1H-pyrrolo[2,3-b]pyridin-3-yl}-2-phenyl-2-propenamide;
9. 3-{6-[(benzylamino)methyl]-1H-pyrrolo[2,3-b]pyridin-3-yl}-2-phenyl-2-propenamide;
10. N-({3-[3-amino-3-oxo-2-phenyl-1-propenyl]-1H-pyrrolo[2,3-b]pyridin-6-yl}methyl)benzamide;
11. 2-phenyl-3-(6-{[(phenylacetyl)amino]methyl}-1H-pyrrolo[2,3-b]pyridin-3-yl)-2-propenamide;
12. 3-[3-amino-3-oxo-2-phenyl-1-propenyl]-1H-pyrrolo[2,3-b]pyridin-6-yl benzoate;
13. 3-[3-amino-3-oxo-2-phenyl-1-propenyl]-1H-pyrrolo[2,3-b]pyridin-6-yl acetate;
14. 3-[6-(methylamino)-1H-pyrrolo[2,3-b]pyridin-3-yl]-2-phenyl-2-propenamide;
15. 3-[6-(ethylamino)-1H-pyrrolo[2,3-b]pyridin-3-yl]-2-phenyl-2-propenamide;
16. 3-[6-(isopropylamino)-1H-pyrrolo[2,3-b]pyridin-3-yl]-2-phenyl-2-propenamide;
17. 3-[6-(cyclohexylamino)-1H-pyrrolo[2,3-b]pyridin-3-yl]-2-phenyl-2-propenamide;
18. 3-(6-anilino-1H-pyrrolo[2,3-b]pyridin-3-yl)-2-phenyl-2-propenamide;
19. 3-[6-(4-bromoanilino)-1H-pyrrolo[2,3-b]pyridin-3-yl]-2-phenyl-2-propenamide;
20. 3-[6-(3-hydroxyanilino)-1H-pyrrolo[2,3-b]pyridin-3-yl]-2-phenyl-2-propenamide;
21. 3-{6-[4-(aminosulfonyl)anilino]-1H-pyrrolo[2,3-b]pyridin-3-yl}-2-phenyl-2-propenamide;
22. 4-({3-[3-amino-3-oxo-2-phenyl-1-propenyl]-1H-pyrrolo[2,3-b]pyridin-6-yl}amino)benzamide;
23. 3-[6-(3-aminoanilino)-1H-pyrrolo[2,3-b]pyridin-3-yl]-2-phenyl-2-propenamide;
24. 2-phenyl-3-[6-(3-pyridinylamino)-1H-pyrrolo[2,3-b]pyridin-3-yl]-2-propenamide;
25. 2-phenyl-3-[6-(1,3-thiazol-2-ylamino)-1H-pyrrolo[2,3-b]pyridin-3-yl]-2-propenamide;
26. 3-[6-(benzylamino)-1H-pyrrolo[2,3-b]pyridin-3-yl]-2-phenyl-2-propenamide;

27. 3-(6-{[4-(aminosulfonyl)benzyl]amino}-1H-pyrrolo[2,3-b]pyridin-3-yl)-2-phenyl-2-propenamide;
28. 3-[6-(acetylamino)-1H-pyrrolo[2,3-b]pyridin-3-yl]-2-phenyl-2-propenamide;
29. N-{3-[3-amino-3-oxo-2-phenyl-1-propenyl]-1H-pyrrolo[2,3-b]pyridin-6-yl}benzamide;
30. N-{3-[3-amino-3-oxo-2-phenyl-1-propenyl]-1H-pyrrolo[2,3-b]pyridin-6-yl}-4-bromobenzamide;
31. N-{3-[3-amino-3-oxo-2-phenyl-1-propenyl]-1H-pyrrolo[2,3-b]pyridin-6-yl}-3-hydroxybenzamide;
32. 3-amino-N-{3-[3-amino-3-oxo-2-phenyl-1-propenyl]-1H-pyrrolo[2,3-b]pyridin-6-yl}benzamide;
33. 3-[6-(butyrylamino)-1H-pyrrolo[2,3-b]pyridin-3-yl]-2-phenyl-2-propenamide;
34. 2-phenyl-3-{6-[(phenylacetyl)amino]-1H-pyrrolo[2,3-b]pyridin-3-yl}-2-propenamide;
35. 3-(6-{[(3-hydroxyphenyl)acetyl]amino}-1H-pyrrolo[2,3-b]pyridin-3-yl)-2-phenyl-2-propenamide;
36. 3-(6-{[(3-chlorophenyl)acetyl]amino}-1H-pyrrolo[2,3-b]pyridin-3-yl)-2-phenyl-2-propenamide;
37. 3-(6-{[(3-aminophenyl)acetyl]amino}-1H-pyrrolo[2,3-b]pyridin-3-yl)-2-phenyl-2-propenamide;
38. 2-phenyl-3-{6-[(3-pyridinylacetyl)amino]-1H-pyrrolo[2,3-b]pyridin-3-yl}-2-propenamide;
39. N-{3-[3-amino-3-oxo-2-phenyl-1-propenyl]-1H-pyrrolo[2,3-b]pyridin-6-yl}-1H-indole-3-carboxamide;
40. 3-{6-[(1H-indol-3-ylacetyl)amino]-1H-pyrrolo[2,3-b]pyridin-3-yl}-2-phenyl-2-propenamide;
41. N-{3-[3-amino-3-oxo-2-phenyl-1-propenyl]-1H-pyrrolo[2,3-b]pyridin-6-yl}-2-thiophenecarboxamide;
42. N-{3-[3-amino-3-oxo-2-phenyl-1-propenyl]-1H-pyrrolo[2,3-b]pyridin-6-yl}[1,1'-biphenyl]-4-carboxamide;
43. 3-{6-[([1,1'-biphenyl]-4-ylacetyl)amino]-1H-pyrrolo[2,3-b]pyridin-3-yl}-2-phenyl-2-propenamide;
44. 3-{6-[(1,3-oxazol-2-ylacetyl)amino]-1H-pyrrolo[2,3-b]pyridin-3-yl}-2-phenyl-2-propenamide;
45. 2-phenyl-3-{6-[(1,3-thiazol-2-ylacetyl)amino]-1H-pyrrolo[2,3-b]pyridin-3-yl}-2-propenamide;
46. 3-{6-[(aminocarbonyl)amino]-1H-pyrrolo[2,3-b]pyridin-3-yl}-2-phenyl-2-propenamide;
47. 3-(6-{[(methylamino)carbonyl]amino}-1H-pyrrolo[2,3-b]pyridin-3-yl)-2-phenyl-2-propenamide;
48. 3-{6-[(anilinocarbonyl)amino]-1H-pyrrolo[2,3-b]pyridin-3-yl}-2-phenyl-2-propenamide;
49. 3-(6-{[(4-bromoanilino)carbonyl]amino}-1H-pyrrolo[2,3-b]pyridin-3-yl)-2-phenyl-2-propenamide;
50. 3-(6-{[(3-hydroxyanilino)carbonyl]amino}-1H-pyrrolo[2,3-b]pyridin-3-yl)-2-phenyl-2-propenamide;
51. 3-(6-{[(benzylamino)carbonyl]amino}-1H-pyrrolo[2,3-b]pyridin-3-yl)-2-phenyl-2-propenamide;
52. N-{3-[3-amino-3-oxo-2-phenyl-1-propenyl]-1H-pyrrolo[2,3-b]pyridin-6-yl}-1-piperidinecarboxamide;
53. N-{3-[3-amino-3-oxo-2-phenyl-1-propenyl]-1H-pyrrolo[2,3-b]pyridin-6-yl}-4-methyl-1-piperazinecarboxamide;
54. N-{3-[3-amino-3-oxo-2-phenyl-1-propenyl]-1H-pyrrolo[2,3-b]pyridin-6-yl}-4-morpholinecarboxamide;
55. N-{3-[3-amino-3-oxo-2-phenyl-1-propenyl]-1H-pyrrolo[2,3-b]pyridin-6-yl}-1-pyrrolidinecarboxamide;
56. ethyl 3-[3-amino-3-oxo-2-phenyl-1-propenyl]-1H-pyrrolo[2,3-b]pyridin-6-ylcarbamate;
57. tert-butyl 3-[3-amino-3-oxo-2-phenyl-1-propenyl]-1H-pyrrolo[2,3-b]pyridin-6-ylcarbamate;
58. 3-{6-[(methylsulfonyl)amino]-1H-pyrrolo[2,3-b]pyridin-3-yl}-2-phenyl-2-propenamide;
59. 2-phenyl-3-{6-[(phenylsulfonyl)amino]-1H-pyrrolo[2,3-b]pyridin-3-yl}-2-propenamide;
60. 2-phenyl-3-(6-{[(phenylsulfonyl)methyl]amino}-1H-pyrrolo[2,3-b]pyridin-3-yl)-2-propenamide;
61. 3-(6-{[([1,1'-biphenyl]-4-ylmethyl)sulfonyl]amino}-1H-pyrrolo[2,3-b]pyridin-3-yl)-2-phenyl-2-propenamide;
62. 3-{6-[([1,1'-biphenyl]-4-ylsulfonyl)amino]-1H-pyrrolo[2,3-b]pyridin-3-yl}-2-phenyl-2-propenamide;
63. 3-(4-chloro-1H-pyrrolo[2,3-b]pyridin-3-yl)-2-phenyl-2-propenamide;
64. 3-(4-anilino-1H-pyrrolo[2,3-b]pyridin-3-yl)-2-phenyl-2-propenamide;
65. 3-[4-(4-bromoanilino)-1H-pyrrolo[2,3-b]pyridin-3-yl]-2-phenyl-2-propenamide;
66. 3-[4-(3-hydroxyanilino)-1H-pyrrolo[2,3-b]pyridin-3-yl]-2-phenyl-2-propenamide;
67. 3-{4-[4-(aminosulfonyl)anilino]-1H-pyrrolo[2,3-b]pyridin-3-yl}-2-phenyl-2-propenamide;
68. 4-({3-[3-amino-3-oxo-2-phenyl-1-propenyl]-1H-pyrrolo[2,3-b]pyridin-4-yl}amino)benzamide;
69. 3-[4-(3-aminoanilino)-1H-pyrrolo[2,3-b]pyridin-3-yl]-2-phenyl-2-propenamide;
70. 2-phenyl-3-[4-(3-pyridinylamino)-1H-pyrrolo[2,3-b]pyridin-3-yl]-2-propenamide;
71. 2-phenyl-3-[4-(1,3-thiazol-2-ylamino)-1H-pyrrolo[2,3-b]pyridin-3-yl]-2-propenamide;
72. 3-(4-amino-1H-pyrrolo[2,3-b]pyridin-3-yl)-2-phenyl-2-propenamide;
73. 3-[4-(methylamino)-1H-pyrrolo[2,3-b]pyridin-3-yl]-2-phenyl-2-propenamide;
74. 3-[4-(cyclohexylamino)-1H-pyrrolo[2,3-b]pyridin-3-yl]-2-phenyl-2-propenamide;
75. 3-[4-(benzylamino)-1H-pyrrolo[2,3-b]pyridin-3-yl]-2-phenyl-2-propenamide;
76. 3-(4-{[4-(aminosulfonyl)benzyl]amino}-1H-pyrrolo[2,3-b]pyridin-3-yl)-2-phenyl-2-propenamide;
77. 3-[4-(acetylamino)-1H-pyrrolo[2,3-b]pyridin-3-yl]-2-phenyl-2-propenamide;
78. N-{3-[3-amino-3-oxo-2-phenyl-1-propenyl]-1H-pyrrolo[2,3-b]pyridin-4-yl}benzamide;
79. N-{3-[3-amino-3-oxo-2-phenyl-1-propenyl]-1H-pyrrolo[2,3-b]pyridin-4-yl}-4-bromobenzamide;
80. N-{3-[3-amino-3-oxo-2-phenyl-1-propenyl]-1H-pyrrolo[2,3-b]pyridin-4-yl}-3-hydroxybenzamide;
81. 3-amino-N-{3-[3-amino-3-oxo-2-phenyl-1-propenyl]-1H-pyrrolo[2,3-b]pyridin-4-yl}benzamide;
82. 3-[4-(butyrylamino)-1H-pyrrolo[2,3-b]pyridin-3-yl]-2-phenyl-2-propenamide;
83. 2-phenyl-3-}4-[(phenylacetyl)amino]-1H-pyrrolo[2,3-b]pyridin-3-yl}-2-propenamide;
84. 3-(4-{[(3-hydroxyphenyl)acetyl]amino}-1H-pyrrolo[2,3-b]pyridin-3-yl)-2-phenyl-2-propenamide;
85. 3-(4-{[(3-chlorophenyl)acetyl]amino}-1H-pyrrolo[2,3-b]pyridin-3-yl)-2-phenyl-2-propenamide;
86. 3-(4-{[(3-aminophenyl)acetyl]amino}-1H-pyrrolo[2,3-b]pyridin-3-yl)-2-phenyl-2-propenamide;
87. 2-phenyl-3-{4-[(3-pyridinylacetyl)amino]-1H-pyrrolo[2,3-b]pyridin-3-yl}-2-propenamide;
88. N-{3-[3-amino-3-oxo-2-phenyl-1-propenyl]-1H-pyrrolo[2,3-b]pyridin-4-yl}-1H-indole-3-carboxamide;
89. 3-{4-[(1H-indol-3-ylacetyl)amino]-1H-pyrrolo[2,3-b]pyridin-3-yl}-2-phenyl-2-propenamide;
90. N-{3-[3-amino-3-oxo-2-phenyl-1-propenyl]-1H-pyrrolo[2,3-b]pyridin-4-yl}-2-thiophenecarboxamide;
91. N-{3-[3-amino-3-oxo-2-phenyl-1-propenyl]-1H-pyrrolo[2,3-b]pyridin-4-yl}[1,1'-biphenyl]-4-carboxamide;
92. 3-{4-[(1,3-oxazol-2-ylacetyl)amino]-1H-pyrrolo[2,3-b]pyridin-3-yl}-2-phenyl-2-propenamide;
93. 2-phenyl-3-{4-[(1,3-thiazol-2-ylacetyl)amino]-1H-pyrrolo[2,3-b]pyridin-3-yl}-2-propenamide;
94. 3-{4-[(aminocarbonyl)amino]-1H-pyrrolo[2,3-b]pyridin-3-yl}-2-phenyl-2-propenamide;

95. 3-(4-{[(methylamino)carbonyl]amino}-1H-pyrrolo[2,3-b]pyridin-3-yl)-2-phenyl-2-propenamide;
96. 3-{4-[(anilinocarbonyl)amino]-1H-pyrrolo[2,3-b]pyridin-3-yl}-2-phenyl-2-propenamide;
97. 3-(4-{[(4-bromoanilino)carbonyl]amino}-1H-pyrrolo[2,3-b]pyridin-3-yl)-2-phenyl-2-propenamide;
98. 3-(4-{[(3-hydroxyanilino)carbonyl]amino}-1H-pyrrolo[2,3-b]pyridin-3-yl)-2-phenyl-2-propenamide;
99. 3-(4-{[(benzylamino)carbonyl]amino}-1H-pyrrolo[2,3-b]pyridin-3-yl)-2-phenyl-2-propenamide;
100. N-{3-[3-amino-3-oxo-2-phenyl-1-propenyl]-1H-pyrrolo[2,3-b]pyridin-4-yl}-1-piperidinecarboxamide;
101. N-{3-[3-amino-3-oxo-2-phenyl-1-propenyl]-1H-pyrrolo[2,3-b]pyridin-4-yl}-1-pyrrolidinecarboxamide;
102. N-{3-[3-amino-3-oxo-2-phenyl-1-propenyl]-1H-pyrrolo[2,3-b]pyridin-4-yl}-4-methyl-1-piperazinecarboxamide;
103. N-{3-[3-amino-3-oxo-2-phenyl-1-propenyl]-1H-pyrrolo[2,3-b]pyridin-4-yl}-4-morpholinecarboxamide;
104. 1-ethyl 3-[3-amino-3-oxo-2-phenyl-1-propenyl]-1H-pyrrolo[2,3-b]pyridin-4-ylcarbamate;
105. 1-tert-butyl 3-[3-amino-3-oxo-2-phenyl-1-propenyl]-1H-pyrrolo[2,3-b]pyridin-4-ylcarbamate;
106. 3-{4-[(methylsulfonyl)amino]-1H-pyrrolo[2,3-b]pyridin-3-yl}-2-phenyl-2-propenamide;
107. 2-phenyl-3-{4-[(phenylsulfonyl)amino]-1H-pyrrolo[2,3-b]pyridin-3-yl}-2-propenamide;
108. 3-{4-[(benzylsulfonyl)amino]-1H-pyrrolo[2,3-b]pyridin-3-yl}-2-phenyl-2-propenamide;
109. 3-{4-[([1,1'-biphenyl]-4-ylsulfonyl)amino]-1H-pyrrolo[2,3-b]pyridin-3-yl}-2-phenyl-2-propenamide;
110. 3-(4-{[([1,1'-biphenyl]-4-ylmethyl)sulfonyl]amino}-1H-pyrrolo[2,3-b]pyridin-3-yl)-2-phenyl-2-propenamide;
111. 3-(5-amino-1H-pyrrolo[2,3-b]pyridin-3-yl)-2-phenyl-2-propenamide;
112. 3-[5-(methylamino)-1H-pyrrolo[2,3-b]pyridin-3-yl]-2-phenyl-2-propenamide;
113. 3-[5-(cyclohexylamino)-1H-pyrrolo[2,3-b]pyridin-3-yl]-2-phenyl-2-propenamide;
114. 3-[5-(benzylamino)-1H-pyrrolo[2,3-b]pyridin-3-yl]-2-phenyl-2-propenamide;
115. 3-(5-{[4-(aminosulfonyl)benzyl]amino}-1H-pyrrolo[2,3-b]pyridin-3-yl)-2-phenyl-2-propenamide;
116. 3-[5-(acetylamino)-1H-pyrrolo[2,3-b]pyridin-3-yl]-2-phenyl-2-propenamide;
117. N-{3-[3-amino-3-oxo-2-phenyl-1-propenyl]-1H-pyrrolo[2,3-b]pyridin-5-yl}benzamide;
118. N-{3-[3-amino-3-oxo-2-phenyl-1-propenyl]-1H-pyrrolo[2,3-b]pyridin-5-yl}-4-bromobenzamide;
119. N-{3-[3-amino-3-oxo-2-phenyl-1-propenyl]-1H-pyrrolo[2,3-b]pyridin-5-yl}-3-hydroxybenzamide;
120. 3-amino-N-{3-[3-amino-3-oxo-2-phenyl-1-propenyl]-1H-pyrrolo[2,3-b]pyridin-5-yl}benzamide;
121. 3-[5-(butyrylamino)-1H-pyrrolo[2,3-b]pyridin-3-yl]-2-phenyl-2-propenamide;
122. 2-phenyl-3-{5-[(phenylacetyl)amino]-1H-pyrrolo[2,3-b]pyridin-3-yl}-2-propenamide;
123. 3-(5-{[(3-hydroxyphenyl)acetyl]amino}-1H-pyrrolo[2,3-b]pyridin-3-yl)-2-phenyl-2-propenamide;
124. 3-(5-{[(3-chlorophenyl)acetyl]amino}-1H-pyrrolo[2,3-b]pyridin-3-yl)-2-phenyl-2-propenamide;
125. 3-(5-{[(3-aminophenyl)acetyl]amino}-1H-pyrrolo[2,3-b]pyridin-3-yl)-2-phenyl-2-propenamide;
126. 2-phenyl-3-{5-[(3-pyridinylacetyl)amino]-1H-pyrrolo[2,3-b]pyridin-3-yl}-2-propenamide;
127. N-{3-[3-amino-3-oxo-2-phenyl-1-propenyl]-1H-pyrrolo[2,3-b]pyridin-5-yl}-1H-indole-3-carboxamide;
128. 3-{5-[(1H-indol-3-ylacetyl)amino]-1H-pyrrolo[2,3-b]pyridin-3-yl}-2-phenyl-2-propenamide;
129. N-{3-[3-amino-3-oxo-2-phenyl-1-propenyl]-1H-pyrrolo[2,3-b]pyridin-5-yl}-2-thiophenecarboxamide;
130. N-{3-[3-amino-3-oxo-2-phenyl-1-propenyl]-1H-pyrrolo[2,3-b]pyridin-5-yl}[1,1'-biphenyl]-4-carboxamide;
131. 3-{5-[(1,3-oxazol-2-ylacetyl)amino]-1H-pyrrolo[2,3-b]pyridin-3-yl}-2-phenyl-2-propenamide;
132. 2-phenyl-3-{5-[(1,3-thiazol-2-ylacetyl)amino]-1H-pyrrolo[2,3-b]pyridin-3-yl}-2-propenamide;
133. 3-{5-[(aminocarbonyl)amino]-1H-pyrrolo[2,3-b]pyridin-3-yl}-2-phenyl-2-propenamide;
134. 3-(5-{[(methylamino)carbonyl]amino}-1H-pyrrolo[2,3-b]pyridin-3-yl)-2-phenyl-2-propenamide;
135. 3-{5-[(anilinocarbonyl)amino]-1H-pyrrolo[2,3-b]pyridin-3-yl}-2-phenyl-2-propenamide;
136. 3-(5-{[(4-bromoanilino)carbonyl]amino}-1H-pyrrolo[2,3-b]pyridin-3-yl)-2-phenyl-2-propenamide;
137. 3-(5-{[(3-hydroxyanilino)carbonyl]amino}-1H-pyrrolo[2,3-b]pyridin-3-yl)-2-phenyl-2-propenamide;
138. 3-(5-{[(benzylamino)carbonyl]amino}-1H-pyrrolo[2,3-b]pyridin-3-yl)-2-phenyl-2-propenamide;
139. N-{3-[3-amino-3-oxo-2-phenyl-1-propenyl]-1H-pyrrolo[2,3-b]pyridin-5-yl}-1-piperidinecarboxamide;
140. N-{3-[3-amino-3-oxo-2-phenyl-1-propenyl]-1H-pyrrolo[2,3-b]pyridin-5-yl}-1-pyrrolidinecarboxamide;
141. N-{3-[3-amino-3-oxo-2-phenyl-1-propenyl]-1H-pyrrolo[2,3-b]pyridin-5-yl}-4-methyl-1-piperazinecarboxamide;
142. N-{3-[3-amino-3-oxo-2-phenyl-1-propenyl]-1H-pyrrolo[2,3-b]pyridin-5-yl}-4-morpholinecarboxamide;
143. ethyl 3-[3-amino-3-oxo-2-phenyl-1-propenyl]-1H-pyrrolo[2,3-b]pyridin-5-ylcarbamate;
144. tert-butyl 3-[3-amino-3-oxo-2-phenyl-1-propenyl]-1H-pyrrolo[2,3-b]pyridin-5-ylcarbamate;
145. 3-{5-[(methylsulfonyl)amino]-1H-pyrrolo[2,3-b]pyridin-3-yl}-2-phenyl-2-propenamide;
146. 2-phenyl-3-{5-[(phenylsulfonyl)amino]-1H-pyrrolo[2,3-b]pyridin-3-yl}-2-propenamide;
147. 3-{5-[(benzylsulfonyl)amino]-1H-pyrrolo[2,3-b]pyridin-3-yl}-2-phenyl-2-propenamide;
148. 3-{5-[([1,1'-biphenyl]-4-ylsulfonyl)amino]-1H-pyrrolo[2,3-b]pyridin-3-yl}-2-phenyl-2-propenamide;
149. 3-(5-{[([1,1'-biphenyl]-4-ylmethyl)sulfonyl]amino}-1H-pyrrolo[2,3-b]pyridin-3-yl)-2-phenyl-2-propenamide;
150. 3-(6-amino-1H-pyrrolo[2,3-b]pyridin-3-yl)-2-phenyl-2-propenoic acid;
151. 3-(6-acetylamino-1H-pyrrolo[2,3-b]pyridin-3-yl)-2-phenyl-2-propenoic acid;
152. 3-(6-chloro-1H-pyrrolo[2,3-b]pyridin-3-yl)-2-phenyl-2-propenoic acid;
153. 3-(6-bromo-1H-pyrrolo[2,3-b]pyridin-3-yl)-2-phenyl-2-propenoic acid;
154. 3-(6-cyano-1H-pyrrolo[2,3-b]pyridin-3-yl)-2-phenyl-2-propenoic acid;
155. 3-(6-hydroxy-1H-pyrrolo[2,3-b]pyridin-3-yl)-2-phenyl-2-propenoic acid;
156. 3-[6-(aminomethyl)-1H-pyrrolo[2,3-b]pyridin-3-yl]-2-phenyl-2-propenoic acid;
157. 3-{6-[(methylamino)methyl]-1H-pyrrolo[2,3-b]pyridin-3-yl}-2-phenyl-2-propenoic acid;
158. 3-{6-[(benzylamino)methyl]-1H-pyrrolo[2,3-b]pyridin-3-yl}-2-phenyl-2-propenoic acid;
159. 3-{6-[(benzoylamino)methyl]-1H-pyrrolo[2,3-b]pyridin-3-yl}-2-phenyl-2-propenoic acid;
160. 2-phenyl-3-(6-{[(phenylacetyl)amino]methyl}-1H-pyrrolo[2,3-b]pyridin-3-yl)-2-propenoic acid;

161. 3-[6-(benzoyloxy)-1H-pyrrolo[2,3-b]pyridin-3-yl]-2-phenyl-2-propenoic acid;
162. 3-[6-(acetyloxy)-1H-pyrrolo[2,3-b]pyridin-3-yl]-2-phenyl-2-propenoic acid;
163. 3-[6-(methylamino)-1H-pyrrolo[2,3-b]pyridin-3-yl]-2-phenyl-2-propenoic acid;
164. 3-[6-(ethylamino)-1H-pyrrolo[2,3-b]pyridin-3-yl]-2-phenyl-2-propenoic acid;
165. 3-[6-(isopropylamino)-1H-pyrrolo[2,3-b]pyridin-3-yl]-2-phenyl-2-propenoic acid;
166. 3-[6-(cyclohexylamino)-1H-pyrrolo[2,3-b]pyridin-3-yl]-2-phenyl-2-propenoic acid;
167. 3-(6-anilino-1H-pyrrolo[2,3-b]pyridin-3-yl)-2-phenyl-2-propenoic acid;
168. 3-[6-(4-bromoanilino)-1H-pyrrolo[2,3-b]pyridin-3-yl]-2-phenyl-2-propenoic acid;
169. 3-[6-(3-hydroxyanilino)-1H-pyrrolo[2,3-b]pyridin-3-yl]-2-phenyl-2-propenoic acid;
170. 3-{6-[4-(aminosulfonyl)anilino]-1H-pyrrolo[2,3-b]pyridin-3-yl}-2-phenyl-2-propenoic acid;
171. 3-{6-[4-(aminocarbonyl)anilino]-1H-pyrrolo[2,3-b]pyridin-3-yl}-2-phenyl-2-propenoic acid;
172. 3-[6-(3-aminoanilino)-1H-pyrrolo[2,3-b]pyridin-3-yl]-2-propenoic acid;
173. 2-phenyl-3-[6-(3-pyridinylamino)-1H-pyrrolo[2,3-b]pyridin-3-yl]-2-propenoic acid;
174. 2-phenyl-3-[6-(1,3-thiazol-2-ylamino)-1H-pyrrolo[2,3-b]pyridin-3-yl]-2-propenoic acid;
175. 3-[6-(benzylamino)-1H-pyrrolo[2,3-b]pyridin-3-yl]-2-phenyl-2-propenoic acid;
176. 3-(6-{[4-(aminosulfonyl)benzyl]amino}-1H-pyrrolo[2,3-b]pyridin-3-yl)-2-phenyl-2-propenoic acid;
177. 3-[6-(acetylamino)-1H-pyrrolo[2,3-b]pyridin-3-yl]-2-phenyl-2-propenoic acid;
178. 3-[6-(benzoylamino)-1H-pyrrolo[2,3-b]pyridin-3-yl]-2-phenyl-2-propenoic acid;
179. 3-{6-[(4-bromobenzoyl)amino]-1H-pyrrolo[2,3-b]pyridin-3-yl}-2-phenyl-2-propenoic acid;
180. 3-{6-[(3-hydroxybenzoyl)amino]-1H-pyrrolo[2,3-b]pyridin-3-yl}-2-phenyl-2-propenoic acid;
181. 3-{6-[(3-aminobenzoyl)amino]-1H-pyrrolo[2,3-b]pyridin-3-yl}-2-phenyl-2-propenoic acid;
182. 3-[6-(butyrylamino)-1H-pyrrolo[2,3-b]pyridin-3-yl]-2-phenyl-2-propenoic acid;
183. 2-phenyl-3-{6-[(phenylacetyl)amino]-1H-pyrrolo[2,3-b]pyridin-3-yl}-2-propenoic acid;
184. 3-(6-{[(3-hydroxyphenyl)acetyl]amino}-1H-pyrrolo[2,3-b]pyridin-3-yl)-2-phenyl-2-propenoic acid;
185. 3-(6-{[(3-chlorophenyl)acetyl]amino}-1H-pyrrolo[2,3-b]pyridin-3-yl)-2-phenyl-2-propenoic acid;
186. 3-(6-{[(3-aminophenyl)acetyl]amino}-1H-pyrrolo[2,3-b]pyridin-3-yl)-2-phenyl-2-propenoic acid;
187. 2-phenyl-3-{6-[(3-pyridinylacetyl)amino]-1H-pyrrolo[2,3-b]pyridin-3-yl}-2-propenoic acid;
188. 3-{6-[(1H-indol-3-ylcarbonyl)amino]-1H-pyrrolo[2,3-b]pyridin-3-yl}-2-phenyl-2-propenoic acid;
189. 3-{6-[(1H-indol-3-ylacetyl)amino]-1H-pyrrolo[2,3-b]pyridin-3-yl}-2-phenyl-2-propenoic acid;
190. 2-phenyl-3-{6-[(2-thienylcarbonyl)amino]-1H-pyrrolo[2,3-b]pyridin-3-yl}-2-propenoic acid;
191. 3-{6-[([1,1'-biphenyl]-4-ylcarbonyl)amino]-1H-pyrrolo[2,3-b]pyridin-3-yl}-2-phenyl-2-propenoic acid;
192. 3-{6-[([1,1'-biphenyl]-4-ylacetyl)amino]-1H-pyrrolo[2,3-b]pyridin-3-yl}-2-phenyl-2-propenoic acid;
193. 3-{6-[(1,3-oxazol-2-ylacetyl)amino]-1H-pyrrolo[2,3-b]pyridin-3-yl}-2-phenyl-2-propenoic acid;
194. 2-phenyl-3-{6-[(1,3-thiazol-2-ylacetyl)amino]-1H-pyrrolo[2,3-b]pyridin-3-yl}-2-propenoic acid;
195. 3-{6-[(aminocarbonyl)amino]-1H-pyrrolo[2,3-b]pyridin-3-yl}-2-phenyl-2-propenoic acid;
196. 3-(6-{[(methylamino)carbonyl]amino}-1H-pyrrolo[2,3-b]pyridin-3-yl)-2-phenyl-2-propenoic acid;
197. 3-{6-[(anilinocarbonyl)amino]-1H-pyrrolo[2,3-b]pyridin-3-yl}-2-phenyl-2-propenoic acid;
198. 3-(6-{[(4-bromoanilino)carbonyl]amino}-1H-pyrrolo[2,3-b]pyridin-3-yl)-2-phenyl-2-propenoic acid;
199. 3-(6-{[(3-hydroxyanilino)carbonyl]amino}-1H-pyrrolo[2,3-b]pyridin-3-yl)-2-phenyl-2-propenoic acid;
200. 3-(6-{[(benzylamino)carbonyl]amino}-1H-pyrrolo[2,3-b]pyridin-3-yl)-2-phenyl-2-propenoic acid;
201. 2-phenyl-3-{6-[(1-piperidinylcarbonyl)amino]-1H-pyrrolo[2,3-b]pyridin-3-yl}-2-propenoic acid;
202. 2-phenyl-3-{6-[(1-pyrrolidinylcarbonyl)amino]-1H-pyrrolo[2,3-b]pyridin-3-yl}-2-propenoic acid;
203. 3-(6-{[(4-methyl-1-piperazinyl)carbonyl]amino}-1H-pyrrolo[2,3-b]pyridin-3-yl)-2-phenyl-2-propenoic acid;
204. 3-{6-[(4-morpholinylcarbonyl)amino]-1H-pyrrolo[2,3-b]pyridin-3-yl}-2-phenyl-2-propenoic acid;
205. 3-{6-[(ethoxycarbonyl)amino]-1H-pyrrolo[2,3-b]pyridin-3-yl}-2-phenyl-2-propenoic acid;
206. 3-{6-[(tert-butoxycarbonyl)amino]-1H-pyrrolo[2,3-b]pyridin-3-yl}-2-phenyl-2-propenoic acid;
207. 3-{6-[(methylsulfonyl)amino]-1H-pyrrolo[2,3-b]pyridin-3-yl}-2-phenyl-2-propenoic acid;
208. 2-phenyl-3-{6-[(phenylsulfonyl)amino]-1H-pyrrolo[2,3-b]pyridin-3-yl}-2-propenoic acid;
209. 2-phenyl-3-(6-{[(phenylsulfonyl)methyl]amino}-1H-pyrrolo[2,3-b]pyridin-3-yl)-2-propenoic acid;
210. 3-(6-{[([1,1'-biphenyl]-4-ylmethyl)sulfonyl]amino}-1H-pyrrolo[2,3-b]pyridin-3-yl)-2-phenyl-2-propenoic acid;
211. 3-{6-[([1,1'-biphenyl]-4-ylsulfonyl)amino]-1H-pyrrolo[2,3-b]pyridin-3-yl}-2-phenyl-2-propenoic acid;
212. 3-(4-chloro-1H-pyrrolo[2,3-b]pyridin-3-yl)-2-phenyl-2-propenoic acid;
213. 3-(4-anilino-1H-pyrrolo[2,3-b]pyridin-3-yl)-2-phenyl-2-propenoic acid;
214. 3-[4-(4-bromoanilino)-1H-pyrrolo[2,3-b]pyridin-3-yl]-2-phenyl-2-propenoic acid;
215. 3-[4-(3-hydroxyanilino)-1H-pyrrolo[2,3-b]pyridin-3-yl]-2-phenyl-2-propenoic acid;
216. 3-{4-[4-(aminosulfonyl)anilino]-1H-pyrrolo[2,3-b]pyridin-3-yl}-2-phenyl-2-propenoic acid;
217. 3-{4-[4-(aminocarbonyl)anilino]-1H-pyrrolo[2,3-b]pyridin-3-yl}-2-phenyl-2-propenoic acid;
218. 3-[4-(3-aminoanilino)-1H-pyrrolo[2,3-b]pyridin-3-yl]-2-phenyl-2-propenoic acid;
219. 2-phenyl-3-[4-(3-pyridinylamino)-1H-pyrrolo[2,3-b]pyridin-3-yl]-2-propenoic acid;
220. 2-phenyl-3-[4-(1,3-thiazol-2-ylamino)-1H-pyrrolo[2,3-b]pyridin-3-yl]-2-propenoic acid;
221. 3-(4-amino-1H-pyrrolo[2,3-b]pyridin-3-yl)-2-phenyl-2-propenoic acid;
222. 3-[4-(methylamino)-1H-pyrrolo[2,3-b]pyridin-3-yl]-2-phenyl-2-propenoic acid;
223. 3-[4-(cyclohexylamino)-1H-pyrrolo[2,3-b]pyridin-3-yl]-2-phenyl-2-propenoic acid;
224. 3-[4-(benzylamino)-1H-pyrrolo[2,3-b]pyridin-3-yl]-2-phenyl-2-propenoic acid;
225. 3-(4-{[4-(aminosulfonyl)benzyl]amino}-1H-pyrrolo[2,3-b]pyridin-3-yl)-2-phenyl-2-propenoic acid;
226. 3-[4-(acetylamino)-1H-pyrrolo[2,3-b]pyridin-3-yl]-2-phenyl-2-propenoic acid;
227. 3-[4-(benzoylamino)-1H-pyrrolo[2,3-b]pyridin-3-yl]-2-phenyl-2-propenoic acid;

228. 3-{4-[(4-bromobenzoyl)amino]-1H-pyrrolo[2,3-b]pyridin-3-yl}-2-phenyl-2-propenoic acid;
229. 3-{4-[(3-hydroxybenzoyl)amino]-1H-pyrrolo[2,3-b]pyridin-3-yl}-2-phenyl-2-propenoic acid;
230. 3-{4-[(3-aminobenzoyl)amino]-1H-pyrrolo[2,3-b]pyridin-3-yl}-2-phenyl-2-propenoic acid;
231. 3-[4-(butyrylamino)-1H-pyrrolo[2,3-b]pyridin-3-yl]-2-phenyl-2-propenoic acid;
232. 2-phenyl-3-{4-[(phenylacetyl)amino]-1H-pyrrolo[2,3-b]pyridin-3-yl}-2-propenoic acid;
233. 3-(4-{[(3-hydroxyphenyl)acetyl]amino}-1H-pyrrolo[2,3-b]pyridin-3-yl)-2-phenyl-2-propenoic acid;
234. 3-(4-{[(3-chlorophenyl)acetyl]amino}-1H-pyrrolo[2,3-b]pyridin-3-yl)-2-phenyl-2-propenoic acid;
235. 3-(4-{[(3-aminophenyl)acetyl]amino}-1H-pyrrolo[2,3-b]pyridin-3-yl)-2-phenyl-2-propenoic acid;
236. 2-phenyl-3-{4-[(3-pyridinylacetyl)amino]-1H-pyrrolo[2,3-b]pyridin-3-yl}-2-propenoic acid;
237. 3-{4-[(1H-indol-3-ylcarbonyl)amino]-1H-pyrrolo[2,3-b]pyridin-3-yl}-2-phenyl-2-propenoic acid;
238. 3-{4-[(1H-indol-3-ylacetyl)amino]-1H-pyrrolo[2,3-b]pyridin-3-yl}-2-phenyl-2-propenoic acid;
239. 2-phenyl-3-{4-[(3-thienylcarbonyl)amino]-1H-pyrrolo[2,3-b]pyridin-3-yl}-2-propenoic acid;
240. 3-{4-[([1,1'-biphenyl]-4-ylcarbonyl)amino]-1H-pyrrolo[2,3-b]pyridin-3-yl}-2-phenyl-2-propenoic acid;
241. 3-{4-[(1,3-oxazol-2-ylacetyl)amino]-1H-pyrrolo[2,3-b]pyridin-3-yl}-2-phenyl-2-propenoic acid;
242. 2-phenyl-3-{4-[(1,3-thiazol-2-ylacetyl)amino]-1H-pyrrolo[2,3-b]pyridin-3-yl}-2-propenoic acid;
243. 3-{4-[(aminocarbonyl)amino]-1H-pyrrolo[2,3-b]pyridin-3-yl}-2-phenyl-2-propenoic acid;
244. 3-(4-{[(methylamino)carbonyl]amino}-1H-pyrrolo[2,3-b]pyridin-3-yl)-2-phenyl-2-propenoic acid;
245. 3-{4-[(anilinocarbonyl)amino]-1H-pyrrolo[2,3-b]pyridin-3-yl}-2-phenyl-2-propenoic acid;
246. 3-(4-{[(4-bromoanilino)carbonyl]amino}-1H-pyrrolo[2,3-b]pyridin-3-yl)-2-phenyl-2-propenoic acid;
247. 3-(4-{[(3-hydroxyanilino)carbonyl]amino}-1H-pyrrolo[2,3-b]pyridin-3-yl)-2-phenyl-2-propenoic acid;
248. 3-(4-{[(benzylamino)carbonyl]amino}-1H-pyrrolo[2,3-b]pyridin-3-yl)-2-phenyl-2-propenoic acid;
249. 2-phenyl-3-{4-[(1-piperidinylcarbonyl)amino]-1H-pyrrolo[2,3-b]pyridin-3-yl}-2-propenoic acid;
250. 2-phenyl-3-{4-[(1-pyrrolidinylcarbonyl)amino]-1H-pyrrolo[2,3-b]pyridin-3-yl}-2-propenoic acid;
251. 3-(4-{[(4-methyl-1-piperazinyl)carbonyl]amino}-1H-pyrrolo[2,3-b]pyridin-3-yl)-2-phenyl-2-propenoic acid;
252. 3-{4-[(4-morpholinylcarbonyl)amino]-1H-pyrrolo[2,3-b]pyridin-3-yl}-2-phenyl-2-propenoic acid;
253. 3-{4-[(ethoxycarbonyl)amino]-1H-pyrrolo[2,3-b]pyridin-3-yl}-2-phenyl-2-propenoic acid;
254. 3-{4-[(tert-butoxycarbonyl)amino]-1H-pyrrolo[2,3-b]pyridin-3-yl}-2-phenyl-2-propenoic acid;
255. 3-{4-[(methylsulfonyl)amino]-1H-pyrrolo[2,3-b]pyridin-3-yl}-2-phenyl-2-propenoic acid;
256. 2-phenyl-3-{4-[(phenylsulfonyl)amino]-1H-pyrrolo[2,3-b]pyridin-3-yl}-2-propenoic acid;
257. 3-{4-[(benzylsulfonyl)amino]-1H-pyrrolo[2,3-b]pyridin-3-yl}-2-phenyl-2-propenoic acid;
258. 3-{4-[([1,1'-biphenyl]-4-ylsulfonyl)amino]-1H-pyrrolo[2,3-b]pyridin-3-yl}-2-phenyl-2-propenoic acid;
259. 3-(4-{[([1,1'-biphenyl]-4-ylmethyl)sulfonyl]amino}-1H-pyrrolo[2,3-b]pyridin-3-yl)-2-phenyl-2-propenoic acid;
260. 3-(5-amino-1H-pyrrolo[2,3-b]pyridin-3-yl)-2-phenyl-2-propenoic acid;
261. 3-[5-(methylamino)-1H-pyrrolo[2,3-b]pyridin-3-yl]-2-phenyl-2-propenoic acid;
262. 3-[5-(cyclohexylamino)-1H-pyrrolo[2,3-b]pyridin-3-yl]-2-phenyl-2-propenoic acid;
263. 3-[5-(benzylamino)-1H-pyrrolo[2,3-b]pyridin-3-yl]-2-phenyl-2-propenoic acid;
264. 3-(5-{[4-(aminosulfonyl)benzyl]amino}-1H-pyrrolo[2,3-b]pyridin-3-yl)-2-phenyl-2-propenoic acid;
265. 3-[5-(acetylamino)-1H-pyrrolo[2,3-b]pyridin-3-yl]-2-phenyl-2-propenoic acid;
266. 3-[5-(benzoylamino)-1H-pyrrolo[2,3-b]pyridin-3-yl]-2-phenyl-2-propenoic acid;
267. 3-{5-[(4-bromobenzoyl)amino]-1H-pyrrolo[2,3-b]pyridin-3-yl}-2-phenyl-2-propenoic acid;
268. 3-{5-[(3-hydroxybenzoyl)amino]-1H-pyrrolo[2,3-b]pyridin-3-yl}-2-phenyl-2-propenoic acid;
269. 3-{5-[(3-aminobenzoyl)amino]-1H-pyrrolo[2,3-b]pyridin-3-yl}-2-phenyl-2-propenoic acid;
270. 3-[5-(butyrylamino)-1H-pyrrolo[2,3-b]pyridin-3-yl]-2-phenyl-2-propenoic acid;
271. 2-phenyl-3-{5-[(phenylacetyl)amino]-1H-pyrrolo[2,3-b]pyridin-3-yl}-2-propenoic acid;
272. 3-(5-{[(3-hydroxyphenyl)acetyl]amino}-1H-pyrrolo[2,3-b]pyridin-3-yl)-2-phenyl-2-propenoic acid;
273. 3-(5-{[(3-chlorophenyl)acetyl]amino}-1H-pyrrolo[2,3-b]pyridin-3-yl)-2-phenyl-2-propenoic acid;
274. 3-(5-{[(3-aminophenyl)acetyl]amino}-1H-pyrrolo[2,3-b]pyridin-3-yl)-2-phenyl-2-propenoic acid;
275. 2-phenyl-3-{5-[(3-pyridinylacetyl)amino]-1H-pyrrolo[2,3-b]pyridin-3-yl}-2-propenoic acid;
276. 3-{5-[(1H-indol-3-ylcarbonyl)amino]-1H-pyrrolo[2,3-b]pyridin-3-yl}-2-phenyl-2-propenoic acid;
277. 3-{5-[(1H-indol-3-ylacetyl)amino]-1H-pyrrolo[2,3-b]pyridin-3-yl}-2-phenyl-2-propenoic acid;
278. 2-phenyl-3-{5-[(3-thienylcarbonyl)amino]-1H-pyrrolo[2,3-b]pyridin-3-yl}-2-propenoic acid;
279. 3-{5-[([1,1'-biphenyl]-4-ylcarbonyl)amino]-1H-pyrrolo[2,3-b]pyridin-3-yl}-2-phenyl-2-propenoic acid;
280. 3-{5-[(1,3-oxazol-2-ylacetyl)amino]-1H-pyrrolo[2,3-b]pyridin-3-yl}-2-phenyl-2-propenoic acid;
281. 2-phenyl-3-{5-[(1,3-thiazol-2-ylacetyl)amino]-1H-pyrrolo[2,3-b]pyridin-3-yl}-2-propenoic acid;
282. 3-{5-[(aminocarbonyl)amino]-1H-pyrrolo[2,3-b]pyridin-3-yl}-2-phenyl-2-propenoic acid;
283. 3-(5-{[(methylamino)carbonyl]amino}-1H-pyrrolo[2,3-b]pyridin-3-yl)-2-phenyl-2-propenoic acid;
284. 3-{5-[(anilinocarbonyl)amino]-1H-pyrrolo[2,3-b]pyridin-3-yl}-2-phenyl-2-propenoic acid;
285. 3-(5-{[(4-bromoanilino)carbonyl]amino}-1H-pyrrolo[2,3-b]pyridin-3-yl)-2-phenyl-2-propenoic acid;
286. 3-(5-{[(3-hydroxyanilino)carbonyl]amino}-1H-pyrrolo[2,3-b]pyridin-3-yl)-2-phenyl-2-propenoic acid;
287. 3-(5-{[(benzylamino)carbonyl]amino}-1H-pyrrolo[2,3-b]pyridin-3-yl)-2-phenyl-2-propenoic acid;
288. 2-phenyl-3-{5-[(1-piperidinylcarbonyl)amino]-1H-pyrrolo[2,3-b]pyridin-3-yl}-2-propenoic acid;
289. 2-phenyl-3-{5-[(1-pyrrolidinylcarbonyl)amino]-1H-pyrrolo[2,3-b]pyridin-3-yl}-2-propenoic acid;
290. 3-(5-{[(4-methyl-1-piperazinyl)carbonyl]amino}-1H-pyrrolo[2,3-b]pyridin-3-yl)-2-phenyl-2-propenoic acid;
291. 3-{5-[(4-morpholinylcarbonyl)amino]-1H-pyrrolo[2,3-b]pyridin-3-yl}-2-phenyl-2-propenoic acid;
292. 3-{5-[(ethoxycarbonyl)amino]-1H-pyrrolo[2,3-b]pyridin-3-yl}-2-phenyl-2-propenoic acid;
293. 3-{5-[(tert-butoxycarbonyl)amino]-1H-pyrrolo[2,3-b]pyridin-3-yl}-2-phenyl-2-propenoic acid;
294. 3-{5-[(methylsulfonyl)amino]-1H-pyrrolo[2,3-b]pyridin-3-yl}-2-phenyl-2-propenoic acid;

295. 2-phenyl-3-{5-[(phenylsulfonyl)amino]-1H-pyrrolo[2,3-b]pyridin-3-yl}-2-propenoic acid;
296. 3-{5-[(benzylsulfonyl)amino]-1H-pyrrolo[2,3-b]pyridin-3-yl}-2-phenyl-2-propenoic acid;
297. 3-{5-[([1,1'-biphenyl]-4-ylsulfonyl)amino]-1H-pyrrolo[2,3-b]pyridin-3-yl}-2-phenyl-2-propenoic acid;
298. 3-(5-{[([1,1'-biphenyl]-4-ylmethyl)sulfonyl]amino}-1H-pyrrolo[2,3-b]pyridin-3-yl)-2-phenyl-2-propenoic acid;
299. 2-phenyl-3-(1H-pyrrolo[2,3-b]pyridin-3-yl)-2-propenamide;
300. 2-phenyl-3-(1H-pyrrolo[2,3-b]pyridin-3-yl)-2-propenoic acid;
301. N-butyl-2-phenyl-3-(1H-pyrrolo[2,3-b]pyridin-3-yl)-2-propenamide;
302. 2-(4-chlorophenyl)-3-(1H-pyrrolo[2,3-b]pyridin-3-yl)-2-propenoic acid;
303. 3-(1H-pyrrolo[2,3-b]pyridin-3-yl)-2-(4-tolyl)-2-propenoic acid;
304. 3-(1H-pyrrolo[2,3-b]pyridin-3-yl)-2-[2-(trifluoromethyl)phenyl]-2-propenoic acid;
305. 2-(1-acetyl-1H-indol-3-yl)-3-(1H-pyrrolo[2,3-b]pyridin-3-yl)-2-propenoic acid;
306. 2-(1H-indol-3-yl)-3-(1H-pyrrolo[2,3-b]pyridin-3-yl)-2-propenoic acid;
307. 2-(3-fluoro-4-hydroxyphenyl)-3-(1H-pyrrolo[2,3-b]pyridin-3-yl)-2-propenoic acid;
308. 2-(2,3-dihydro-1H-inden-5-yl)-3-(1H-pyrrolo[2,3-b]pyridin-3-yl)-2-propenoic acid;
309. 2-(3-pyridinyl)-3-(1H-pyrrolo[2,3-b]pyridin-3-yl)-2-propenoic acid;
310. 2-(4-hydroxyphenyl)-3-(1H-pyrrolo[2,3-b]pyridin-3-yl)-2-propenoic acid;
311. 2-(4-methoxyphenyl)-3-(1H-pyrrolo[2,3-b]pyridin-3-yl)-2-propenoic acid;
312. 2-(2-hydroxyphenyl)-3-(1H-pyrrolo[2,3-b]pyridin-3-yl)-2-propenoic acid;
313. 2-(2-methoxyphenyl)-3-(1H-pyrrolo[2,3-b]pyridin-3-yl)-2-propenoic acid;
314. 2-[1,1'-biphenyl]-4-yl-3-(1H-pyrrolo[2,3-b]pyridin-3-yl)-2-propenoic acid;
315. 2-(4-hydroxy-5-isopropyl-2-methylphenyl)-3-(1H-pyrrolo[2,3-b]pyridin-3-yl)-2-propenoic acid;
316. 2-(4-hydroxy-3-methoxyphenyl)-3-(1H-pyrrolo[2,3-b]pyridin-3-yl)-2-propenoic acid;
317. 2-(3-chlorophenyl)-3-(1H-pyrrolo[2,3-b]pyridin-3-yl)-2-propenoic acid;
318. 2-(3-methoxyphenyl)-3-(1H-pyrrolo[2,3-b]pyridin-3-yl)-2-propenoic acid;
319. 2-(3-bromophenyl)-3-(1H-pyrrolo[2,3-b]pyridin-3-yl)-2-propenoic acid;
320. 2-(1,3-benzodioxol-5-yl)-3-(1H-pyrrolo[2,3-b]pyridin-3-yl)-2-propenoic acid;
321. 2-(3,5-dimethoxyphenyl)-3-(1H-pyrrolo[2,3-b]pyridin-3-yl)-2-propenoic acid;
322. 2-(3-fluorophenyl)-3-(1H-pyrrolo[2,3-b]pyridin-3-yl)-2-propenoic acid;
323. 2-(4-butoxyphenyl)-3-(1H-pyrrolo[2,3-b]pyridin-3-yl)-2-propenoic acid;
324. 2-(3-chloro-4-hydroxyphenyl)-3-(1H-pyrrolo[2,3-b]pyridin-3-yl)-2-propenoic acid;
325. 2-[4-(methylsulfonyl)phenyl]-3-(1H-pyrrolo[2,3-b]pyridin-3-yl)-2-propenoic acid;
326. 2-(4-ethoxyphenyl)-3-(1H-pyrrolo[2,3-b]pyridin-3-yl)-2-propenoic acid;
327. 2-(3-methylphenyl)-3-(1H-pyrrolo[2,3-b]pyridin-3-yl)-2-propenoic acid;
328. 2-(2-methylphenyl)-3-(1H-pyrrolo[2,3-b]pyridin-3-yl)-2-propenoic acid;
329. 2-(3,4-dihydroxyphenyl)-3-(1H-pyrrolo[2,3-b]pyridin-3-yl)-2-propenoic acid;
330. 3-(1H-pyrrolo[2,3-b]pyridin-3-yl)-2-(2-thienyl)-2-propenoic acid;
331. 2-(2-bromophenyl)-3-(1H-pyrrolo[2,3-b]pyridin-3-yl)-2-propenoic acid;
332. 2-(2-fluorophenyl)-3-(1H-pyrrolo[2,3-b]pyridin-3-yl)-2-propenoic acid;
333. 2-(2-chlorophenyl)-3-(1H-pyrrolo[2,3-b]pyridin-3-yl)-2-propenoic acid;
334. 2-(2,4-dichlorophenyl)-3-(1H-pyrrolo[2,3-b]pyridin-3-yl)-2-propenoic acid;
335. 2-(2-chloro-6-fluorophenyl)-3-(1H-pyrrolo[2,3-b]pyridin-3-yl)-2-propenoic acid;
336. 2-(2,6-dichlorophenyl)-3-(1H-pyrrolo[2,3-b]pyridin-3-yl)-2-propenoic acid;
337. 2-(2,5-dimethoxyphenyl)-3-(1H-pyrrolo[2,3-b]pyridin-3-yl)-2-propenoic acid;
338. 2-(3,4-dichlorophenyl)-3-(1H-pyrrolo[2,3-b]pyridin-3-yl)-2-propenoic acid;
339. 3-(1H-pyrrolo[2,3-b]pyridin-3-yl)-2-(3,4,5-trimethoxyphenyl)-2-propenoic acid;
340. 3-(1H-pyrrolo[2,3-b]pyridin-3-yl)-2-[3-(trifluoromethyl)phenyl]-2-propenoic acid;
341. 3-(1H-pyrrolo[2,3-b]pyridin-3-yl)-2-[4-(trifluoromethyl)phenyl]-2-propenoic acid;
342. 2-[3,5-bis(trifluoromethyl)phenyl]-3-(1H-pyrrolo[2,3-b]pyridin-3-yl)-2-propenoic acid;
343. 2-(2,4-difluorophenyl)-3-(1H-pyrrolo[2,3-b]pyridin-3-yl)-2-propenoic acid;
344. 2-(2,5-difluorophenyl)-3-(1H-pyrrolo[2,3-b]pyridin-3-yl)-2-propenoic acid;
345. 2-(3,4-difluorophenyl)-3-(1H-pyrrolo[2,3-b]pyridin-3-yl)-2-propenoic acid;
346. 2-(3,5-difluorophenyl)-3-(1H-pyrrolo[2,3-b]pyridin-3-yl)-2-propenoic acid;
347. 2-[4-(benzyloxy)-3-methoxyphenyl]-3-(1H-pyrrolo[2,3-b]pyridin-3-yl)-2-propenoic acid;
348. 3-(1H-pyrrolo[2,3-b]pyridin-3-yl)-2-(3-thienyl)-2-propenoic acid;
349. 2-(5-methoxy-1H-indol-3-yl)-3-(1H-pyrrolo[2,3-b]pyridin-3-yl)-2-propenoic acid;
350. 2-(1-naphthyl)-3-(1H-pyrrolo[2,3-b]pyridin-3-yl)-2-propenoic acid;
351. 2-(3-methyl-1-benzothien-2-yl)-3-(1H-pyrrolo[2,3-b]pyridin-3-yl)-2-propenoic acid;
352. 2-(3,4-dimethoxyphenyl)-3-(1H-pyrrolo[2,3-b]pyridin-3-yl)-2-propenoic acid;
353. 2-(4-bromophenyl)-3-(1H-pyrrolo[2,3-b]pyridin-3-yl)-2-propenoic acid;
354. 2-[4-(acetylamino)phenyl]-3-(1H-pyrrolo[2,3-b]pyridin-3-yl)-2-propenoic acid;
355. 2-[4-amino-phenyl]-3-(1H-pyrrolo[2,3-b]pyridin-3-yl)-2-propenoic acid;
356. 2-(5-bromo-1H-indol-3-yl)-3-(1H-pyrrolo[2,3-b]pyridin-3-yl)-2-propenoic acid;
357. 2-(1-methyl-1H-indol-3-yl)-3-(1H-pyrrolo[2,3-b]pyridin-3-yl)-2-propenoic acid;
358. 2-(4-fluorophenyl)-3-(1H-pyrrolo[2,3-b]pyridin-3-yl)-2-propenoic acid;
359. 2-[2,5-bis(trifluoromethyl)phenyl]-3-(1H-pyrrolo[2,3-b]pyridin-3-yl)-2-propenoic acid;
360. 2-(2,3,5-difluorophenyl)-3-(1H-pyrrolo[2,3-b]pyridin-3-yl)-2-propenoic acid;
361. 2-[5-(benzyloxy)-1H-indol-3-yl]-3-(1H-pyrrolo[2,3-b]pyridin-3-yl)-2-propenoic acid;

362. 2-(2-amino-1,3-thiazol-4-yl)-3-(1H-pyrrolo[2,3-b]pyridin-3-yl)-2-propenoic acid;
363. 2-mesityl-3-(1H-pyrrolo[2,3-b]pyridin-3-yl)-2-propenoic acid;
364. 3-(1H-pyrrolo[2,3-b]pyridin-3-yl)-2-[4-(trifluoromethoxy)phenyl]-2-propenoic acid;
365. 2-(3,5-ditert-butyl-4-hydroxyphenyl)-3-(1H-pyrrolo[2,3-b]pyridin-3-yl)-2-propenoic acid;
366. 2-[4-(2-amino-2-oxoethoxy)phenyl]-3-(1H-pyrrolo[2,3-b]pyridin-3-yl)-2-propenoic acid;
367. 2-{4-[2-oxo-2-(1-pyrrolidinyl)ethoxy]phenyl}-3-(1H-pyrrolo[2,3-b]pyridin-3-yl)-2-propenoic acid;
368. 2-(3-hydroxy-5-methoxy-2-propylphenyl)-3-(1H-pyrrolo[2,3-b]pyridin-3-yl)-2-propenoic acid;
369. 2-(4-phenoxyphenyl)-3-(1H-pyrrolo[2,3-b]pyridin-3-yl)-2-propenoic acid;
370. 2-[2-(4-chlorophenyl)-1,3-thiazol-4-yl]-3-(1H-pyrrolo[2,3-b]pyridin-3-yl)-2-propenoic acid;
371. 2-{3-[(methylsulfonyl)amino]phenyl}-3-(1H-pyrrolo[2,3-b]pyridin-3-yl)-2-propenoic acid;
372. 2-{4-[(methylsulfonyl)amino]phenyl}-3-(1H-pyrrolo[2,3-b]pyridin-3-yl)-2-propenoic acid;
373. 2-[4-(1-pyrrolidinyl)phenyl]-3-(1H-pyrrolo[2,3-b]pyridin-3-yl)-2-propenoic acid;
374. 2-{4-[(2-amino-2-oxoethyl)amino]phenyl}-3-(1H-pyrrolo[2,3-b]pyridin-3-yl)-2-propenoic acid;
375. 2-(4-chlorophenyl)-3-(1H-pyrrolo[2,3-b]pyridin-3-yl)-2-propenamide;
376. 3-(1H-pyrrolo[2,3-b]pyridin-3-yl)-2-(4-tolyl)-2-propenamide;
377. 3-(1H-pyrrolo[2,3-b]pyridin-3-yl)-2-[2-(trifluoromethyl)phenyl]-2-propenamide;
378. 2-(1-acetyl-1H-indol-3-yl)-3-(1H-pyrrolo[2,3-b]pyridin-3-yl)-2-propenamide;
379. 2-(1H-indol-3-yl)-3-(1H-pyrrolo[2,3-b]pyridin-3-yl)-2-propenamide;
380. 2-(3-fluoro-4-hydroxyphenyl)-3-(1H-pyrrolo[2,3-b]pyridin-3-yl)-2-propenamide;
381. 2-(2,3-dihydro-1H-inden-5-yl)-3-(1H-pyrrolo[2,3-b]pyridin-3-yl)-2-propenamide;
382. 2-(3-pyridinyl)-3-(1H-pyrrolo[2,3-b]pyridin-3-yl)-2-propenamide;
383. 2-(4-hydroxyphenyl)-3-(1H-pyrrolo[2,3-b]pyridin-3-yl)-2-propenamide;
384. 2-(4-methoxyphenyl)-3-(1H-pyrrolo[2,3-b]pyridin-3-yl)-2-propenamide;
385. 2-(2-hydroxyphenyl)-3-(1H-pyrrolo[2,3-b]pyridin-3-yl)-2-propenamide;
386. 2-(2-methoxyphenyl)-3-(1H-pyrrolo[2,3-b]pyridin-3-yl)-2-propenamide;
387. 2-[1,1'-biphenyl]-4-yl-3-(1H-pyrrolo[2,3-b]pyridin-3yl)-2-propenamide;
388. 2-(4-hydroxy-5-isopropyl-2-methylphenyl)-3-(1H-pyrrolo[2,3-b]pyridin-3-yl)-2-propenamide;
389. 2-(4-hydroxy-3-methoxyphenyl)-3-(1H-pyrrolo[2,3-b]pyridin-3-yl)-2-propenamide;
390. 2-(3-chlorophenyl)-3-(1H-pyrrolo[2,3-b]pyridin-3-yl)-2-propenamide;
391. 2-(3-methoxyphenyl)-3-(1H-pyrrolo[2,3-b]pyridin-3-yl)-2-propenamide;
392. 2-(3-bromophenyl)-3-(1H-pyrrolo[2,3-b]pyridin-3-yl)-2-propenamide;
393. 2-(1,3-benzodioxol-5-yl)-3-(1H-pyrrolo[2,3-b]pyridin-3-yl)-2-propenamide;
394. 2-(3,5-dimethoxyphenyl)-3-(1H-pyrrolo[2,3-b]pyridin-3-yl)-2-propenamide;
395. 2-(3-fluorophenyl)-3-(1H-pyrrolo[2,3-b]pyridin-3-yl)-2-propenamide;
396. 2-(4-butoxyphenyl)-3-(1H-pyrrolo[2,3-b]pyridin-3-yl)-2-propenamide;
397. 2-(3-chloro-4-hydroxyphenyl)-3-(1H-pyrrolo[2,3-b]pyridin-3-yl)-2-propenamide;
398. 2-[4-(methylsulfonyl)phenyl]-3-(1H-pyrrolo[2,3-b]pyridin-3-yl)-2-propenamide;
399. 2-(4-ethoxyphenyl)-3-(1H-pyrrolo[2,3-b]pyridin-3-yl)-2-propenamide;
400. 2-(3-methylphenyl)-3-(1H-pyrrolo[2,3-b]pyridin-3-yl)-2-propenamide;
401. 2-(2-methylphenyl)-3-(1H-pyrrolo[2,3-b]pyridin-3-yl)-2-propenamide;
402. 2-(3,4-dihydroxyphenyl)-3-(1H-pyrrolo[2,3-b]pyridin-3-yl)-2-propenamide;
403. 3-(1H-pyrrolo[2,3-b]pyridin-3-yl)-2-(2-thienyl)-2-propenamide;
404. 2-(2-bromophenyl)-3-(1H-pyrrolo[2,3-b]pyridin-3-yl)-2-propenamide;
405. 2-(2-fluorophenyl)-3-(1H-pyrrolo[2,3-b]pyridin-3-yl)-2-propenamide;
406. 2-(2-chlorophenyl)-3-(1H-pyrrolo[2,3-b]pyridin-3-yl)-2-propenamide;
407. 2-(2,4-dichlorophenyl)-3-(1H-pyrrolo[2,3-b]pyridin-3-yl)-2-propenamide;
408. 2-(2-chloro-6-fluorophenyl)-3-(1H-pyrrolo[2,3-b]pyridin-3-yl)-2-propenamide;
409. 2-(2,6-dichlorophenyl)-3-(1H-pyrrolo[2,3-b]pyridin-3-yl)-2-propenamide;
410. 2-(2,5-dimethoxyphenyl)-3-(1H-pyrrolo[2,3-b]pyridin-3-yl)-2-propenamide;
411. 2-(3,4-dichlorophenyl)-3-(1H-pyrrolo[2,3-b]pyridin-3-yl)-2-propenamide;
412. 3-(1H-pyrrolo[2,3-b]pyridin-3-yl)-2-(3,4,5-trimethoxyphenyl)-2-propenamide;
413. 3-(1H-pyrrolo[2,3-b]pyridin-3-yl)-2-[3-(trifluoromethyl)phenyl]-2-propenamide;
414. 3-(1H-pyrrolo[2,3-b]pyridin-3-yl)-2-[4-(trifluoromethyl)phenyl]-2-propenamide;
415. 2-[3,5-bis(trifluoromethyl)phenyl]-3-(1H-pyrrolo[2,3-b]pyridin-3-yl)-2-propenamide;
416. 2-(2,4-difluorophenyl)-3-(1H-pyrrolo[2,3-b]pyridin-3-yl)-2-propenamide;
417. 2-(2,5-difluorophenyl)-3-(1H-pyrrolo[2,3-b]pyridin-3-yl)-2-propenamide;
418. 2-(3,4-difluorophenyl)-3-(1H-pyrrolo[2,3-b]pyridin-3-yl)-2-propenamide;
419. 2-(3,5-difluorophenyl)-3-(1H-pyrrolo[2,3-b]pyridin-3-yl)-2-propenamide;
420. 2-[4-(benzyloxy)-3-methoxyphenyl]-3-(1H-pyrrolo[2,3-b]pyridin-3-yl)-2-propenamide;
421. 3-(1H-pyrrolo[2,3-b]pyridin-3-yl)-2-(3-thienyl)-2-propenamide;
422. 2-(5-methoxy-1H-indol-3-yl)-3-(1H-pyrrolo[2,3-b]pyridin-3-yl)-2-propenamide;
423. 2-(1-naphthyl)-3-(1H-pyrrolo[2,3-b]pyridin-3-yl)-2-propenamide;
424. 2-(3-methyl-1-benzothien-2-yl)-3-(1H-pyrrolo[2,3-b]pyridin-3-yl)-2-propenamide;
425. 2-(3,4-dimethoxyphenyl)-3-(1H-pyrrolo[2,3-b]pyridin-3-yl)-2-propenamide;
426. 2-(4-bromophenyl)-3-(1H-pyrrolo[2,3-b]pyridin-3-yl)-2-propenamide;
427. 2-[4-(acetylamino)phenyl]-3-(1H-pyrrolo[2,3-b]pyridin-3-yl)-2-propenamide;
428. 2-[4-amino-phenyl]-3-(1H-pyrrolo[2,3-b]pyridin-3-yl)-2-propenamide;
429. 2-(5-bromo-1H-indol-3-yl)-3-(1H-pyrrolo[2,3-b]pyridin-3-yl)-2-propenamide;

430. 2-(1-methyl-1H-indol-3-yl)-3-(1H-pyrrolo[2,3-b]pyridin-3-yl)-2-propenamide;
431. 2-(4-fluorophenyl)-3-(1H-pyrrolo[2,3-b]pyridin-3-yl)-2-propenamide;
432. 2-[2,5-bis(trifluoromethyl)phenyl]-3-(1H-pyrrolo[2,3-b]pyridin-3-yl)-2-propenamide;
433. 2-(2,3,5-difluorophenyl)-3-(1H-pyrrolo[2,3-b]pyridin-3-yl)-2-propenamide;
434. 2-[5-(benzyloxy)-1H-indol-3-yl]-3-(1H-pyrrolo[2,3-b]pyridin-3-yl)-2-propenamide;
435. 2-(2-amino-1,3-thiazol-4-yl)-3-(1H-pyrrolo[2,3-b]pyridin-3-yl)-2-propenamide;
436. 2-mesityl-3-(1H-pyrrolo[2,3-b]pyridin-3-yl)-2-propenamide;
437. 3-(1H-pyrrolo[2,3-b]pyridin-3-yl)-2-[4-(trifluoromethoxy)phenyl]-2-propenamide;
438. 2-(3,5-ditert-butyl-4-hydroxyphenyl)-3-(1H-pyrrolo[2,3-b]pyridin-3-yl)-2-propenamide;
439. 2-[4-(2-amino-2-oxoethoxy)phenyl]-3-(1H-pyrrolo[2,3-b]pyridin-3-yl)-2-propenamide;
440. 2-{4-[2-oxo-2-(1-pyrrolidinyl)ethoxy]phenyl}-3-(1H-pyrrolo[2,3-b]pyridin-3-yl)-2-propenamide;
441. 2-(3-hydroxy-5-methoxy-2-propylphenyl)-3-(1H-pyrrolo[2,3-b]pyridin-3-yl)-2-propenamide;
442. 2-(4-phenoxyphenyl)-3-(1H-pyrrolo[2,3-b]pyridin-3-yl)-2-propenamide;
443. 2-[2-(4-chlorophenyl)-1,3-thiazol-4-yl]-3-(1H-pyrrolo[2,3-b]pyridin-3-yl)-2-propenamide;
444. 2-{3-[(methylsulfonyl)amino]phenyl}-3-(1H-pyrrolo[2,3-b]pyridin-3-yl)-2-propenamide;
445. 2-{4-[(methylsulfonyl)amino]phenyl}-3-(1H-pyrrolo[2,3-b]pyridin-3-yl)-2-propenamide;
446. 2-[4-(1-pyrrolidinyl)phenyl]-3-(1H-pyrrolo[2,3-b]pyridin-3-yl)-2-propenamide;
447. 2-{4-[(2-amino-2-oxoethyl)amino]phenyl}-3-(1H-pyrrolo[2,3-b]pyridin-3-yl)-2-propenamide;
448. N-benzyl-2-phenyl-3-(1H-pyrrolo[2,3-b]pyridin-3-yl)-2-propenamide;
449. N-(4-methoxyphenyl)-2-phenyl-3-(1H-pyrrolo[2,3-b]pyridin-3-yl)-2-propenamide;
450. 1-(4-morpholinyl)-2-phenyl-3-(1H-pyrrolo[2,3-b]pyridin-3-yl)-2-propen-1-one
451. N-(4-chlorophenyl)-2-phenyl-3-(1H-pyrrolo[2,3-b]pyridin-3-yl)-2-propenamide;
452. N,N-dimethyl-2-phenyl-3-(1H-pyrrolo[2,3-b]pyridin-3-yl)-2-propenamide;
453. N-isopropyl-2-phenyl-3-(1H-pyrrolo[2,3-b]pyridin-3-yl)-2-propenamide;
454. 2-phenyl-1-(1-piperidinyl)-3-(1H-pyrrolo[2,3-b]pyridin-3-yl)-2-propen-1-one
455. N-[(3-aminomethyl)-pyridin]-2-phenyl-3-(1H-pyrrolo[2,3-b]pyridin-3-yl)-2-propenamide;
456. N-benzyl-N-methyl-2-phenyl-3-(1H-pyrrolo[2,3-b]pyridin-3-yl)-2-propenamide;
457. N-(1H-indazol-6-yl)-2-phenyl-3-(1H-pyrrolo[2,3-b]pyridin-3-yl)-2-propenamide;
458. N-(4-methoxybenzyl)-2-phenyl-3-(1H-pyrrolo[2,3-b]pyridin-3-yl)-2-propenamide;
459. N-(4-chlorobenzyl)-2-phenyl-3-(1H-pyrrolo[2,3-b]pyridin-3-yl)-2-propenamide;
460. N-[(1-ethyl-2-pyrrolidinyl)methyl]-2-phenyl-3-(1H-pyrrolo[2,3-b]pyridin-3-yl)-2-propenamide;
461. N-furfuryl-2-phenyl-3-(1H-pyrrolo[2,3-b]pyridin-3-yl)-2-propenamide;
462. N-(4-hydroxypiperidin)-2-phenyl-3-(1H-pyrrolo[2,3-b]pyridin-3-yl)-2-propenamide;
463. N-(3-hydroxypiperidin)-2-phenyl-3-(1H-pyrrolo[2,3-b]pyridin-3-yl)-2-propenamide;
464. N-(3-methoxyphenyl)-2-phenyl-3-(1H-pyrrolo[2,3-b]pyridin-3-yl)-2-propenamide;
465. N,2-diphenyl-3-(1H-pyrrolo[2,3-b]pyridin-3-yl)-2-propenamide;
466. 3-[3-(4-methyl-1-piperazinyl)-3-oxo-2-phenyl-1-propenyl]-1H-pyrrolo[2,3-b]pyridine
467. N-[4-(dimethylamino)phenyl]-2-phenyl-3-(1H-pyrrolo[2,3-b]pyridin-3-yl)-2-propenamide;
468. N-(3-chlorophenyl)-2-phenyl-3-(1H-pyrrolo[2,3-b]pyridin-3-yl)-2-propenamide;
469. N,N-diethyl-2-phenyl-3-(1H-pyrrolo[2,3-b]pyridin-3-yl)-2-propenamide;
470. 3-[3-(4-benzyl-1-piperazinyl)-3-oxo-2-phenyl-1-propenyl]-1H-pyrrolo[2,3-b]pyridine
471. 2-[2-phenyl-3-(1H-pyrrolo[2,3-b]pyridin-3-yl)-2-propenoyl]-1,2,3,4-tetrahydroisoquinoline
472. N-(tert-butoxy)-2-phenyl-3-(1H-pyrrolo[2,3-b]pyridin-3-yl)-2-propenamide;
473. N-hydroxy-2-phenyl-3-(1H-pyrrolo[2,3-b]pyridin-3-yl)-2-propenamide;
474. N-methyl-2-phenyl-3-(1H-pyrrolo[2,3-b]pyridin-3-yl)-2-propenamide;
475. 3-{6-[(2-naphthylacetyl)amino]-1H-pyrrolo[2,3-b]pyridin-3-yl}-2-phenyl-2-propenamide;
476. 2-(3-chloro-4-hydroxyphenyl)-3-{6-[(2-naphthylacetyl)amino]-1H-pyrrolo[2,3-b]pyridin-3-yl}-2-propenamide;
477. 3-{6-[(1-naphthylacetyl)amino]-1H-pyrrolo[2,3-b]pyridin-3-yl}-2-phenyl-2-propenamide;
478. 2-(3-chloro-4-hydroxyphenyl)-3-{6-[(1-naphthylacetyl)amino]-1H-pyrrolo[2,3-b]pyridin-3-yl}-2-propenamide;
479. 2-phenyl-3-[6-({[4-(2-thienyl)phenyl]acetyl}amino)-1H-pyrrolo[2,3-b]pyridin-3-yl]-2-propenamide;
480. 2-(3-chloro-4-hydroxyphenyl)-3-[6-({[4-(2-thienyl)phenyl]acetyl}amino)-1H-pyrrolo[2,3-b]pyridin-3-yl]-2-propenamide;
481. 2-phenyl-3-[6-({[4-(3-thienyl)phenyl]acetyl}amino)-1H-pyrrolo[2,3-b]pyridin-3-yl]-2-propenamide;
482. 2-(3-chloro-4-hydroxyphenyl)-3-[6-({[4-(3-thienyl)phenyl]acetyl}amino)-1H-pyrrolo[2,3-b]pyridin-3-yl]-2-propenamide;
483. 3-(6-{[(3',4'-difluoro[1,1'-biphenyl]-4-yl)acetyl]amino}-1H-pyrrolo[2,3-b]pyridin-3-yl)-2-phenyl-2-propenamide;
484. 2-(3-chloro-4-hydroxyphenyl)-3-(6-{[(3',4'-difluoro[1,1'-biphenyl]-4-yl)acetyl]amino}-1H-pyrrolo[2,3-b]pyridin-3-yl)-2-propenamide;
485. 3-(6-{[(5'-fluoro-2'-methoxy[1,1'-biphenyl]-4-yl)acetyl]amino}-1H-pyrrolo[2,3-b]pyridin-3-yl)-2-phenyl-2-propenamide;
486. 2-(3-chloro-4-hydroxyphenyl)-3-(6-{[(5'-fluoro-2'-methoxy[1,1'-biphenyl]-4-yl)acetyl]amino}-1H-pyrrolo[2,3-b]pyridin-3-yl)-2-propenamide;
487. 3-(6-{[(2',5'-difluoro[1,1'-biphenyl]-4-yl)acetyl]amino}-1H-pyrrolo[2,3-b]pyridin-3-yl)-2-phenyl-2-propenamide;
488. 2-(3-chloro-4-hydroxyphenyl)-3-(6-{[(2',5'-difluoro[1,1'-biphenyl]-4-yl)acetyl]amino}-1H-pyrrolo[2,3-b]pyridin-3-yl)-2-propenamide;
489. 3-(6-{[(3'-ethoxy[1,1'-biphenyl]-4-yl)acetyl]amino}-1H-pyrrolo[2,3-b]pyridin-3-yl)-2-phenyl-2-propenamide;
490. 2-(3-chloro-4-hydroxyphenyl)-3-(6-{[(3'-ethoxy[1,1'-biphenyl]-4-yl)acetyl]amino}-1H-pyrrolo[2,3-b]pyridin-3-yl)-2-propenamide.

Another object of the present invention is a process for preparing the compounds of formula (I) which is carried out according to methods well known to the person skilled in the art, for instance by applying known reactions to suitable intermediate substrates.

In particular, the compounds of formula (I) object of the present invention can be obtained, for instance, by a process comprising reacting a compound of formula (II)

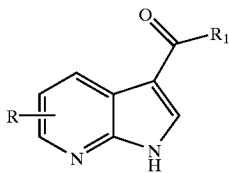

(II)

wherein R and $R_1$ are as above indicated, with a compound of formula (III)

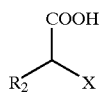

(III)

wherein $R_2$ is as above indicated and X represents a hydrogen atom, a —COOH carboxy group or a derivative thereof such as —COOR$_4$ or —CONR$_4$R$_5$, wherein $R_4$ and $R_5$ are as above indicated, thus obtaining a compound of formula (I) wherein R, $R_1$ and $R_2$ are as defined above and $R_3$ is a hydrogen atom, a —COOH carboxy group or a derivative thereof such as —COOR$_4$ or —CONR$_4$R$_5$, wherein $R_4$ and $R_5$ are as above indicated; and, if desired, converting the said compound of formula (I) into another compound of formula (I) and/or into a salt thereof.

The above process is an analogy process which can be carried out according to well known methods.

As an example, the preparation of a compound of formula (I) wherein $R_3$ is a COOH carboxy group, according to the process object of the invention, is carried out according to conventional techniques by reacting the above compound of formula (II) with an arylacetic acid derivative of formula (III) wherein X is hydrogen, for instance in acetic anhydride in the presence of a suitable base such as triethylamine, pyridine or diisopropylethylamine, at a temperature ranging from about 60° C. to 140° C. for a suitable time, i.e. from about 1 hour to several hours.

The preparation of a compound of formula (I) wherein $R_3$ is hydrogen, according to the process object of the invention, is carried out according to conventional techniques by reacting the above compound of formula (II) with a malonic acid derivative of formula (III) wherein X is a —COOH carboxy group, in the presence of a suitable base such as pyridine, piperidine or mixtures thereof, at a temperature ranging from about 60° C. to about 140° C. and for a suitable time varying from about 3 hours to several hours.

Likewise, the preparation of a compound of formula (I) wherein $R_3$ is a carboxy derivative other than COOH, such as —CONR$_4$R$_5$ or —COOR$_4$, is carried out according to conventional techniques by reacting a compound of formula (II) with a derivative of formula (III) wherein X is —CONR$_4$R$_5$ or —COOR$_4$.

Also the optional conversion of a compound of formula (I) into another compound of formula (I) can be carried out according to known methods.

As an example, compounds of formula (I) wherein $R_3$ is a group —CONR$_4$R$_5$ can be also obtained from the corresponding compounds of formula (I) wherein $R_3$ is COOH, by reaction with a compound of formula $R_4$—NH—$R_5$ (IV)

wherein $R_4$ and $R_5$ are as defined above.

The reaction between a compound of formula (IV) and a carboxylic acid of formula (I) can be carried out in the presence of a coupling agent such as, for instance, carbodiimide, i.e. 1,3-dicyclohexylcarbodiimide, 1,3-diisopropylcarbodiimide, O-(benzotriazol-1-yl)-N,N,N',N'-tetramethyluronium tetrafluoborate, 1-(3-dimethyl-aminopropyl)-3-ethylcarbodiimide, N-cyclohexylcar-bodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −20° C. to reflux for a suitable time, i.e. from about 30 min. to about 96 hours, optionally in the presence of a suitable catalyst such as 4-dimethylaminopyridine or in the presence of a further coupling reagent such as N-hydroxybenzotriazole.

N-hydroxybenzotriazole ammonium salt can be conveniently used as a reactant in the preparation of the compounds of formula (I) as above indicated wherein $R_3$ is —CONR$_4$R$_5$, $R_4$ and $R_5$ being both hydrogen atoms.

The reaction between a compound of formula (IV) and a carboxylic acid of formula (I) can be also carried out, for example, by a mixed anhydride method, using an alkyl chloroformate, such as ethyl, iso-butyl, or iso-propyl chloroformate, in the presence of a tertiary base, such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

Compounds of formula (I) wherein $R_3$ is a —COOR$_4$ group can be obtained from the corresponding compounds of formula (I) wherein $R_3$ is COOH by reaction with a compound of formula $R_4$—OH (V)

wherein $R_4$ is as defined above.

The reaction between a compound of formula (V) and a carboxylic acid of formula (I) is an is an analogy process which can be carried out according to well known methods.

Compounds of formula (I) wherein $R_3$ is —COOR$_4$ can, in turn, be converted into compounds of formula (I) wherein $R_3$ is —CONR$_4$R$_5$ by reaction with a compound of formula (IV) in a suitable solvent such as 1,4-dioxane, tetrahydrofuran, N,N'-dimethylformamide at a temperature ranging from about 20° C. to 80° C. for a suitable time, i.e. from about 10 hour to about 96 hours.

Compounds of formula (I) wherein $R_3$ is —CONHOR$_4$ can be obtained from the corresponding compounds of formula (I) wherein $R_3$ is COOH by reaction with a compound of formula $NH_2$—OR$_4$ (VI)

wherein $R_4$ is as defined above.

The reaction between a compound of formula (VI) and a carboxylic acid of formula (I) can be carried out in the presence of a coupling agent such as, for instance, carbodiimide, i.e. 1,3-dicyclohexylcarbodiimide, 1,3-diisopropylcarbodiimide, O-(benzotriazol-1-yl) -N,N,N',N'-tetramethyluronium tetrafluoborate, 1-(3-dimethyl-aminopropyl)-3-ethylcarbodiimide, N-cyclohexylcar-bodiimide-N'-propyloxymethyl polystyrene or N-cyclohexylcarbodiimide-N'-methyl polystyrene in a suitable solvent such as, for instance, dichloromethane, chloroform, tetrahydrofuran, diethyl ether, 1,4-dioxane, acetonitrile, toluene, or N,N-dimethylformamide at a temperature ranging from about −20° C. to reflux for a suitable time, i.e. from about 30 min. to about 96 hours, optionally in the presence of a suitable catalyst such as 4-dimethylaminopyridine or in the presence of a further coupling reagent such as N-hydroxybenzotriazole.

The intermediate compounds of formula (II) wherein $R_1$ is as above indicated and R is other than hydrogen are novel and, hence, represent a further object of the present invention.

The compounds of formula (II) wherein R is as described above and $R_1$ is hydrogen can be obtained by reacting the compounds of formula (VII) wherein R is as described above

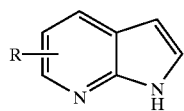
(VII)

with a formylating agent such as, for instance, hexamethylenetetramine in a solvent such as acetic acid at 33% or phosphorus oxychloride in dimethylformamide, at a temperature ranging from room temperature to reflux.

The compounds of formula (II) wherein R is as described above and $R_1$ is alkyl can be prepared by a process comprising:

a) reacting the compounds of formula (VII) wherein R is as described above with methylmagnesium iodide, thus obtaining the compounds of formula (VIII)

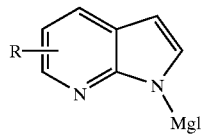
(VIII)

b) reacting them with the compounds of formula (IX)

$R_1COCl$      (IX)

wherein $R_1$ is an alkyl group optionally substituted as above defined, thus obtaining the compounds of formula (X)

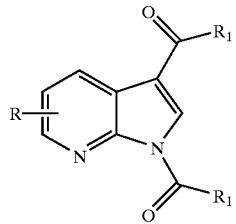
(X)

wherein R and $R_1$ are as defined above; and c) hydrolyzing the compounds of formula (X) in the presence of a base.

The above compounds of formula (VIII) can be prepared in a suitable solvent such as, for instance, diethylether, dioxane, tetrahydrofuran, at a temperature ranging from 0° C. to reflux.

The above compounds of formula (X), in their turn, can be prepared in a suitable solvent such as diethylether, dioxane, tetrahydrofuran, at a temperature ranging from 0° C. to reflux.

The hydrolysis according to step (c) can be then carried out with a suitable base such as sodium hydrate, potassium hydrate, potassium carbonate in a suitable solvent, for instance mixtures of methanol/water, ethanol/water, tetrahydrofurane/water, at a temperature ranging from room temperature to reflux.

The compounds of formula (VII) where R is amino can be prepared according to well known methods reported in the literature. [See, for a reference, Bull. Chem. Soc. Jpn., 65, 2992–2997 (1992); J. AM. Chem. Soc., 81, 743–745 (1959); J. Med. Chem., 25, 1258–1261 (1982)].

The compounds of formula (VII) where R is hydroxy, cyano or halogen can be obtained by conventional methods known in the art, through nucleophylic substitution of the corresponding diazonium salts.

The compounds of formula (VII) where R is —$OCOR_4$ and $R_4$ is as described above can be obtained according to well known methods from the corresponding compounds of formula (VII) wherein R is hydroxy, by reaction with the compounds of formula (XI)

$R_4$—COOH      (XI)

wherein $R_4$ is as described above.

The compound of formula (VII) where R is aminomethyl can be obtained by reduction of the corresponding cyano derivative, for instance by using hydrogen in the presence of a suitable catalyst such as palladium on charcoal, in a solvent such as methanol or ethanol at room temperature.

The compounds of formula (VII) wherein R is —$(CH_2)_n NHR_4$, n is either 0 or 1 and $R_4$ is alkyl, can be obtained from the compounds of formula (VII) wherein R is —$(CH_2)_n NH_2$ by reaction with a proper carbonylic compound, in presence of a reductive agent such as sodiumcyanoborohydride at room temperature and in a solvent such as methanol or ethanol.

The compounds of formula (VII) wherein R is $NHR_4$ and $R_4$ is aryl, hence also comprising heteroaryl, can be obtained from the compounds of formula (VII) where R is halogen by nucleophylic substitution with the corresponding arylamino derivative, in solvents such as dioxane, tetrahydrofuran, toluene, N,N'-dimethylformamide eventually with a base such as potassium carbonate, triethylamine, N,N-diisopropylethylamine at a temperature ranging from room temperature to reflux.

The compounds of formula (VII) where R is —$(CH_2)_n NHR_4$, n is 1 and $R_4$ is aryl, as above, can be obtained from the compounds of formula (VII) where R is cyano according to well-known methods requiring the transformation of the cyano group into a chloromethyl group followed by nucleophylic substitution with the corresponding arylamino derivative.

The compounds of formula (VII) wherein R is —$(CH_2)_n NHCOR_4$ and n is either 0 or 1 can be obtained by reacting the corresponding compounds (VII) wherein R is —$(CH_2)_n NH_2$ with the compounds of formula (XI) wherein $R_4$ is as described above, according to well known methods.

The compounds of formula (VII) wherein R is —$(CH_2)_n NHCONH_2$ wherein n is either 0 or 1 can be obtained by reacting the compounds of formula (VII) wherein R is —$(CH_2)_n NH_2$ with sodium cyanate or potassium cyanate in mixtures of acetic acid-water at room temperature.

The compounds of formula (VII) where R is —$(CH_2)_n NHCONR_4R_5$ wherein n is either 0 or 1 and $R_4$ and $R_5$ are as defined above, can be obtained by a process comprising:

a) reacting the compounds of formula (VII) wherein R is —(CH$_2$)$_n$NH$_2$ with 4-nitrophenylchloroformate, thus obtaining the compounds of formula (XII) wherein n is either 0 or 1:

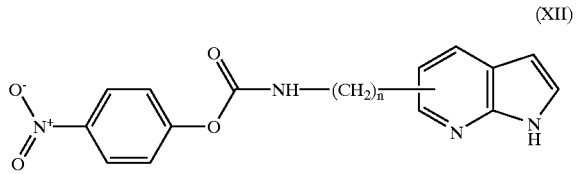

(XII)

b) reacting the above compounds (XII) with the compounds of formula (XIII)

R$_4$R$_5$NH       (XIII)

wherein R$_4$ and R$_5$ are as defined above.

The compounds of formula (XII) can be obtained as above indicated in the presence of a tertiary base such as triethylamine, N-methylmorpholine, N,N-diisopropylethylamine or pyridine in a suitable solvent such as toluene, dichloromethane, chloroform, diethylether, tetrahydrofuran, acetonitrile, dioxane or N,N-dimethylformamide, at a temperature ranging from about −20° C. to room temperature.

The reaction between a compound of formula (XII) and a compound of formula (XIII) can be carried out in a suitable solvent such as toluene, dichloromethane, chloroform, diethylether, tetrahydrofuran, acetonitrile, dioxane or N,N-dimethylformamide, at a temperature ranging from room temperature to reflux.

The compounds of formula (VII) where R is —(CH$_2$)$_n$NHCOOR$_4$ wherein n is either 0 or 1 and R$_4$ is as defined above, can be obtained by reacting the compounds of formula (VII) where R is —(CH$_2$)$_n$NH$_2$ with the compounds of formula (XIV):

ClCOOR$_4$       (XIV)

wherein R$_4$ is as defined above, in the presence of a tertiary base such as triethylamine, N-methylmorpholine, N,N-diisopropylethylamine or pyridine in a suitable solvent such as toluene, dichloromethane, chloroform, diethylether, tetrahydrofuran, acetonitrile, dioxane or N,N-dimethylformamide, at a temperature ranging from about −10° C. to room temperature.

The compounds of formula (VII) where R is —(CH$_2$)$_n$NHSO$_2$R$_4$ wherein n is either 0 or 1 and R$_4$ is as defined above, can be obtained by reacting the compounds of formula (VII) where R is —(CH$_2$)$_n$NH$_2$ with compounds of formula (XV):

ClSO$_2$R$_4$       (XV)

wherein R$_4$ is as defined above, in the presence of a tertiary base such as triethylamine, N-methylmorpholine, N,N-diisopropylethylamine or pyridine in a suitable solvent such as toluene, dichloromethane, chloroform, diethylether, tetrahydrofuran, acetonitrile, dioxane or N,N-dimethylformamide, at a temperature ranging from about −10° C. to room temperature.

It is clear to the person skilled in the art that if the compounds of formula (I), prepared according to the above process are obtained as an admixture of isomers, hence comprising stereoisomers or (E,Z) isomers, their separation into the single isomers of formula (I), carried out according to conventional techniques, is still within the scope of the present invention.

Likewise, any admixture of isomers of the compounds of formula (I) as well as the single isomers are within the scope of the present invention.

The conversion of the salt of a compound of formula (I) into the free compound or, alternatively, of the free compound into a salt of formula (I), both carried out according to well-known procedures in the art, is still within the scope of the invention.

Other optional conversions of a compound of formula (I) into another compound of formula (I) can be carried out according to known methods.

As an example, an alkylthio or an arylthio group may be converted into the corresponding alkylsulfonyl and arylsulfonyl group by reaction, for example, with m-chloroperbenzoic acid in a suitable solvent such as dichloromethane or chloroform, at a temperature varying between about −5° C. and room temperature.

When preparing the compounds of formula (I) according to the process object of the present invention, optional functional groups within both the starting materials or the intermediates thereof, which could give rise to unwanted side reactions, need to be properly protected according to conventional techniques.

Likewise, the conversion of these latter into the free deprotected compounds may be carried out according to known procedures.

The compounds of formula (III), (IV), (V), (VI), (IX), (XIII), (XIV), (XV), according to the process object of the present invention, are known compounds or can be obtained according to known methods.

The preparation of the compounds of formula (I), according to the process object of the invention, is preferably carried out in a serial manner according to combinatorial chemistry techniques well known to the man skilled in the art.

As an example, the compounds of formula (I) are prepared by reacting a given number of compounds of formula (II) in a suitable solvent with a given number of compounds of formula (III) in a suitable solvent using supporting reagents and, then, by separating the resultant compounds from the mixture.

Whenever appropriate, each of the above compounds of formula (I) wherein R$_3$ is a COOH group are transformed into compounds of formula (I) wherein R$_3$ is a —COOR$_4$, —CONR$_4$R$_5$ or CONHR$_4$ wherein R$_4$ and R$_5$ are as above indicated, by using supporting reagents.

Pharmacology

The compounds of formula (I) are active as cdk/cyclin inhibitors as they gave positive results when tested according to the following procedure.

The inhibiting activity of putative cdk/cyclin inhibitors and the potency of selected compounds was determined through a method of assay based on the use of the MultiScreen-PH 96 well plate (Millipore), in which a phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter.

Inhibition Assay of cdk2/Cyclin A Activity

Kinase reaction: 1.5 μM histone H1 substrate, 25 μM ATP (0.2 uCi P33g-ATP), 30 ng of baculovirus co-expressed cdk2/Cyclin A, 10 μM inhibitor in a final volume of 100 μl buffer (TRIS HCl 10 mM pH 7.5, MgCl2 10 mM, 7.5 mM DTT) were added to each well of a 96 U bottom well plate. After 10 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS Ca++/Mg++ free and filtered by MultiScreen filtration system.

Detection: filters were allowed to dry at 37° C., then 100 μl/well scintillant were added and 33P labelled histone H1 was detected by radioactivity counting in the Top-Count instrument.

Results: data were analysed and expressed as % inhibition referred to total activity of enzyme (=100%).

All compounds showing inhibition ≧50% were further analysed in order to study and define potency (IC50) as well as the kinetic-profile of inhibitor through Ki calculation.

IC50 determination: the protocol used was the same described above, where inhibitors were tested at different concentrations ranging from 0.0045 to 10 μM. Experimental data were analyzed by the computer program GraphPad Prizm using the four parameter logistic equation: y=bottom+(top-bottom)/(1+10^((logIC50-x)*slope)) where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 μM for ATP (containing proportionally diluted $P^{33}\gamma$-ATP) and 0.4, 0.8, 1.2, 2.4, 4.8 μM for histone were used in absence and presence of two different, properly chosen inhibitor concentrations.

Experimental data were analysed by the computer program "SigmaPlot" for Ki determination, using a random bireactant system equation:

$$v = \frac{V\max \frac{(A)(B)}{aKAKB}}{1 + \frac{(A)}{KA} + \frac{(B)}{KB} + \frac{(A)(B)}{aKAKB}}$$

where A=ATP and B=histone H1.

In addition the selected compounds have been characterized on a panel of ser/threo kinases strictly related to cell cycle (cdk2/cyclin E, cdk1/cyclin B1, cdk4/Cyclin D1), and for specificity on MAPK, PKA and EGFR.

Inhibition Assay of cdk2/Cyclin E Activity

Kinase reaction: 1.5 μM histone H1 (Sigma# H-5505) substrate, 25 μM ATP (0.2 μCi $P^{33}\gamma$ATP), 15 ng of baculovirus co-expressed cdk2/GST-Cyclin E, suitable concentrations of inhibitor in a final volume of 100 μl buffer (TRIS HCl 10 mM pH 7.5, MgCl$_2$ 10 mM, 7.5 mM DTT+0.2 mg/ml BSA) were added to each well of a 96 U bottom well plate. After 10 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS Ca$^{++}$/Mg$^{++}$ free and filtered by MultiScreen filtration system.

Detection: filters were allowed to dry at 37° C., then 100 μl/well scintillant were added and $^{33}$P labelled histone H1 was detected by radioactivity counting in the Top-Count instrument.

Inhibition Assay of cdk1/Cyclin B1 Activity

Kinase reaction: 1.5 μM histone H1 (Sigma# H-5505) substrate, 25 μM ATP (0.2 μCi $P^{33}\gamma$-ATP), 30 ng of baculovirus co-expressed cdk1/Cyclin B1, suitable concentrations of inhibitor in a final volume of 100 μl buffer (TRIS HCl 10 mM pH 7.5, MgCl$_2$ 10 mM, 7.5 mM DTT+0.2 mg/ml BSA) were added to each well of a 96 U bottom well plate. After 10 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS Ca$^{++}$/Mg$^{++}$ free and filtered by MultiScreen filtration system.

Detection: filters were allowed to dry at 37° C., then 100 μl/well scintillant were added and $^{33}$P labelled histone H1 was detected by radioactivity counting in the Top-Count instrument.

Inhibition Assay cdk4/Cyclin D1 activity

Kinase reaction: 0,4 uM μM mouse GST-Rb(769-921) (# sc-4112 from Santa Cruz) substrate, 10 μM ATP (0.5 μCi $P^{33}\gamma$-ATP), 100 ng of baculovirus expressed GST-cdk4/GST-Cyclin D1, suitable concentrations of inhibitor in a final volume of 50 μl buffer (TRIS HCl 10 mM pH 7.5, MgCl$_2$ 10 mM, 7.5 mM DTT+0.2 mg/ml BSA) were added to each well of a 96 U bottom well plate. After 40 min at 37° C. incubation, reaction was stopped by 20 μl EDTA 120 mM.

Capture: 60 μl were transferred from each well to Multi-Screen plate, to allow substrate binding to phosphocellulose filter. Plates were then washed 3 times with 150 μl/well PBS Ca$^{++}$/Mg$^{++}$ free and filtered by MultiScreen filtration system.

Detection: filters were allowed to dry at 37° C., then 100 μl/well scintillant were added and $^{33}$P labelled Rb fragment was detected by radioactivity counting in the Top-Count instrument.

Inhibition Assay of MAPK Activity

Kinase reaction: 10 μM MBP (Sigma# M-1891) substrate, 25 μM ATP (0.2 μCi $P^{33}\gamma$-ATP), 25 ng of bacterially expressed GST-MAPK (Upstate Biotechnology# 14-173), suitable concentrations of inhibitor in a final volume of 100 μl buffer (TRIS HCl 10 mM pH 7.5, MgCl$_2$ 10 mM, 7.5 mM DTT+0.1 mg/ml BSA) were added to each well of a 96 U bottom well plate. After 15 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS Ca$^{++}$/Mg$^{++}$ free and filtered by MultiScreen filtration system.

Detection: filters were allowed to dry at 37° C., then 100 μl/well scintillant were added and $^{33}$P labelled MBP was detected by radioactivity counting in the Top-Count instrument.

Inhibition Assay of PKA Activity

Kinase reaction: 10 μM histone H1 (Sigma# H-5505) substrate, 10 μM ATP (0.2 μCi $P^{33}\gamma$-ATP), 1U of bovine heart PKA (Sigma# 2645), suitable concentrations of inhibitor in a final volume of 100 μl buffer (TRIS HCl 10 mM pH 7.5, MgCl$_2$ 10 mM, 7.5 mM DTT+0.2 mg/ml BSA) were added to each well of a 96 U bottom well plate. After 5 min at 37° C. incubation, reaction was stopped by 20 μl EDTA 120 mM.

Capture: 100 μl were transferred from each well to Multi-Screen plate, to allow substrate binding to phosphocellulose filter. Plates were then washed 3 times with 150 μl/well PBS Ca$^{++}$/Mg$^{++}$ free and filtered by MultiScreen filtration system.

Detection: filters were allowed to dry at 37° C., then 100 μl/well scintillant were added and $^{33}$P labelled histone H1 was detected by radioactivity counting in the Top-Count instrument.

Inhibition Assay of EGFR Activity

Kinase reaction: 25 nM in house biotinylated PolyGluTyr (Sigma# 0275) substrate, 2,5 μM ATP (0.3 μCi P$^{33}$γ-ATP), 80 ng baculovirus expressed GST-EGFR, suitable concentrations of inhibitor in a final volume of 100 μl buffer (Hepes 50 mM pH 7,5, MnCl$_2$—MgCl$_2$ 3 mM, 1 mM DTT+3 μM NaVO3, 0.1 mg/ml BSA) were added to each well of a 96 U bottom well plate. After 5 min. at 37° C. incubation, reaction was stopped by 20 μl EDTA 120 mM.

Capture: 100 μl were transferred from each well to streptavidin-Flashplate, to allow biotinylated-substrate binding to plate. Plates were then washed 3 times with 150 μl/well PBS Ca$^{++}$/Mg$^{++}$ free.

Detection: radioactivity counting in the Top-Count instrument.

In addition, the inhibiting activity of putative cdk/cyclin inhibitors and the potency of selected compounds was determined through a method of assay based on the use of a SPA (Scintillation Proximity Assay) 96 well plate assay. The assay is based on the ability of streptavidin coated SPA beads to capture a biotinylated peptide derived from a phosphorylation site of histone.

When a radioactivity labelled phosphate moiety was transferred by the ser/threo kinase to the biotinylated histone peptide, light emitted was measured in a scintillation counter.

The inhibition assay of cdk5/p25 activity was performed according to the following protocol:

Kinase reaction: 1.0 μM biotinylated histone peptide substrate, 0.25 uCi P33g-ATP, 4 nM cdk5/p25 complex, 0–100 μM inhibitor in a final volume of 100 μl buffer (Hepes 20 mM pH 7.5, MgCl2 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 uM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

$$100X(1-(\text{Unknown}-Bkgd)/(\text{Enz. Control}-Bkgd))$$

IC50 values were calculated using a variation of the four parameter logistics equation:

$$Y=100/[1+10^{((\text{Log } EC50-X)*\text{Slope})}]$$

Where X=log(uM) and Y=% Inhibition.

The compounds of formula (I) are therefore useful to restrict the unregulated proliferation of tumor cells, hence in therapy in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty acid ester surfactant or lecithin.

The following examples are herewith intended to illustrate, without posing any limitation to, the present invention.

EXAMPLE 1

N-(3-formyl-1H-pyrrolo[2,3-b]pyridin-6-yl) acetamide 330 mg (2.48 mmol) of 1H-pyrrolo[2,3-b]pyridin-6-ylamine were dissolved in 15 ml of acetic anhydride and heated at reflux under stirring. After 6 hours the mixture was cooled down and 50 ml of aqueous sodium bicarbonate were added.

The solution was maintained under stirring at room temperature for 6 hours, then extracted with dichloromethane. The organic layer is dried over sodium sulfate and concentrated under vacuum, leading 480 mg (2.21 mmol;89% yield) of N-(1-acetyl-1H-pyrrolo[2,3-b]pyridin-6-yl) acetamide. This intermediate was dissolved in 5 ml of acetic acid 33% in water and 405 mg (2.87 mmol) of hexamethylenetetramine were added. After 12 hours at 100° C. the mixture was poured in icy water and basified with aqueous sodium bicarbonate and extracted with dichloromethane. The organic layer was then dried over sodium sulfate and evaporated to give 349 mg (60% yield) of the title compound.

$^1$H-NMR (400 MHz, DMSO-d$_6$) δ(ppm): 12.8 (s broad, 1H, NH); 10.39 (s, 1H, NHCO); 9.84 (s, 1H, CHO); 8.31 (d, J=8.2 Hz, 1H, CH-4); 8.3 (s, 1H, CH-2); 7.32 (d, J=8.2 Hz, 1H, CH-5); 2.09 (s, 3H, CH$_3$CO).

ESI (+) MS: m/z 204 (100, (M+H)$^+$)

Employing the same method, but starting from 6-chloro-1H-pyrrolo[2,3-b]pyridine, the following compound can be obtained: 6-chloro-1H-pyrrolo[2,3-b]pyridine-3-carbaldehyde;

$^1$H-NMR (400 MHz, DMSO-d$_6$) δ(ppm): 12.8 (s broad, 1H, NH); 9.9 s, 1H, CHO); 8.47 (s, 1H, CH-2); 8.39 (d, J=8.2 Hz, 1H, CH-4); 7.32 (d, J=8.2 Hz, 1H, CH-5).

ESI (−) MS: m/z 179 (100, (M+H)$^−$)

Employing the same method, but starting from 6-bromo-1H-pyrrolo[2,3-b]pyridine, the following compound was obtained: 6-bromo-1H-pyrrolo[2,3-b]pyridine-3-carbaldehyde;

$^1$H-NMR (400 MHz, DMSO-d$_6$) δ(ppm): 12.84 (s broad, 1H, NH); 9.91 (s, 1H, CHO); 8.46 (s, 1H, CH-2); 8.46 (d, J=8.2 Hz, 1H, CH-4); 7.45 (d, J=8.2 Hz, 1H, CH-5).

ESI (−) MS: m/z 225 (100, (M+H)$^−$)

Employing the same method, but starting from 1H-pyrrolo[2,3-b]pyridin-6-yl benzoate, the following compound was obtained: 3-formyl-1H-pyrrolo[2,3-b]pyridin-6-yl benzoate $^1$H-NMR (400 MHz, DMSO-d$_6$) δ(ppm): 12.8 (s broad, 1H, NH); 9.93 (s, 1H, CHO); 8.52 (d, J=8.2, 1H, CH-4); 8.48 (s, 1H, CH-2); 8.15 (d, J=8.2 Hz, 2H, orto-CH-phenyl); 7.76 (t, J=8.2 Hz, 1H, para-CH-phenyl); 7.62 (t, J=8.2 Hz, 2H, meta-CH-phenyl); 7.21 (d, J=8.2 Hz, 1H, para-CH-phenyl).

ESI (+) MS: m/z 267 (100, (M+H)$^+$)

EXAMPLE 2

Preparation of 3-(1H-pyrrolo[2,3-b]pyridin-3-yl)-2-phenyl-2-propenoic acid

A mixture of phenylacetic acid (0.0376 mol., 5.1 g) and 1H-pyrrolo[2,3-b]pyridine-3-carbaldehyde (0.0376 mol., 5.5 g) in acetic anhydride (0.1881 mol., 17.7 ml) and Et3N (0.0376 mol., 5.2 ml) was stirred at 100° C., for 6 hrs. The obtained solution was cooled to 50° C., quenched with conc. hydrochloric acid (10 ml) and extracted with EtOAc. The organic phase was extracted with 1 N NaOH. 3-(1H-Pyrrolo[2,3-b]pyridin-3-yl)-2-phenyl-2-propenoic acid was then precipitated from the aqueous layer with conc. hydrochloric acid with ice-cooling. Filtration and recrystallization from isopropyl alcohol of the crude product afforded 4,4 g of the desired compound as a white solid (44%), m.p. >230° C.

$^1$H-NMR (DMSO-d$_6$) δ ppm: 12.3 (s, 1H, COO<u>H</u>); 11.97 (s, 1H, NH pyrrole); 8.19 (dd, 1H, pyridine); 7.99 (s, 1H, C<u>H</u>=C); 7.64 (dd, 1H, pyridine); 7.2–7.5 (m, 5H, ph); 7.02 (dd, 1H, pyridine); 6.58 (d, 1H, pyrrole).

(M+H)$^+$=265

Analogously, the following compounds can be prepared starting from the corresponding aldehyde derivatives:

3-(6-acetylamino-1H-pyrrolo[2,3-b]pyridin-3-yl)-2-phenyl-2-propenoic acid;

3-(6-chloro-1H-pyrrolo[2,3-b]pyridin-3-yl)-2-phenyl-2-propenoic acid;

3-(6-bromo-1H-pyrrolo[2,3-b]pyridin-3-yl)-2-phenyl-2-propenoic acid;

3-(6-cyano-1H-pyrrolo[2,3-b]pyridin-3-yl)-2-phenyl-2-propenoic acid;

3-(6-hydroxy-1H-pyrrolo[2,3-b]pyridin-3-yl)-2-phenyl-2-propenoic acid;

3-[6-(aminomethyl)-1H-pyrrolo[2,3-b]pyridin-3-yl]-2-phenyl-2-propenoic acid;

3-{6-[(methylamino)methyl]-1H-pyrrolo[2,3-b]pyridin-3-yl}-2-phenyl-2-propenoic acid;

3-{6-[(benzylamino)methyl]-1H-pyrrolo[2,3-b]pyridin-3-yl}-2-phenyl-2-propenoic acid;

3-{6-[(benzoylamino)methyl]-1H-pyrrolo[2,3-b]pyridin-3-yl}-2-phenyl-2-propenoic acid;

2-phenyl-3-(6-{[(phenylacetyl)amino]methyl}-1H-pyrrolo[2,3-b]pyridin-3-yl)-2-propenoic acid;

3-[6-(benzoyloxy)-1H-pyrrolo[2,3-b]pyridin-3-yl]-2-phenyl-2-propenoic acid;

3-[6-(acetyloxy)-1H-pyrrolo[2,3-b]pyridin-3-yl]-2-phenyl-2-propenoic acid;

3-[6-(methylamino)-1H-pyrrolo[2,3-b]pyridin-3-yl]-2-phenyl-2-propenoic acid;

3-[6-(ethylamino)-1H-pyrrolo[2,3-b]pyridin-3-yl]-2-phenyl-2-propenoic acid;

3-[6-(isopropylamino)-1H-pyrrolo[2,3-b]pyridin-3-yl]-2-phenyl-2-propenoic acid;

3-[6-(cyclohexylamino)-1H-pyrrolo[2,3-b]pyridin-3-yl]-2-phenyl-2-propenoic acid;

3-(6-anilino-1H-pyrrolo[2,3-b]pyridin-3-yl)-2-phenyl-2-propenoic acid;
3-[6-(4-bromoanilino)-1H-pyrrolo[2,3-b]pyridin-3-yl]-2-phenyl-2-propenoic acid;
3-[6-(3-hydroxyanilino)-1H-pyrrolo[2,3-b]pyridin-3-yl]-2-phenyl-2-propenoic acid;
3-{6-[4-(aminosulfonyl)anilino]-1H-pyrrolo[2,3-b]pyridin-3-yl}-2-phenyl-2-propenoic acid;
3-{6-[4-(aminocarbonyl)anilino[-1H-pyrrolo[2,3-b]pyridin-3-yl}-2-phenyl-2-propenoic acid;
3-[6-(3-aminoanilino)-1H-pyrrolo[2,3-b]pyridin-3-yl]-2-phenyl-2-propenoic acid;
2-phenyl-3-[6-(3-pyridinylamino)-1H-pyrrolo[2,3-b]pyridin-3-yl]-2-propenoic acid;
2-phenyl-3-[6-(1,3-thiazol-2-ylamino)-1H-pyrrolo[2,3-b]pyridin-3-yl]-2-propenoic acid;
3-[6-(benzylamino)-1H-pyrrolo[2,3-b]pyridin-3-yl]-2-phenyl-2-propenoic acid;
3-(6-{[4-(aminosulfonyl)benzyl]amino}-1H-pyrrolo[2,3-b]pyridin-3-yl)-2-phenyl-2-propenoic acid;
3-[6-(acetylamino)-1H-pyrrolo[2,3-b]pyridin-3-yl]-2-phenyl-2-propenoic acid;
3-[6-(benzoylamino)-1H-pyrrolo[2,3-b]pyridin-3-yl]-2-phenyl-2-propenoic acid;
3-{6-[(4-bromobenzoyl)amino]-1H-pyrrolo[2,3-b]pyridin-3-yl}-2-phenyl-2-propenoic acid;
3-{6-[(3-hydroxybenzoyl)amino]-1H-pyrrolo[2,3-b]pyridin-3-yl}-2-phenyl-2-propenoic acid;
3-{6-[(3-aminobenzoyl)amino]-1H-pyrrolo[2,3-b]pyridin-3-yl}-2-phenyl-2-propenoic acid;
3-(6-(butyrylamino)-1H-pyrrolo[2,3-b]pyridin-3-yl]-2-phenyl-2-propenoic acid;
2-phenyl-3-{6-[(phenylacetyl)amino]-1H-pyrrolo[2,3-b]pyridin-3-yl}-2-propenoic acid;
3-(6-{[(3-hydroxyphenyl)acetyl]amino}-1H-pyrrolo[2,3-b]pyridin-3-yl)-2-phenyl-2-propenoic acid;
3-(6-{[(3-chlorophenyl)acetyl]amino}-1H-pyrrolo[2,3-b]pyridin-3-yl)-2-phenyl-2-propenoic acid;
3-(6-{[(3-aminophenyl)acetyl]amino}-1H-pyrrolo[2,3-b]pyridin-3-yl)-2-phenyl-2-propenoic acid;
2-phenyl-3-{6-[(3-pyridinylacetyl)amino]-1H-pyrrolo[2,3-b]pyridin-3-yl}-2-propenoic acid;
3-{6-[(1H-indol-3-ylcarbonyl)amino]-1H-pyrrolo[2,3-b]pyridin-3-yl}-2-phenyl-2-propenoic acid;
3-{6-[(1H-indol-3-ylacetyl)amino]-1H-pyrrolo[2,3-b]pyridin-3-yl}-2-phenyl-2-propenoic acid;
2-phenyl-3-{6-[(2-thienylcarbonyl)amino]-1H-pyrrolo[2,3-b]pyridin-3-yl}-2-propenoic acid;
3-{6-[([1,1'-biphenyl]-4-ylcarbonyl)amino]-1H-pyrrolo[2,3-b]pyridin-3-yl}-2-phenyl-2-propenoic acid;
3-{6-[([1,1'-biphenyl]-4-ylacetyl)amino]-1H-pyrrolo[2,3-b]pyridin-3-yl}-2-phenyl-2-propenoic acid;
3-{6-[(1,3-oxazol-2-ylacetyl)amino]-1H-pyrrolo[2,3-b]pyridin-3-yl}-2-phenyl-2-propenoic acid;
2-phenyl-3-{6-[(1,3-thiazol-2-ylacetyl)amino]-1H-pyrrolo[2,3-b]pyridin-3-yl}-2-propenoic acid;
3-{6-[(aminocarbonyl)amino]-1H-pyrrolo[2,3-b]pyridin-3-yl}-2-phenyl-2-propenoic acid;
3-(6-{[(methylamino)carbonyl]amino}-1H-pyrrolo[2,3-b]pyridin-3-yl)-2-phenyl-2-propenoic acid;
3-{6-[(anilinocarbonyl)amino]-1H-pyrrolo[2,3-b]pyridin-3-yl}-2-phenyl-2-propenoic acid;
3-(6-{[(4-bromoanilino)carbonyl]amino}-1H-pyrrolo[2,3-b]pyridin-3-yl)-2-phenyl-2-propenoic acid;
3-(6-{[(3-hydroxyanilino)carbonyl]amino}-1H-pyrrolo[2,3-b]pyridin-3-yl)-2-phenyl-2-propenoic acid;
3-(6-{[(benzylamino)carbonyl]amino}-1H-pyrrolo[2,3-b]pyridin-3-yl)-2-phenyl-2-propenoic acid;
2-phenyl-3-{6-[(1-piperidinylcarbonyl)amino]-1H-pyrrolo[2,3-b]pyridin-3-yl}-2-propenoic acid;
2-phenyl-3-{6-[(1-pyrrolidinylcarbonyl)amino]-1H-pyrrolo[2,3-b]pyridin-3-yl}-2-propenoic acid;
3-(6-{[(4-methyl-1-piperazinyl)carbonyl]amino}-1H-pyrrolo[2,3-b]pyridin-3-yl)-2-phenyl-2-propenoic acid;
3-{6-[(4-morpholinylcarbonyl)amino]-1H-pyrrolo[2,3-b]pyridin-3-yl}-2-phenyl-2-propenoic acid;
3-{6-[(ethoxycarbonyl)amino]-1H-pyrrolo[2,3-b]pyridin-3-yl}-2-phenyl-2-propenoic acid;
3-{6-[(tert-butoxycarbonyl)amino]-1H-pyrrolo[2,3-b]pyridin-3-yl}-2-phenyl-2-propenoic acid;
3-{6-[(methylsulfonyl)amino]-1H-pyrrolo[2,3-b]pyridin-3-yl}-2-phenyl-2-propenoic acid;
2-phenyl-3-{6-[(phenylsulfonyl)amino]-1H-pyrrolo[2,3-b]pyridin-3-yl}-2-propenoic acid;
2-phenyl-3-(6-{[(phenylsulfonyl)methyl]amino}-1H-pyrrolo[2,3-b]pyridin-3-yl)-2-propenoic acid;
3-(6-{[([1,1'-biphenyl]-4-ylmethyl)sulfonyl]amino}-1H-pyrrolo[2,3-b]pyridin-3-yl)-2-phenyl-2-propenoic acid;
3-{6-[([1,1'-biphenyl]-4-ylsulfonyl)amino]-1H-pyrrolo[2,3-b]pyridin-3-yl}-2-phenyl-2-propenoic acid;
3-(4-chloro-1H-pyrrolo[2,3-b]pyridin-3-yl)-2-phenyl-2-propenoic acid;
3-(4-anilino-1H-pyrrolo[2,3-b]pyridin-3-yl)-2-phenyl-2-propenoic acid;
3-[4-(4-bromoanilino)-1H-pyrrolo[2,3-b]pyridin-3-yl]-2-phenyl-2-propenoic acid;
3-[4-(3-hydroxyanilino)-1H-pyrrolo[2,3-b]pyridin-3-yl]-2-phenyl-2-propenoic acid;
3-{4-[4-(aminosulfonyl)anilino]-1H-pyrrolo[2,3-b]pyridin-3-yl}-2-phenyl-2-propenoic acid;
3-{4-[4-(aminocarbonyl)anilino]-1H-pyrrolo[2,3-b]pyridin-3-yl}-2-phenyl-2-propenoic acid;
3-[4-(3-aminoanilino)-1H-pyrrolo[2,3-b]pyridin-3-yl]-2-phenyl-2-propenoic acid;
2-phenyl-3-[4-(3-pyridinylamino)-1H-pyrrolo[2,3-b]pyridin-3-yl]-2-propenoic acid;
2-phenyl-3-[4-(1,3-thiazol-2-ylamino)-1H-pyrrolo[2,3-b]pyridin-3-yl]-2-propenoic acid;
3-(4-amino-1H-pyrrolo[2,3-b]pyridin-3-yl)-2-phenyl-2-propenoic acid;
3-[4-(methylamino)-1H-pyrrolo[2,3-b]pyridin-3-yl]-2-phenyl-2-propenoic acid;
3-[4-(cyclohexylamino)-1H-pyrrolo[2,3-b]pyridin-3-yl]-2-phenyl-2-propenoic acid;
3-[4-(benzylamino)-1H-pyrrolo[2,3-b]pyridin-3-yl]-2-phenyl-2-propenoic acid;
3-(4-{[4-(aminosulfonyl)benzyl]amino}-1H-pyrrolo[2,3-b]pyridin-3-yl)-2-phenyl-2-propenoic acid;
3-[4-(acetylamino)-1H-pyrrolo[2,3-b]pyridin-3-yl]-2-phenyl-2-propenoic acid;
3-[4-(benzoylamino)-1H-pyrrolo[2,3-b]pyridin-3-yl]-2-phenyl-2-propenoic acid;
3-{4-[(4-bromobenzoyl)amino]-1H-pyrrolo[2,3-b]pyridin-3-yl}-2-phenyl-2-propenoic acid;
3-{4-[(3-hydroxybenzoyl)amino]-1H-pyrrolo[2,3-b]pyridin-3-yl}-2-phenyl-2-propenoic acid;
3-{4-[(3-aminobenzoyl)amino]-1H-pyrrolo[2,3-b]pyridin-3-yl}-2-phenyl-2-propenoic acid;
3-[4-(butyrylamino)-1H-pyrrolo[2,3-b]pyridin-3-yl]-2-phenyl-2-propenoic acid;
2-phenyl-3-{4-[(phenylacetyl)amino]-1H-pyrrolo[2,3-b]pyridin-3-yl}-2-propenoic acid;
3-(4-{[(3-hydroxyphenyl)acetyl]amino}-1H-pyrrolo[2,3-b]pyridin-3-yl)-2-phenyl-2-propenoic acid;
3-(4-{[(3-chlorophenyl)acetyl]amino}-1H-pyrrolo[2,3-b]pyridin-3-yl)-2-phenyl-2-propenoic acid;

3-(4-}[(3-aminophenyl)acetyl]amino}-1H-pyrrolo[2,3-b]pyridin-3-yl)-2-phenyl-2-propenoic acid;
2-phenyl-3-{4-[(3-pyridinylacetyl)amino]-1H-pyrrolo[2,3-b]pyridin-3-yl}-2-propenoic acid;
3-{4-[(1H-indol-3-ylcarbonyl)amino]-1H-pyrrolo[2,3-b]pyridin-3-yl}-2-phenyl-2-propenoic acid;
3-{4-[(1H-indol-3-ylacetyl)amino]-1H-pyrrolo[2,3-b]pyridin-3-yl}-2-phenyl-2-propenoic acid;
2-phenyl-3-{4-[(3-thienylcarbonyl)amino]-1H-pyrrolo[2,3-b]pyridin-3-yl}-2-propenoic acid;
3-{4-[([1,1'-biphenyl]-4-ylcarbonyl)amino]-1H-pyrrolo[2,3-b]pyridin-3-yl}-2-phenyl-2-propenoic acid;
3-{4-[(1,3-oxazol-2-ylacetyl)amino]-1H-pyrrolo[2,3-b]pyridin-3-yl}-2-phenyl-2-propenoic acid;
2-phenyl-3-{4-[(1,3-thiazol-2-ylacetyl)amino]-1H-pyrrolo[2,3-b]pyridin-3-yl}-2-propenoic acid;
3-{4-[(aminocarbonyl)amino]-1H-pyrrolo[2,3-b]pyridin-3-yl}-2-phenyl-2-propenoic acid;
3-(4-{[(methylamino)carbonyl]amino}-1H-pyrrolo[2,3-b]pyridin-3-yl)-2-phenyl-2-propenoic acid;
3-{4-[(anilinocarbonyl)amino]-1H-pyrrolo[2,3-b]pyridin-3-yl}-2-phenyl-2-propenoic acid;
3-(4-{[(4-bromoanilino)carbonyl]amino}-1H-pyrrolo[2,3-b]pyridin-3-yl)-2-phenyl-2-propenoic acid;
3-(4-{[(3-hydroxyanilino)carbonyl]amino}-1H-pyrrolo[2,3-b]pyridin-3-yl)-2-phenyl-2-propenoic acid;
3-(4-{[(benzylamino)carbonyl]amino}-1H-pyrrolo[2,3-b]pyridin-3-yl)-2-phenyl-2-propenoic acid;
2-phenyl-3-{4-[(1-piperidinylcarbonyl)amino]-1H-pyrrolo[2,3-b]pyridin-3-yl}-2-propenoic acid;
2-phenyl-3-{4-[(1-pyrrolidinylcarbonyl)amino]-1H-pyrrolo[2,3-b]pyridin-3-yl}-2-propenoic acid;
3-(4-{[(4-methyl-1-piperazinyl)carbonyl]amino}-1H-pyrrolo[2,3-b]pyridin-3-yl)-2-phenyl-2-propenoic acid;
3-{4-[(4-morpholinylcarbonyl)amino]-1H-pyrrolo[2,3-b]pyridin-3-yl}-2-phenyl-2-propenoic acid;
3-{4-[(ethoxycarbonyl)amino]-1H-pyrrolo[2,3-b]pyridin-3-yl}-2-phenyl-2-propenoic acid;
3-{4-[(tert-butoxycarbonyl)amino]-1H-pyrrolo[2,3-b]pyridin-3-yl}-2-phenyl-2-propenoic acid;
3-{4-[(methylsulfonyl)amino]-1H-pyrrolo[2,3-b]pyridin-3-yl}-2-phenyl-2-propenoic acid;
2-phenyl-3-{4-[(phenylsulfonyl)amino]-1H-pyrrolo[2,3-b]pyridin-3-yl}-2-propenoic acid;
3-{4-[(benzylsulfonyl)amino]-1H-pyrrolo[2,3-b]pyridin-3-yl}-2-phenyl-2-propenoic acid;
3-{4-[([1,1'-biphenyl]-4-ylsulfonyl)amino]-1H-pyrrolo[2,3-b]pyridin-3-yl}-2-phenyl-2-propenoic acid;
3-(4-{[([1,1'-biphenyl]-4-ylmethyl)sulfonyl]amino}-1H-pyrrolo[2,3-b]pyridin-3-yl)-2-phenyl-2-propenoic acid;
3-(5-amino-1H-pyrrolo[2,3-b]pyridin-3-yl)-2-phenyl-2-propenoic acid;
3-[5-(methylamino)-1H-pyrrolo[2,3-b]pyridin-3-yl]-2-phenyl-2-propenoic acid;
3-[5-(cyclohexylamino)-1H-pyrrolo[2,3-b]pyridin-3-yl]-2-phenyl-2-propenoic acid;
3-[5-(benzylamino)-1H-pyrrolo[2,3-b]pyridin-3-yl]-2-phenyl-2-propenoic acid;
3-(5-{[4-(aminosulfonyl)benzyl]amino}-1H-pyrrolo[2,3-b]pyridin-3-yl)-2-phenyl-2-propenoic acid;
3-[5-(acetylamino)-1H-pyrrolo[2,3-b]pyridin-3-yl]-2-phenyl-2-propenoic acid;
3-[5-(benzoylamino)-1H-pyrrolo[2,3-b]pyridin-3-yl]-2-phenyl-2-propenoic acid;
3-{5-[(4-bromobenzoyl)amino]-1H-pyrrolo[2,3-b]pyridin-3-yl}-2-phenyl-2-propenoic acid;
3-{5-[(3-hydroxybenzoyl)amino]-1H-pyrrolo[2,3-b]pyridin-3-yl}-2-phenyl-2-propenoic acid;
3-{5-[(3-aminobenzoyl)amino]-1H-pyrrolo[2,3-b]pyridin-3-yl}-2-phenyl-2-propenoic acid;
3-[5-(butyrylamino)-1H-pyrrolo[2,3-b]pyridin-3-yl]-2-phenyl-2-propenoic acid;
2-phenyl-3-{5-[(phenylacetyl)amino]-1H-pyrrolo[2,3-b]pyridin-3-yl}-2-propenoic acid;
3-(5-{[(3-hydroxyphenyl)acetyl]amino}-1H-pyrrolo[2,3-b]pyridin-3-yl)-2-phenyl-2-propenoic acid;
3-(5-{[(3-chlorophenyl)acetyl]amino}-1H-pyrrolo[2,3-b]pyridin-3-yl)-2-phenyl-2-propenoic acid;
3-(5-{[(3-aminophenyl)acetyl]amino}-1H-pyrrolo[2,3-b]pyridin-3-yl)-2-phenyl-2-propenoic acid;
2-phenyl-3-{5-[(3-pyridinylacetyl)amino]-1H-pyrrolo[2,3-b]pyridin-3-yl}-2-propenoic acid;
3-{5-[(1H-indol-3-ylcarbonyl)amino]-1H-pyrrolo[2,3-b]pyridin-3-yl}-2-phenyl-2-propenoic acid;
3-{5-[(1H-indol-3-ylacetyl)amino]-1H-pyrrolo[2,3-b]pyridin-3-yl}-2-phenyl-2-propenoic acid;
2-phenyl-3-{5-[(3-thienylcarbonyl)amino]-1H-pyrrolo[2,3-b]pyridin-3-yl}-2-propenoic acid;
(2E)-3-{5-[([1,1'-biphenyl]-4-ylcarbonyl)amino]-1H-pyrrolo[2,3-b]pyridin-3-yl}-2-phenyl-2-propenoic acid;
3-{5-[(1,3-oxazol-2-ylacetyl)amino]-1H-pyrrolo[2,3-b]pyridin-3-yl}-2-phenyl-2-propenoic acid;
2-phenyl-3-{5-[(1,3-thiazol-2-ylacetyl)amino]-1H-pyrrolo[2,3-b]pyridin-3-yl}-2-propenoic acid;
3-{5-[(aminocarbonyl)amino]-1H-pyrrolo[2,3-b]pyridin-3-yl}-2-phenyl-2-propenoic acid;
3-(5-{[(methylamino)carbonyl]amino}-1H-pyrrolo[2,3-b]pyridin-3-yl)-2-phenyl-2-propenoic acid;
3-{5-[(anilinocarbonyl)amino]-1H-pyrrolo[2,3-b]pyridin-3-yl}-2-phenyl-2-propenoic acid;
3-(5-{[(4-bromoanilino)carbonyl]amino}-1H-pyrrolo[2,3-b]pyridin-3-yl)-2-phenyl-2-propenoic acid;
3-(5-{[(3-hydroxyanilino)carbonyl]amino}-1H-pyrrolo[2,3-b]pyridin-3-yl)-2-phenyl-2-propenoic acid;
3-(5-{[(benzylamino)carbonyl]amino}-1H-pyrrolo[2,3-b]pyridin-3-yl)-2-phenyl-2-propenoic acid;
2-phenyl-3-{5-[(1-piperidinylcarbonyl)amino]-1H-pyrrolo[2,3-b]pyridin-3-yl}-2-propenoic acid;
2-phenyl-3-{5-[(1-pyrrolidinylcarbonyl)amino]-1H-pyrrolo[2,3-b]pyridin-3-yl}-2-propenoic acid;
3-(5-{[(4-methyl-1-piperazinyl)carbonyl]amino}-1H-pyrrolo[2,3-b]pyridin-3-yl)-2-phenyl-2-propenoic acid;
3-{5-[(4-morpholinylcarbonyl)amino]-1H-pyrrolo[2,3-b]pyridin-3-yl}-2-phenyl-2-propenoic acid;
3-{5-[(ethoxycarbonyl)amino]-1H-pyrrolo[2,3-b]pyridin-3-yl}-2-phenyl-2-propenoic acid;
3-{5-[(tert-butoxycarbonyl)amino]-1H-pyrrolo[2,3-b]pyridin-3-yl}-2-phenyl-2-propenoic acid;
3-{5-[(methylsulfonyl)amino]-1H-pyrrolo[2,3-b]pyridin-3-yl}-2-phenyl-2-propenoic acid;
2-phenyl-3-{5-[(phenylsulfonyl)amino]-1H-pyrrolo[2,3-b]pyridin-3-yl}-2-propenoic acid;
3-{5-[(benzylsulfonyl)amino]-1H-pyrrolo[2,3-b]pyridin-3-yl}-2-phenyl-2-propenoic acid;
3-{5-[([1,1'-biphenyl]-4-ylsulfonyl)amino]-1H-pyrrolo[2,3-b]pyridin-3-yl}-2-phenyl-2-propenoic acid;
3-(5-{[([1,1'-biphenyl]-4-ylmethyl)sulfonyl]amino}-1H-pyrrolo[2,3-b]pyridin-3-yl)-2-phenyl-2-propenoic acid;
2-(4-chlorophenyl)-3-(1H-pyrrolo[2,3-b]pyridin-3-yl)-2-propenoic acid
3-(1H-pyrrolo[2,3-b]pyridin-3-yl)-2-(4-tolyl)-2-propenoic acid
3-(1H-pyrrolo[2,3-b]pyridin-3-yl)-2-[2-(trifluoromethyl)phenyl]-2-propenoic acid
2-(1-acetyl-1H-indol-3-yl)-3-(1H-pyrrolo[2,3-b]pyridin-3-yl)-2-propenoic acid 2-(1H-indol-3-yl)-3-(1H-pyrrolo[2,3-b]pyridin-3-yl)-2-propenoic acid 2-(3-fluoro-4-hydroxyphenyl)-3-(1H-pyrrolo[2,3-b]pyridin-3-yl)-2-propenoic acid 2-(2,3-dihydro-1H-inden-5-yl)-3-(1H-pyrrolo[2,3-b]pyridin-3-yl)-2-propenoic acid 2-(3-pyridinyl)-3-(1H-pyrrolo[2,3-b]pyridin-3-yl)-2-propenoic acid 2-(4-hydroxyphenyl)-3-(1H-pyrrolo[2,3-b]pyridin-3-yl)-2-propenoic acid 2-(4-methoxyphenyl)-3-(1H-pyrrolo[2,3-b]pyridin-3-yl)-2-propenoic acid 2-(2-hydroxyphenyl)-3-(1H-pyrrolo[2,3-b]pyridin-3-yl)-2-propenoic acid 2-(2-methoxyphenyl)-3-(1H-pyrrolo[2,3-b]pyridin-3-yl)-2-propenoic acid 2-[1,1'-biphenyl]-4-yl-3-(1H-pyrrolo[2,3-b]pyridin-3-yl)-2-propenoic acid 2-(4-hydroxy-5-isopropyl-2-methylphenyl)-3-(1H-pyrrolo[2,3-b]pyridin-3-yl)-2-propenoic acid 2-(4-hydroxy-3-methoxyphenyl)-3-(1H-pyrrolo[2,3-b]pyridin-3-yl)-2-propenoic acid 2-(3-chlorophenyl)-3-(1H-pyrrolo[2,3-b]pyridin-3-yl)-2-propenoic acid 2-(3-methoxyphenyl)-3-(1H-pyrrolo[2,3-b]pyridin-3-yl)-2-propenoic acid 2-(3-bromophenyl)-3-(1H-pyrrolo[2,3-b]pyridin-3-yl)-2-propenoic acid 2-(1,3-benzodioxol-5-yl)-3-(1H-pyrrolo[2,3-b]pyridin-3-yl)-2-propenoic acid 2-(3,5-dimethoxyphenyl)-3-(1H-pyrrolo[2,3-b]pyridin-3-yl)-2-propenoic acid 2-(3-fluorophenyl)-3-(1H-pyrrolo[2,3-b]pyridin-3-yl)-2-propenoic acid 2-(4-butoxyphenyl)-3-(1H-pyrrolo[2,3-b]pyridin-3-yl)-2-propenoic acid 2-(3-chloro-4-hydroxyphenyl)-3-(1H-pyrrolo[2,3-b]pyridin-3-yl)-2-propenoic acid 2-[4-(methylsulfonyl)phenyl]-3-(1H-pyrrolo[2,3-b]pyridin-3-yl)-2-propenoic acid 2-(4-ethoxyphenyl)-3-(1H-pyrrolo[2,3-b]pyridin-3-yl)-2-propenoic acid 2-(3-methylphenyl)-3-(1H-pyrrolo[2,3-b]pyridin-3-yl)-2-propenoic acid 2-(2-methylphenyl)-3-(1H-pyrrolo[2,3-b]pyridin-3-yl)-2-propenoic acid 2-(3,4-dihydroxyphenyl)-3-(1H-pyrrolo[2,3-b]pyridin-3-yl)-2-propenoic acid 3-(1H-pyrrolo[2,3-b]pyridin-3-yl)-2-(2-thienyl)-2-propenoic acid 2-(2-bromophenyl)-3-(1H-pyrrolo[2,3-b]pyridin-3-yl)-2-propenoic acid 2-(2-fluorophenyl)-3-(1H-pyrrolo[2,3-b]pyridin-3-yl)-2-propenoic acid 2-(2-chlorophenyl)-3-(1H-pyrrolo[2,3-b]pyridin-3-yl)-2-propenoic acid 2-(2,4-dichlorophenyl)-3-(1H-pyrrolo[2,3-b]pyridin-3-yl)-2-propenoic acid 2-(2-chloro-6-fluorophenyl)-3-(1H-pyrrolo[2,3-b]pyridin-3-yl)-2-propenoic acid 2-(2,6-dichlorophenyl)-3-(1H-pyrrolo[2,3-b]pyridin-3-yl)-2-propenoic acid 2-(2,5-dimethoxyphenyl)-3-(1H-pyrrolo[2,3-b]pyridin-3-yl)-2-propenoic acid 2-(3,4-dichlorophenyl)-3-(1H-pyrrolo[2,3-b]pyridin-3-yl)-2-propenoic acid 3-(1H-pyrrolo[2,3-b]pyridin-3-yl)-2-(3,4,5-trimethoxyphenyl)-2-propenoic acid 3-(1H-pyrrolo[2,3-b]pyridin-3-yl)-2-[3-(trifluoromethyl)phenyl)]-2-propenoic acid 3-(1H-pyrrolo[2,3-b]pyridin-3-yl)-2-[4-(trifluoromethyl)phenyl]-2-propenoic acid 2-[3,5-bis(trifluoromethyl)phenyl]-3-(1H-pyrrolo[2,3-b]pyridin-3-yl)-2-propenoic acid 2-(2,4-difluorophenyl)-3-(1H-pyrrolo[2,3-b]pyridin-3-yl)-2-propenoic acid 2-(2,5-difluorophenyl)-3-(1H-pyrrolo[2,3-b]pyridin-3-yl)-2-propenoic acid 2-(3,4-difluorophenyl)-3-(1H-pyrrolo[2,3-b]pyridin-3-yl)-2-propenoic acid 2-(3,5-difluorophenyl)-3-(1H-pyrrolo[2,3-b]pyridin-3-yl)-2-propenoic acid 2-[4-(benzyloxy)-3-methoxyphenyl]-3-(1H-pyrrolo[2,3-b]pyridin-3-yl)-2-propenoic acid 3-(1H-pyrrolo[2,3-b]pyridin-3-yl)-2-(3-thienyl)-2-propenoic acid 2-(5-methoxy-1H-indol-3-yl)-3-(1H-pyrrolo[2,3-b]pyridin-3-yl)-2-propenoic acid 2-(1-naphthyl)-3-(1H-pyrrolo[2,3-b]pyridin-3-yl)-2-propenoic acid 2-(3-methyl-1-benzothien-2-yl)-3-(1H-pyrrolo[2,3-b]pyridin-3-yl)-2-propenoic acid 2-(3,4-dimethoxyphenyl)-3-(1H-pyrrolo[2,3-b]pyridin-3-yl)-2-propenoic acid 2-(4-bromophenyl)-3-(1H-pyrrolo[2,3-b]pyridin-3-yl)-2-propenoic acid 2-[4-(acetylamino)phenyl]-3-(1H-pyrrolo[2,3-b]pyridin-3-yl)-2-propenoic acid 2-[4-amino-phenyl]-3-(1H-pyrrolo[2,3-b]pyridin-3-yl)-2-propenoic acid 2-(5-bromo-1H-indol-3-yl)-3-(1H-pyrrolo[2,3-b]pyridin-3-yl)-2-propenoic acid 2-(1-methyl-1H-indol-3-yl)-3-(1H-pyrrolo[2,3-b]pyridin-3-yl)-2-propenoic acid 2-(4-fluorophenyl)-3-(1H-pyrrolo[2,3-b]pyridin-3-yl)-2-propenoic acid 2-[2,5-bis(trifluoromethyl)phenyl]-3-(1H-pyrrolo[2,3-b]pyridin-3-yl)-2-propenoic acid 2-(2,3,5-difluorophenyl)-3-(1H-pyrrolo[2,3-b]pyridin-3-yl)-2-propenoic acid 2-[5-(benzyloxy)-1H-indol-3-yl]-3-(1H-pyrrolo[2,3-b]pyridin-3-yl)-2-propenoic acid 2-(2-amino-1,3-thiazol-4-yl)-3-(1H-pyrrolo[2,3-b]pyridin-3-yl)-2-propenoic acid 2-mesityl-3-(1H-pyrrolo[2,3-b]pyridin-3-yl)-2-propenoic acid 3-(1H-pyrrolo[2,3-b]pyridin-3-yl)-2-[4-(trifluoromethoxy)phenyl]-2-propenoic acid 2-(3,5-ditert-butyl-4-hydroxyphenyl)-3-(1H-pyrrolo[2,3-b]pyridin-3-yl)-2-propenoic acid 2-[4-(2-amino-2-oxoethoxy)phenyl]-3-(1H-pyrrolo[2,3-b]pyridin-3-yl)-2-propenoic acid 2-{4-[2-oxo-2-(1-pyrrolidinyl)ethoxy]phenyl}-3-(1H-pyrrolo[2,3-b]pyridin-3-yl)-2-propenoic acid 2-(3-hydroxy-5-methoxy-2-propylphenyl)-3-(1H-pyrrolo[2,3-b]pyridin-3-yl)-2-propenoic acid 2-(4-phenoxyphenyl)-3-(1H-pyrrolo[2,3-b]pyridin-3-yl)-2-propenoic acid 2-[2-(4-chlorophenyl)-1,3-thiazol-4-yl]-3-(1H-pyrrolo[2,3-b]pyridin-3-yl)-2-propenoic acid 2-{3-[(methylsulfonyl)amino]phenyl}-3-(1H-pyrrolo[2,3-b]pyridin-3-yl)-2-propenoic acid 2-{4-[(methylsulfonyl)amino]phenyl}-3-(1H-pyrrolo[2,3-b]pyridin-3-yl)-2-propenoic acid 2-[4-(1-pyrrolidinyl)phenyl]-3-(1H-pyrrolo[2,3-b]pyridin-3-yl)-2-propenoic acid 2-{4-[(2-amino-2-oxoethyl)amino]phenyl}-3-(1H-pyrrolo [2,3-b]pyridin-3-yl)-2-propenoic acid.

EXAMPLE 3

Preparation of 3-(1H-pyrrolo[2,3-b]pyridin-3-yl)-2-phenyl-2-propenamide

To a solution of 264 mg (1 mmol.) of 3-(1H-pyrrolo[2, 3-b]pyridin-3-yl)-2-phenyl-2-propenoic acid in 1.5 ml of THFd and 3 ml of DMFd was added 350 μl of N,N,-diisopropylethylamine and 154 mg (1.4 mmol.) of N-hydroxybenzotriazole ammonium salt. The obtained mixture was cooled to −20° C. and 266 mg (1.4 mmol.) of 1-(3-dimethylaminopropyl)-3-ethylcarbodiimide were added. The reaction mixture was stirred for 2 hours at −20° C. and then warmed to room temperature. After additional 12 hours, the organic layer was diluted with dichloromethane, washed with saturated sodium bicarbonate, brine, dried over sodium sulphate and evaporated. The residual solid was triturated with EtOAc to afford 76 mg of the title compound as a white solid (yield 29%) m.p. 222–224° C. $^1$H-NMR (DMSO-d$_6$) δ ppm: 11.79 (s, 1H, NH pyrrole); 8.19 (dd, 1H, pyridine); 7.82 (dd, 1H, pyridine); 7.76 (s, 1H, C$\underline{H}$=C); 7.2–7.5 (m, 5H, ph); 7.04 (dd, 1H, pyridine); 6.3 (d, 1H, pyrrole); 7.1 (s, 1H, CON$\underline{H}_2$); 6.7 (s, 1H, CON$\underline{H}_2$). (M+H)$^+$=264

Analogously the following compounds can be prepared starting from the corresponding carboxylic acid:

3-(6-acetylamino-1H-pyrrolo[2,3-b]pyridin-3-yl)-2-phenyl-2-propenamide;
3-(6-chloro-1H-pyrrolo[2,3-b]pyridin-3-yl)-2-phenyl-2-propenamide;
3-(6-bromo-1H-pyrrolo[2,3-b]pyridin-3-yl)-2-phenyl-2-propenamide;
3-(6-cyano-1H-pyrrolo[2,3-b]pyridin-3-yl)-2-phenyl-2-propenamide;
3-(6-hydroxy-1H-pyrrolo[2,3-b]pyridin-3-yl)-2-phenyl-2-propenamide;
3-[6-(aminomethyl)-1H-pyrrolo[2,3-b]pyridin-3-yl]-2-phenyl-2-propenamide;
3-{6-[(methylamino)methyl]-1H-pyrrolo[2,3-b]pyridin-3-yl}-2-phenyl-2-propenamide;
3-{6-[(benzylamino)methyl]-1H-pyrrolo[2,3-b]pyridin-3-yl}-2-phenyl-2-propenamide;
N-({3-[3-amino-3-oxo-2-phenyl-1-propenyl]-1H-pyrrolo[2,3-b]pyridin-6-yl}methyl)benzamide;
2-phenyl-3-(6-{[(phenylacetyl)amino]methyl}-1H-pyrrolo[2,3-b]pyridin-3-yl)-2-propenamide;
3-[3-amino-3-oxo-2-phenyl-1-propenyl]-1H-pyrrolo[2,3-b] pyridin-6-yl benzoate;
3-[3-amino-3-oxo-2-phenyl-1-propenyl]-1H-pyrrolo[2,3-b] pyridin-6-yl acetate;
3-[6-(methylamino)-1H-pyrrolo[2,3-b]pyridin-3-yl]-2-phenyl-2-propenamide;
3-[6-(ethylamino)-1H-pyrrolo[2,3-b]pyridin-3-yl]-2-phenyl-2-propenamide;
3-[6-(isopropylamino)-1H-pyrrolo[2,3-b]pyridin-3-yl]-2-phenyl-2-propenamide;
3-[6-(cyclohexylamino)-1H-pyrrolo[2,3-b]pyridin-3-yl]-2-phenyl-2-propenamide;
3-(6-anilino-1H-pyrrolo[2,3-b]pyridin-3-yl)-2-phenyl-2-propenamide;
3-[6-(4-bromoanilino)-1H-pyrrolo[2,3-b]pyridin-3-yl]-2-phenyl-2-propenamide;
3-[6-(3-hydroxyanilino)-1H-pyrrolo[2,3-b]pyridin-3-yl]-2-phenyl-2-propenamide;
3-{6-[4-(aminosulfonyl)anilino]-1H-pyrrolo[2,3-b]pyridin-3-yl}-2-phenyl-2-propenamide;
4-({3-[3-amino-3-oxo-2-phenyl-1-propenyl]-1H-pyrrolo[2, 3-b]pyridin-6-yl}amino)benzamide;
3-[6-(3-aminoanilino)-1H-pyrrolo[2,3-b]pyridin-3-yl]-2-propenamide;
2-phenyl-3-[6-(3-pyridinylamino)-1H-pyrrolo[2,3-b] pyridin-3-yl]-2-propenamide;
2-phenyl-3-[6-(1,3-thiazol-2-ylamino)-1H-pyrrolo[2,3-b] pyridin-3-yl]-2-propenamide;
3-[6-(benzylamino)-1H-pyrrolo[2,3-b]pyridin-3-yl]-2-phenyl-2-propenamide;
3-(6-{[4-(aminosulfonyl)benzyl]amino}-1H-pyrrolo[2,3-b] pyridin-3-yl)-2-phenyl-2-propenamide;
3-[6-(acetylamino)-1H-pyrrolo[2,3-b]pyridin-3-yl]-2-phenyl-2-propenamide;
3-{6-[(aminocarbonyl)amino]-1H-pyrrolo[2,3-b]pyridin-3-yl}-2-phenyl-2-propenamide;
3-(6-{[(methylamino)carbonyl]amino}-1H-pyrrolo[2,3-b] pyridin-3-yl)-2-phenyl-2-propenamide;
3-{6-[(anilinocarbonyl)amino]-1H-pyrrolo[2,3-b]pyridin-3-yl}-2-phenyl-2-propenamide;
3-(6-{[(4-bromoanilino)carbonyl]amino}-1H-pyrrolo[2,3-b]pyridin-3-yl)-2-phenyl-2-propenamide;
3-(6-{[(3-hydroxyanilino)carbonyl]amino}-1H-pyrrolo[2,3-b]pyridin-3-yl)-2-phenyl-2-propenamide;
3-(6-{[(benzylamino)carbonyl]amino}-1H-pyrrolo[2,3-b] pyridin-3-yl)-2-phenyl-2-propenamide;
N-{3-[3-amino-3-oxo-2-phenyl-1-propenyl]-1H-pyrrolo[2, 3-b]pyridin-6-yl}-1-piperidinecarboxamide;
N-{3-[3-amino-3-oxo-2-phenyl-1-propenyl]-1H-pyrrolo[2, 3-b]pyridin-6-yl}-4-methyl-1-piperazinecarboxamide;
N-{3-[3-amino-3-oxo-2-phenyl-1-propenyl]-1H-pyrrolo[2, 3-b]pyridin-6-yl}-4-morpholinecarboxamide;
N-{3-[3-amino-3-oxo-2-phenyl-1-propenyl]-1H-pyrrolo[2, 3-b]pyridin-6-yl}-1-pyrrolidinecarboxamide;
ethyl 3-[3-amino-3-oxo-2-phenyl-1-propenyl]-1H-pyrrolo [2,3-b]pyridin-6-ylcarbamate;
tert-butyl 3-[3-amino-3-oxo-2-phenyl-1-propenyl]-1H-pyrrolo[2,3-b]pyridin-6-ylcarbamate;
3-{6-[(methylsulfonyl)amino]-1H-pyrrolo[2,3-b]pyridin-3-yl}-2-phenyl-2-propenamide;
2-phenyl-3-{6-[(phenylsulfonyl)amino]-1H-pyrrolo[2,3-b] pyridin-3-yl}-2-propenamide;
2-phenyl-3-(6-{[(phenylsulfonyl)methyl]amino}-1H-pyrrolo[2,3-b]pyridin-3-yl)-2-propenamide;
3-(6-{[([1,1'-biphenyl]-4-ylmethyl)sulfonyl]amino}-1H-pyrrolo[2,3-b]pyridin-3-yl)-2-phenyl-2-propenamide;
3-{6-[([1,1'-biphenyl]-4-ylsulfonyl)amino]-1H-pyrrolo[2,3-b]pyridin-3-yl}-2-phenyl-2-propenamide;
3-(4-chloro-1H-pyrrolo[2,3-b]pyridin-3-yl)-2-phenyl-2-propenamide
3-(4-anilino-1H-pyrrolo[2,3-b]pyridin-3-yl)-2-phenyl-2-propenamide
3-[4-(4-bromoanilino)-1H-pyrrolo[2,3-b]pyridin-3-yl]-2-phenyl-2-propenamide
3-[4-(3-hydroxyanilino)-1H-pyrrolo[2,3-b]pyridin-3-yl]-2-phenyl-2-propenamide
3-{4-[4-(aminosulfonyl)anilino]-1H-pyrrolo[2,3-b]pyridin-3-yl}-2-phenyl-2-propenamide
4-({3-[3-amino-3-oxo-2-phenyl-1-propenyl]-1H-pyrrolo[2, 3-b]pyridin-4-yl}amino)benzamide
3-[4-(3-aminoanilino)-1H-pyrrolo[2,3-b]pyridin-3-yl]-2-phenyl-2-propenamide
2-phenyl-3-[4-(3-pyridinylamino)-1H-pyrrolo[2,3-b] pyridin-3-yl]-2-propenamide
2-phenyl-3-[4-(1,3-thiazol-2-ylamino)-1H-pyrrolo[2,3-b] pyridin-3-yl]-2-propenamide
3-(4-amino-1H-pyrrolo[2,3-b]pyridin-3-yl)-2-phenyl-2-propenamide 3-[4-(methylamino)-1H-pyrrolo[2,3-b]pyridin-3-yl]-2-phenyl-2-propenamide
3-[4-(cyclohexylamino)-1H-pyrrolo[2,3-b]pyridin-3-yl]-2-phenyl-2-propenamide
3-[4-(benzylamino)-1H-pyrrolo[2,3-b]pyridin-3-yl]-2-phenyl-2-propenamide
3-(4-{[4-(aminosulfonyl)benzyl]amino}-1H-pyrrolo[2,3-b]pyridin-3-yl)-2-phenyl-2-propenamide
3-[4-(acetylamino)-1H-pyrrolo[2,3-b]pyridin-3-yl]-2-phenyl-2-propenamide
3-{4-[(aminocarbonyl)amino]-1H-pyrrolo[2,3-b]pyridin-3-yl}-2-phenyl-2-propenamide
3-(4-{[(methylamino)carbonyl]amino}-1H-pyrrolo[2,3-b]pyridin-3-yl)-2-phenyl-2-propenamide
3-{4-[(anilinocarbonyl)amino]-1H-pyrrolo[2,3-]pyridin-3-yl}-2-phenyl-2-propenamide
3-(4-{[(4-bromoanilino)carbonyl]amino}-1H-pyrrolo[2,3-b]pyridin-3-yl)-2-phenyl-2-propenamide
3-(4-{[(3-hydroxyanilino)carbonyl]amino}-1H-pyrrolo[2,3-b]pyridin-3-yl)-2-phenyl-2-propenamide
3-(4-{[(benzylamino)carbonyl]amino}-1H-pyrrolo[2,3-b]pyridin-3-yl)-2-phenyl-2-propenamide
N-{3-[3-amino-3-oxo-2-phenyl-1-propenyl]-1H-pyrrolo[2,3-b]pyridin-4-yl}-1-piperidinecarboxamide
N-{3-[3-amino-3-oxo-2-phenyl-1-propenyl]-1H-pyrrolo[2,3-b]pyridin-4-yl}-1-pyrrolidinecarboxamide
N-{3-[3-amino-3-oxo-2-phenyl-1-propenyl]-1H-pyrrolo[2,3-b]pyridin-4-yl}-4-methyl-1-piperazinecarboxamide
N-{3-[3-amino-3-oxo-2-phenyl-1-propenyl]-1H-pyrrolo[2,3-b]pyridin-4-yl}-4-morpholinecarboxamide
1-ethyl 3-[3-amino-3-oxo-2-phenyl-1-propenyl]-1H-pyrrolo[2,3-b]pyridin-4-ylcarbamate
1-tert-butyl 3-[3-amino-3-oxo-2-phenyl-1-propenyl]-1H-pyrrolo[2,3-b]pyridin-4-ylcarbamate
3-{4-[(methylsulfonyl)amino]-1H-pyrrolo[2,3-b]pyridin-3-yl}-2-phenyl-2-propenamide
2-phenyl-3-{4-[(phenylsulfonyl)amino]-1H-pyrrolo[2,3-b]pyridin-3-yl}-2-propenamide
3-{4-[(benzylsulfonyl)amino]-1H-pyrrolo[2,3-b]pyridin-3-yl}-2-phenyl-2-propenamide
3-{4-[([1,1'-biphenyl]-4-ylsulfonyl)amino]-1H-pyrrolo[2,3-b]pyridin-3-yl}-2-phenyl-2-propenamide
3-(4-{[([1,1'-biphenyl]-4-ylmethyl)sulfonyl]amino}-1H-pyrrolo[2,3-b]pyridin-3-yl)-2-phenyl-2-propenamide
3-(5-amino-1H-pyrrolo[2,3-b]pyridin-3-yl)-2-phenyl-2-propenamide
3-[5-(methylamino)-1H-pyrrolo[2,3-b]pyridin-3-yl]-2-phenyl-2-propenamide
3-[5-(cyclohexylamino)-1H-pyrrolo[2,3-b]pyridin-3-yl]-2-phenyl-2-propenamide
3-[5-(benzylamino)-1H-pyrrolo[2,3-b]pyridin-3-yl]-2-phenyl-2-propenamide
3-(5-{[4-(aminosulfonyl)benzyl]amino}-1H-pyrrolo[2,3-b]pyridin-3-yl)-2-phenyl-2-propenamide
3-[5-(acetylamino)-1H-pyrrolo[2,3-b]pyridin-3-yl]-2-phenyl-2-propenamide
3-{5-[(aminocarbonyl)amino]-1H-pyrrolo[2,3-b]pyridin-3-yl}-2-phenyl-2-propenamide
3-(5-{[(methylamino)carbonyl]amino}-1H-pyrrolo[2,3-b]pyridin-3-yl)-2-phenyl-2-propenamide
3-{5-[(anilinocarbonyl)amino]-1H-pyrrolo[2,3-b]pyridin-3-yl}-2-phenyl-2-propenamide
3-(5-{[(4-bromoanilino)carbonyl]amino}-1H-pyrrolo[2,3-b]pyridin-3-yl)-2-phenyl-2-propenamide
3-(5-{[(3-hydroxyanilino)carbonyl]amino}-1H-pyrrolo[2,3-b]pyridin-3-yl)-2-phenyl-2-propenamide
3-(5-{[(benzylamino)carbonyl]amino}-1H-pyrrolo[2,3-b]pyridin-3-yl)-2-phenyl-2-propenamide
N-{3-[3-amino-3-oxo-2-phenyl-1-propenyl]-1H-pyrrolo[2,3-b]pyridin-5-yl}-1-piperidinecarboxamide
N-{3-[3-amino-3-oxo-2-phenyl-1-propenyl]-1H-pyrrolo[2,3-b]pyridin-5-yl}-1-pyrrolidinecarboxamide
N-{3-[3-amino-3-oxo-2-phenyl-1-propenyl]-1H-pyrrolo[2,3-b]pyridin-5-yl}-4-methyl-1-piperazinecarboxamide
N-{3-[3-amino-3-oxo-2-phenyl-1-propenyl]-1H-pyrrolo[2,3-b]pyridin-5-yl}-4-morpholinecarboxamide
ethyl 3-[3-amino-3-oxo-2-phenyl-1-propenyl]-1H-pyrrolo[2,3-b]pyridin-5-ylcarbamate
tert-butyl 3-[3-amino-3-oxo-2-phenyl-1-propenyl]-1H-pyrrolo[2,3-b]pyridin-5-ylcarbamate
3-{5-[(methylsulfonyl)amino]-1H-pyrrolo[2,3-b]pyridin-3-yl}-2-phenyl-2-propenamide
2-phenyl-3-{5-[(phenylsulfonyl)amino]-1H-pyrrolo[2,3-b]pyridin-3-yl}-2-propenamide
3-{5-[(benzylsulfonyl)amino]-1H-pyrrolo[2,3-b]pyridin-3-yl}-2-phenyl-2-propenamide
3-{5-[([1,1'-biphenyl]-4-ylsulfonyl)amino]-1H-pyrrolo[2,3-b]pyridin-3-yl}-2-phenyl-2-propenamide
3-(5-{[([1,1'-biphenyl]-4-ylmethyl)sulfonyl]amino}-1H-pyrrolo[2,3-b]pyridin-3-yl)-2-phenyl-2-propenamide
2-(4-chlorophenyl)-3-(1H-pyrrolo[2,3-b]pyridin-3-yl)-2-propenamide
3-(1H-pyrrolo[2,3-b]pyridin-3-yl)-2-(4-tolyl)-2-propenamide
3-(1H-pyrrolo[2,3-b]pyridin-3-yl)-2-[2-(trifluoromethyl)phenyl]-2-propenamide
2-(1-acetyl-1H-indol-3-yl)-3-(1H-pyrrolo[2,3-b]pyridin-3-yl)-2-propenamide
2-(1H-indol-3-yl)-3-(1H-pyrrolo[2,3-b]pyridin-3-yl)-2-propenamide
2-(3-fluoro-4-hydroxyphenyl)-3-(1H-pyrrolo[2,3-b]pyridin-3-yl)-2-propenamide
2-(2,3-dihydro-1H-inden-5-yl)-3-(1H-pyrrolo[2,3-b]pyridin-3-yl)-2-propenamide
2-(3-pyridinyl)-3-(1H-pyrrolo[2,3-b]pyridin-3-yl)-2-propenamide
2-(4-hydroxyphenyl)-3-(1H-pyrrolo[2,3-b]pyridin-3-yl)-2-propenamide
2-(4-methoxyphenyl)-3-(1H-pyrrolo[2,3-b]pyridin-3-yl)-2-propenamide
2-(2-hydroxyphenyl)-3-(1H-pyrrolo[2,3-b]pyridin-3-yl)-2-propenamide
2-(2-methoxyphenyl)-3-(1H-pyrrolo[2,3-b]pyridin-3-yl)-2-propenamide
2-[1,1'-biphenyl]-4-yl-3-(1H-pyrrolo[2,3-b]pyridin-3-yl)-2-propenamide
2-(4-hydroxy-5-isopropyl-2-methylphenyl)-3-(1H-pyrrolo[2,3-b]pyridin-3-yl)-2-propenamide
2-(4-hydroxy-3-methoxyphenyl)-3-(1H-pyrrolo[2,3-b]pyridin-3-yl)-2-propenamide
2-(3-chlorophenyl)-3-(1H-pyrrolo[2,3-b]pyridin-3-yl)-2-propenamide
2-(3-methoxyphenyl)-3-(1H-pyrrolo[2,3-b]pyridin-3-yl)-2-propenamide
2-(3-bromophenyl)-3-(1H-pyrrolo[2,3-b]pyridin-3-yl)-2-propenamide
2-(1,3-benzodioxol-5-yl)-3-(1H-pyrrolo[2,3-b]pyridin-3-yl)-2-propenamide
2-(3,5-dimethoxyphenyl)-3-(1H-pyrrolo[2,3-b]pyridin-3-yl)-2-propenamide
2-(3-fluorophenyl)-3-(1H-pyrrolo[2,3-b]pyridin-3-yl)-2-propenamide
2-(4-butoxyphenyl)-3-(1H-pyrrolo[2,3-b]pyridin-3-yl)-2-propenamide
2-(3-chloro-4-hydroxyphenyl)-3-(1H-pyrrolo[2,3-b]pyridin-3-yl)-2-propenamide 2-[4-(methylsulfonyl)phenyl]-3-(1H-pyrrolo[2,3-b]pyridin-3-yl)-2-propenamide
2-(4-ethoxyphenyl)-3-(1H-pyrrolo[2,3-b]pyridin-3-yl)-2-propenamide
2-(3-methylphenyl)-3-(1H-pyrrolo[2,3-b]pyridin-3-yl)-2-propenamide
2-(2-methylphenyl)-3-(1H-pyrrolo[2,3-b]pyridin-3-yl)-2-propenamide
2-(3,4-dihydroxyphenyl)-3-(1H-pyrrolo[2,3-b]pyridin-3-yl)-2-propenamide
3-(1H-pyrrolo[2,3-b]pyridin-3-yl)-2-(2-thienyl)-2-propenamide
2-(2-bromophenyl)-3-(1H-pyrrolo[2,3-b]pyridin-3-yl)-2-propenamide
2-(2-fluorophenyl)-3-(1H-pyrrolo[2,3-b]pyridin-3-yl)-2-propenamide
2-(2-chlorophenyl)-3-(1H-pyrrolo[2,3-b]pyridin-3-yl)-2-propenamide
2-(2,4-dichlorophenyl)-3-(1H-pyrrolo[2,3-b]pyridin-3-yl)-2-propenamide
2-(2-chloro-6-fluorophenyl)-3-(1H-pyrrolo[2,3-b]pyridin-3-yl)-2-propenamide
2-(2,6-dichlorophenyl)-3-(1H-pyrrolo(2,3-b]pyridin-3-yl)-2-propenamide
2-(2,5-dimethoxyphenyl)-3-(1H-pyrrolo[2,3-b]pyridin-3-yl)-2-propenamide
2-(3,4-dichlorophenyl)-3-(1H-pyrrolo[2,3-b]pyridin-3-yl)-2-propenamide
3-(1H-pyrrolo[2,3-b]pyridin-3-yl)-2-(3,4,5-trimethoxyphenyl)-2-propenamide
3-(1H-pyrrolo[2,3-b]pyridin-3-yl)-2-[3-(trifluoromethyl)phenyl]-2-propenamide
3-(1H-pyrrolo[2,3-b]pyridin-3-yl)-2-[4-(trifluoromethyl)phenyl]-2-propenamide
2-[3,5-bis(trifluoromethyl)phenyl]-3-(1H-pyrrolo[2,3-b]pyridin-3-yl)-2-propenamide
2-(2,4-difluorophenyl)-3-(1H-pyrrolo[2,3-b]pyridin-3-yl)-2-propenamide
2-(2,5-difluorophenyl)-3-(1H-pyrrolo[2,3-b]pyridin-3-yl)-2-propenamide
2-(3,4-difluorophenyl)-3-(1H-pyrrolo[2,3-b]pyridin-3-yl)-2-propenamide
2-(3,5-difluorophenyl)-3-(1H-pyrrolo[2,3-b]pyridin-3-yl)-2-propenamide
2-[4-(benzyloxy)-3-methoxyphenyl]-3-(1H-pyrrolo[2,3-b]pyridin-3-yl)-2-propenamide
3-(1H-pyrrolo[2,3-b]pyridin-3-yl)-2-(3-thienyl)-2-propenamide
2-(5-methoxy-1H-indol-3-yl)-3-(1H-pyrrolo[2,3-b]pyridin-3-yl)-2-propenamide
2-(1-naphthyl)-3-(1H-pyrrolo[2,3-b]pyridin-3-yl)-2-propenamide
2-(3-methyl-1-benzothien-2-yl)-3-(1H-pyrrolo[2,3-b]pyridin-3-yl)-2-propenamide
2-(3,4-dimethoxyphenyl)-3-(1H-pyrrolo[2,3-b]pyridin-3-yl)-2-propenamide
2-(4-bromophenyl)-3-(1H-pyrrolo[2,3-b]pyridin-3-yl)-2-propenamide
2-[4-(acetylamino)phenyl]-3-(1H-pyrrolo[2,3-b]pyridin-3-yl)-2-propenamide
2-[4-amino-phenyl]-3-(1H-pyrrolo[2,3-b]pyridin-3-yl)-2-propenamide
2-(5-bromo-1H-indol-3-yl)-3-(1H-pyrrolo[2,3-b]pyridin-3-yl)-2-propenamide
2-(1-methyl-1H-indol-3-yl)-3-(1H-pyrrolo[2,3-b]pyridin-3-yl)-2-propenamide
2-(4-fluorophenyl)-3-(1H-pyrrolo[2,3-b]pyridin-3-yl)-2-propenamide
2-[2,5-bis(trifluoromethyl)phenyl]-3-(1H-pyrrolo[2,3-b]pyridin-3-yl)-2-propenamide
2-(2,3,5-difluorophenyl)-3-(1H-pyrrolo[2,3-b]pyridin-3-yl)-2-propenamide
2-[5-(benzyloxy)-1H-indol-3-yl]-3-(1H-pyrrolo[2,3-b]pyridin-3-yl)-2-propenamide
2-(2-amino-1,3-thiazol-4-yl)-3-(1H-pyrrolo[2,3-b]pyridin-3-yl)-2-propenamide
2-mesityl-3-(1H-pyrrolo[2,3-b]pyridin-3-yl)-2-propenamide
3-(1H-pyrrolo[2,3-b]pyridin-3-yl)-2-[4-(trifluoromethoxy)phenyl]-2-propenamide
2-(3,5-ditert-butyl-4-hydroxyphenyl)-3-(1H-pyrrolo[2,3-b]pyridin-3-yl)-2-propenamide
2-[4-(2-amino-2-oxoethoxy)phenyl]-3-(1H-pyrrolo[2,3-b]pyridin-3-yl)-2-propenamide
2-{4-[2-oxo-2-(1-pyrrolidinyl)ethoxy]phenyl}-3-(1H-pyrrolo[2,3-b]pyridin-3-yl)-2-propenamide
2-(3-hydroxy-5-methoxy-2-propylphenyl)-3-(1H-pyrrolo[2,3-b]pyridin-3-yl)-2-propenamide
2-(4-phenoxyphenyl)-3-(1H-pyrrolo[2,3-b]pyridin-3-yl)-2-propenamide
2-[2-(4-chlorophenyl)-1,3-thiazol-4-yl]-3-(1H-pyrrolo[2,3-b]pyridin-3-yl)-2-propenamide
2-{3-[(methylsulfonyl)amino]phenyl}-3-(1H-pyrrolo[2,3-b]pyridin-3-yl)-2-propenamide
2-{4-[(methylsulfonyl)amino]phenyl}-3-(1H-pyrrolo[2,3-b]pyridin-3-yl)-2-propenamide
2-[4-(1-pyrrolidinyl)phenyl]-3-(1H-pyrrolo[2,3-b]pyridin-3-yl)-2-propenamide
2-(4-[(2-amino-2-oxoethyl)amino]phenyl}-3-(1H-pyrrolo[2,3-b]pyridin-3-yl)-2-propenamide

EXAMPLE 4

Preparation of N-butyl-3-(1H-pyrrolo[2,3-b]pyridin-3-yl)-2-phenyl-2-propenamide

To a solution of 3-(1H-pyrrolo[2,3-b]pyridin-3-yl)-2-phenyl-2-propenoic acid (100 mg, 0.3784 mmol.) in 2 ml of DMFd were added O-(benzotriazol-1-yl)-N,N,N',N'-tetramethyluronium tetrafluoborate (121.5 mg, 0.3784 mmol.), N-hydroxybenzotriazole (51.1 mg, 0.3784 mmol) and N,N-diisopropylethylamine (129.2 $\mu$l, 0.7568 mmol). After stirring at room temperature for 30 min., 34.5 $\mu$l (0.3784 mmol.) of n-butylamine were added and the obtained solution was stirred at room temperature, for 24 hours. The resulting mixture was concentrated by evaporation of the solvent in vacuo, the residue was diluted with dichloromethane washed with 1 N NaOH, 1 N HCl, brine, dried over sodium sulphate and evaporated. The residual solid was triturated with Et2O to afford 49 mg of the title compound as a white solid (yield 41%) m.p. 177–179° C. (dec.)

$^1$H-NMR (DMSO-$d_6$) δ ppm: 11.85 (s, 1H, NH pyrrole); 8.21 (dd, 1H, pyridine); 7.82 (dd, 1H, pyridine); 7.7 (s, 1H, C$\underline{H}$=C); 7.2–7.5 (m, 5H, ph); 7.08 (dd, 1H, pyridine); 6.35 (d, 1H, pyrrole); 7.05 (s, 1H, CON$\underline{H}$); 3.14 (m, 2H, C$\underline{H}_2$CH$_2$CH$_2$CH$_3$); 1.4 (m, 2H, CH$_2$C$\underline{H}_2$CH$_2$CH$_3$); 1.24 (m, 2H, CH$_2$CH$_2$C$\underline{H}_2$CH$_3$); 0.86 (t, 3H, CH$_2$CH$_2$CH$_2$C$\underline{H}_3$).

(M+H)$^+$=320

Analogously the following compounds can be prepared starting from 3-(1H-pyrrolo[2,3-b]pyridin-3-yl)-2-phenyl-2-propenoic acid and the suitable amine:

N-benzyl-2-phenyl-3-(1H-pyrrolo[2,3-b]pyridin-3-yl)-2-propenamide
N-methyl-2-phenyl-3-(1H-pyrrolo[2,3-b]pyridin-3-yl)-2-propenamide N-(4-methoxyphenyl)-2-phenyl-3-(1H-pyrrolo[2,3-b]pyridin-3-yl)-2-propenamide
1-(4-morpholinyl)-2-phenyl-3-(1H-pyrrolo[2,3-b]pyridin-3-yl)-2-propen-1-one
N-(4-chlorophenyl)-2-phenyl-3-(1H-pyrrolo[2,3-b]pyridin-3-yl)-2-propenamide
N,N-dimethyl-2-phenyl-3-(1H-pyrrolo[2,3-b]pyridin-3-yl)-2-propenamide
N-isopropyl-2-phenyl-3-(1H-pyrrolo[2,3-b]pyridin-3-yl)-2-propenamide
2-phenyl-1-(1-piperidinyl)-3-(1H-pyrrolo[2,3-b]pyridin-3-yl)-2-propen-1-one
N-[(3-aminomethyl)-pyridin]-2-phenyl-3-(1H-pyrrolo[2,3-b]pyridin-3-yl)-2-propenamide
N-benzyl-N-methyl-2-phenyl-3-(1H-pyrrolo[2,3-b]pyridin-3-yl)-2-propenamide
N-(1H-indazol-6-yl)-2-phenyl-3-(1H-pyrrolo[2,3-b]pyridin-3-yl)-2-propenamide
N-(4-methoxybenzyl)-2-phenyl-3-(1H-pyrrolo[2,3-b]pyridin-3-yl)-2-propenamide
N-(4-chlorobenzyl)-2-phenyl-3-(1H-pyrrolo[2,3-b]pyridin-3-yl)-2-propenamide
N-[(1-ethyl-2-pyrrolidinyl)methyl]-2-phenyl-3-(1H-pyrrolo[2,3-b]pyridin-3-yl)-2-propenamide
N-furfuryl-2-phenyl-3-(1H-pyrrolo[2,3-b]pyridin-3-yl)-2-propenamide
N-(4-hydroxypiperidin)-2-phenyl-3-(1H-pyrrolo[2,3-b]pyridin-3-yl)-2-propenamide
N-(3-hydroxypiperidin)-2-phenyl-3-(1H-pyrrolo[2,3-b]pyridin-3-yl)-2-propenamide
N-(3-methoxyphenyl)-2-phenyl-3-(1H-pyrrolo[2,3-b]pyridin-3-yl)-2-propenamide
N,2-diphenyl-3-(1H-pyrrolo[2,3-b]pyridin-3-yl)-2-propenamide
3-[3-(4-methyl-1-piperazinyl)-3-oxo-2-phenyl-1-propenyl]-1H-pyrrolo[2,3-b]pyridine
N-[4-(dimethylamino)phenyl]-2-phenyl-3-(1H-pyrrolo[2,3-b]pyridin-3-yl)-2-propenamide
N-(3-chlorophenyl)-2-phenyl-3-(1H-pyrrolo[2,3-b]pyridin-3-yl)-2-propenamide
N,N-diethyl-2-phenyl-3-(1H-pyrrolo[2,3-b]pyridin-3-yl)-2-propenamide
3-[3-(4-benzyl-1-piperazinyl)-3-oxo-2-phenyl-1-propenyl]-1H-pyrrolo[2,3-b]pyridine
2-[2-phenyl-3-(1H-pyrrolo[2,3-b]pyridin-3-yl)-2-propenoyl]-1,2,3,4-tetrahydroisoquinoline
N-(tert-butoxy)-2-phenyl-3-(1H-pyrrolo[2,3-b]pyridin-3-yl)-2-propenamide
N-hydroxy-2-phenyl-3-(1H-pyrrolo[2,3-b]pyridin-3-yl)-2-propenamide

EXAMPLE 5

3-(6-amino-1H-pyrrolo[2,3-b]pyridin-3-yl)-2-phenyl-2-propenamide 1 g (3.13 mmol) of 3-(6-acetylamino-1H-pyrrolo[2,3-b]pyridin-3-yl)-2-phenyl-2-propenamide was dissolved in 20 ml of methanol and 3.13 ml of sodium hydrate 1 M were added. The solution is maintained at room temperature for 5 hours and then concentrated under vacuum. The residue was redissolved with dichloromethane and washed with water. The organic layer was finally dried over sodium sulfate and evaporated to give 696 mg (80% yield) of the title compound.

EXAMPLE 6

3-(6-[(phenylacetyl)amino]-1H-pyrrolo[2,3-b]pyridin-3-yl}-2-phenyl-2-propenamide 500 mg (3.67 mmol) of phenylacetic acid were dissolved in 20 ml of dichloromethane and 705 mg (3.67 mmol) of N-(3-dimethylaminopropyl)-N'-ethylcarbodiimide hydrochloride were added at 0° C. The mixture is maintained at the same temperature for 30 minutes and then a solution of 680 mg (2.44 mmol) of 3-(6-amino-1H-pyrrolo[2,3-b]pyridin-3-yl)-2-phenyl-propenamide in 10 ml of dichloromethane was added dropwise. After 6 hours at room temperature the mixture was washed with aqueous sodium bicarbonate. The organic layer was dried over sodium sulfate and evaporated. The residue was chromatographed on a silica gel column by using a mixture cyclohexane/ethylacetate 4/1 to give 626 mg (65% yield) of the title compound.

Analogously the following compounds can be prepared starting from 3-(6-amino-1H-pyrrolo[2,3-b]pyridin-3-yl)-2-phenyl-2-propenamide and the suitable carboxylic acid:
N-{3-[3-amino-3-oxo-2-phenyl-1-propenyl]-1H-pyrrolo[2,3-b]pyridin-6-yl}benzamide;
N-{3-[3-amino-3-oxo-2-phenyl-1-propenyl]-1H-pyrrolo[2,3-b]pyridin-6-yl}-4-bromobenzamide;
N-{3-[3-amino-3-oxo-2-phenyl-1-propenyl]-1H-pyrrolo[2,3-b]pyridin-6-yl}-3hydroxybenzamide;
3-amino-N-{3-[3-amino-3-oxo-2-phenyl-1-propenyl]-1H-pyrrolo[2,3-bπpyridin-6-yl}benzamide;
3-[6-(butyrylamino)-1H-pyrrolo[2,3-b]pyridin-3-yl]-2-phenyl-2-propenamide;
2-phenyl-3-{6-[(phenylacetyl)amino]-1H-pyrrolo[2,3-b]pyridin-3-yl}-2-propenamide;
3-(6-{[(3-hydroxyphenyl)acetyl]amino}-1H-pyrrolo[2,3-b]pyridin-3-yl)-2-phenyl-2-propenamide;
3-(6-{[(3-chlorophenyl)acetyl]amino}-1H-pyrrolo[2,3-b]pyridin-3-yl)-2-phenyl-2-propenamide;
3-(6-{[(3-aminophenyl)acetyl]amino}-1H-pyrrolo[2,3-b]pyridin-3-yl)-2-phenyl-2-propenamide;
2-phenyl-3-{6-[(3-pyridinylacetyl)amino]-1H-pyrrolo[2,3-b]pyridin-3-yl}-2-propenamide;
N-{3-[3-amino-3-oxo-2-phenyl-1-propenyl]-1H-pyrrolo[2,3-b]pyridin-6-yl}-1H-indole-3-carboxamide;
3-{6-[(1H-indol-3-ylacetyl)amino]-1H-pyrrolo[2,3-b]pyridin-3-yl}-2-phenyl-2-propenamide;
N-{3-[3-amino-3-oxo-2-phenyl-1-propenyl]-1H-pyrrolo[2,3-b]pyridin-6-yl}-2-thiophenecarboxamide;
N-{3-[3-amino-3-oxo-2-phenyl-1-propenyl]-1H-pyrrolo[2,3-b]pyridin-6-yl}[1,1'-biphenyl]-4-carboxamide;
3-{6-[([1,1'-biphenyl]-4-ylacetyl)amino]-1H-pyrrolo[2,3-b]pyridin-3-yl}-2-phenyl-2-propenamide;
3-{6-[(1,3-oxazol-2-ylacetyl)amino]-1H-pyrrolo[2,3-b]pyridin-3-yl}-2-phenyl-2-propenamide;
2-phenyl-3-{6-[(1,3-thiazol-2-ylacetyl)amino]-1H-pyrrolo[2,3-b]pyridin-3-yl}-2-propenamide;
N-{3-[3-amino-3-oxo-2-phenyl-1-propenyl]-1H-pyrrolo[2,3-b]pyridin-4-yl}benzamide
N-{3-[3-amino-3-oxo-2-phenyl-1-propenyl]-1H-pyrrolo[2,3-b]pyridin-4-yl}-4-bromobenzamide
N-{3-[3-amino-3-oxo-2-phenyl-1-propenyl]-1H-pyrrolo[2,3-b]pyridin-4-yl}-3-hydroxybenzamide
3-amino-N-{3-[3-amino-3-oxo-2-phenyl-1-propenyl]-1H-pyrrolo[2,3-b]pyridin-4-yl}benzamide
3-[4-(butyrylamino)-1H-pyrrolo[2,3-b]pyridin-3-yl]-2-phenyl-2-propenamide
2-phenyl-3-{4-[(phenylacetyl)amino]-1H-pyrrolo[2,3-b]pyridin-3-yl}-2-propenamide
3-(4-{[(3-hydroxyphenyl)acetyl]amino}-1H-pyrrolo[2,3-b]pyridin-3-yl)-2-phenyl-2-propenamide
3-(4-{[(3-chlorophenyl)acetyl]amino}-1H-pyrrolo[2,3-b]pyridin-3-yl)-2-phenyl-2-propenamide
3-(4-{[(3-aminophenyl)acetyl]amino}-1H-pyrrolo[2,3-b]pyridin-3-yl)-2-phenyl-2-propenamide 2-phenyl-3-{4-[(3-pyridinylacetyl)amino]-1H-pyrrolo[2,3-b]pyridin-3-yl}-2-propenamide
N-{3-[3-amino-3-oxo-2-phenyl-1-propenyl]-1H-pyrrolo[2,3-b]pyridin-4-yl}-1H-indole-3-carboxamide
3-{4-[(1H-indol-3-ylacetyl)amino]-1H-pyrrolo[2,3-b]pyridin-3-yl}-2-phenyl-2-propenamide
N-{3-[3-amino-3-oxo-2-phenyl-1-propenyl]-1H-pyrrolo[2,3-b]pyridin-4-yl}-2-thiophenecarboxamide
N-{3-[3-amino-3-oxo-2-phenyl-1-propenyl]-1H-pyrrolo[2,3-b]pyridin-4-yl}[1,11-biphenyl]-4-carboxamide
3-{4-[(1,3-oxazol-2-ylacetyl)amino]-1H-pyrrolo[2,3-b]pyridin-3-yl}-2-phenyl-2-propenamide
2-phenyl-3-{4-[(1,3-thiazol-2-ylacetyl)amino]-1H-pyrrolo[2,3-b]pyridin-3-yl}-2-propenamide
N-{3-[3-amino-3-oxo-2-phenyl-1-propenyl]-1H-pyrrolo[2,3-b]pyridin-5-yl}benzamide
N-{3-[3-amino-3-oxo-2-phenyl-1-propenyl]-1H-pyrrolo[2,3-b]pyridin-5-yl}-4-bromobenzamide
N-{3-[3-amino-3-oxo-2-phenyl-1-propenyl]-1H-pyrrolo[2,3-b]pyridin-5-yl}-3-hydroxybenzamide
3-amino-N-{3-[3-amino-3-oxo-2-phenyl-1-propenyl]-1H-pyrrolo[2,3-b]pyridin-5-yl}benzamide
3-[5-(butyrylamino)-1H-pyrrolo[2,3-b]pyridin-3-yl]-2-phenyl-2-propenamide
2-phenyl-3-{5-[(phenylacetyl)amino]-1H-pyrrolo[2,3-b]pyridin-3-yl}-2-propenamide
3-(5-{[(3-hydroxyphenyl)acetyl]amino}-1H-pyrrolo[2,3-b]pyridin-3-yl)-2-phenyl-2-propenamide
3-(5-{[(3-chlorophenyl)acetyl]amino}-1H-pyrrolo[2,3-b]pyridin-3-yl)-2-phenyl-2-propenamide
3-(5-{[(3-aminophenyl)acetyl]amino}-1H-pyrrolo[2,3-b]pyridin-3-yl)-2-phenyl-2-propenamide
2-phenyl-3-{5-[(3-pyridinylacetyl)amino]-1H-pyrrolo[2,3-b]pyridin-3-yl}-2-propenamide
N-{3-[3-amino-3-oxo-2-phenyl-1-propenyl]-1H-pyrrolo[2,3-b]pyridin-5-yl}-1H-indole-3-carboxamide
3-{5-[(1H-indol-3-ylacetyl)amino]-1H-pyrrolo[2,3-b]pyridin-3-yl}-2-phenyl-2-propenamide
N-{3-[3-amino-3-oxo-2-phenyl-1-propenyl]-1H-pyrrolo[2,3-b]pyridin-5-yl}-2-thiophenecarboxamide
N-{3-[3-amino-3-oxo-2-phenyl-1-propenyl]-1H-pyrrolo[2,3-b]pyridin-5-yl}[1,1'-biphenyl]-4-carboxamide
3-{5-[(1,3-oxazol-2-ylacetyl)amino]-1H-pyrrolo[2,3-b]pyridin-3-yl}-2-phenyl-2-propenamide
2-phenyl-3-{5-[(1,3-thiazol-2-ylacetyl)amino]-1H-pyrrolo[2,3-b]pyridin-3-yl}-2-propenamide
3-{6-[(2-naphthylacetyl)amino]-1H-pyrrolo[2,3-b]pyridin-3-yl}-2-phenyl-2-propenamide
2-(3-chloro-4-hydroxyphenyl)-3-{6-[(2-naphthylacetyl)amino]-1H-pyrrolo[2,3-b]pyridin-3-yl}-2-propenamide
3-{6-[(1-naphthylacetyl)amino]-1H-pyrrolo[2,3-b]pyridin-3-yl}-2-phenyl-2-propenamide
2-(3-chloro-4-hydroxyphenyl)-3-{6-[(1-naphthylacetyl)amino]-1H-pyrrolo[2,3-b]pyridin-3-yl}-2-propenamide
2-phenyl-3-[6-({[4-(2-thienyl)phenyl]acetyl}amino)-1H-pyrrolo[2,3-b]pyridin-3-yl]-2-propenamide
2-(3-chloro-4-hydroxyphenyl)-3-[6-({[4-(2-thienyl)phenyl]acetyl}amino)-1H-pyrrolo[2,3-b]pyridin-3-yl]-2-propenamide
2-phenyl-3-[6-({[4-(3-thienyl)phenyl]acetyl}amino)-1H-pyrrolo[2,3-b]pyridin-3-yl]-2-propenamide
2-(3-chloro-4-hydroxyphenyl)-3-[6-({[4-(3-thienyl)phenyl]acetyl}amino)-1H-pyrrolo[2,3-b]pyridin-3-yl]-2-propenamide
3-(6-{[(3',4'-difluoro[1,1'-biphenyl]-4-yl)acetyl]amino}-1H-pyrrolo[2,3-b]pyridin-3-yl)-2-phenyl-2-propenamide
2-(3-chloro-4-hydroxyphenyl)-3-(6-{[(3',4'-difluoro[1,1'-biphenyl]-4-yl)acetyl]amino}-1H-pyrrolo[2,3-b]pyridin-3-yl)-2-propenamide
3-(6-{[(5'-fluoro-2'-methoxy[1,1'-biphenyl]-4-yl)acetyl]amino}-1H-pyrrolo[2,3-b]pyridin-3-yl)-2-phenyl-2-propenamide
2-(3-chloro-4-hydroxyphenyl)-3-(6-{[(5'-fluoro-2'-methoxy(1,1'-biphenyl]-4-yl)acetyl]amino}-1H-pyrrolo[2,3-b]pyridin-3-yl)-2-propenamide
3-(6-{[(2',5'-difluoro[1,1'-biphenyl]-4-yl)acetyl]amino}-1H-pyrrolo[2,3-b]pyridin-3-yl)-2-phenyl-2-propenamide
2-(3-chloro-4-hydroxyphenyl)-3-(6-{[(2',5'-difluoro[1,1'-biphenyl]-4-yl)acetyl]amino}-1H-pyrrolo[2,3-b]pyridin-3-yl)-2-propenamide
3-(6-{[(3'-ethoxy[1,1'-biphenyl]-4-yl)acetyl]amino}-1H-pyrrolo[2,3-b]pyridin-3-yl)-2-phenyl-2-propenamide
2-(3-chloro-4-hydroxyphenyl)-3-(6-{[(3'-ethoxy[1,1'-biphenyl]-4-yl)acetyl]amino}-1H-pyrrolo[2,3-b]pyridin-3-yl)-2-propenamide.

All compounds were characterized by mass spectrometry (MS). LC-MS confirmed that in each case the principle component had a molecular ion corresponding to the expected product.

The compounds showed an HPLC area % ranging from 78 to 100.

HPLC analysis: Solvent A: H2O/CH3CN=90/10+0.1% TFA Solvent B: H2O/CH3CN=10/90+0.075% TFA

| Time (min) | % A | % B |
| --- | --- | --- |
| 0 | 0 | 100 |
| 6.5 | 0 | 100 |
| 7 | 100 | 0 |
| 10 | 100 | 0 |

Rate: 1.5 ml/min
Detection: UV 254 nm
Temperature: room temperature
Column: Supelco™, Discovery RP Amide C16, 5□m, (50×4.6)mm

What is claimed is:

1. A process for preparing a compound of formula (II):

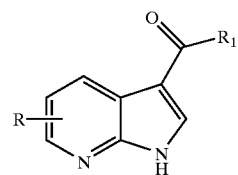

(II)

wherein
R is:
  a halogen atom or
  selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$,
  wherein n is either 0 or 1, and wherein
    R$_4$ and R$_5$ are, independently from each other, hydrogen or an optionally substituted group selected from alkyl, alkenyl, alkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, aryl, arylalkyl, arylalkenyl, arylalkynyl or, taken together to the nitrogen atom to which they are bonded, form an optionally substituted heterocyclyl group; and wherein $R_1$ is optionally substituted alkyl, comprising: reacting a compound of formula (VII):

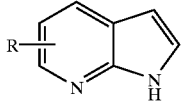

(VII)

with
a) methylmagnesium iodide, thus obtaining a compound of formula (VIII):

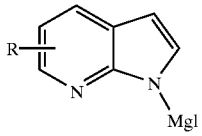

(VIII)

and
b) reacting the compound of formula (VIII) with a compound of formula (IX):

(IX)

wherein $R_1$ is an optionally substituted alkyl group, thus obtaining a compound of formula (X):

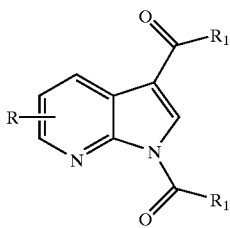

(X)

wherein R and $R_1$ are as defined above; and
c) hydrolyzing the compound of formula (X) in the presence of a base.

2. A compound of formula (II):

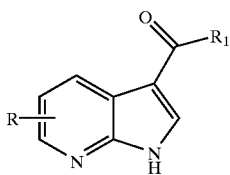

(II)

wherein
R is:
a halogen atom or
is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$, wherein n is either 0 or 1, and wherein
$R_4$ and $R_5$ are, independently from each other, hydrogen or an optionally substituted group selected from alkyl, alkenyl, alkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, aryl, arylalkyl, arylalkenyl, arylalkynyl or, taken together to the nitrogen atom to which they are bonded, form an optionally substituted heterocyclyl group; and $R_1$ is hydrogen or an optionally substituted alkyl group, provided that when $R_1$ is hydrogen, then R is not hydroxy, amino or ureido and provided that when $R_1$ is chloromethyl or dimethylaminomethyl, then R is not a chlorine atom at position 6.

3. The compound of claim 2, wherein R is a halogen atom.

4. The compound of claim 2, wherein R is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$; and
n=1.

5. The compound of claim 2, wherein R is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$; and
n=0.

6. The compound of claim 2, wherein R is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$; and $R_4$ and $R_5$ are, independently from each other, an optionally substituted group selected from alkyl, alkenyl, alkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, aryl, arylalkyl, arylalkenyl, arylalkynyl or, taken together to the nitrogen atom to which they are bonded, form an optionally substituted heterocyclyl group.

7. The compound of claim 2, wherein $R_1$ is alkyl.

8. The compound of claim 2, wherein $R_2$ is a substituted alkyl group.

9. The compound of claim 2, wherein $R_1$ is hydrogen.

10. A compound of formula (II):

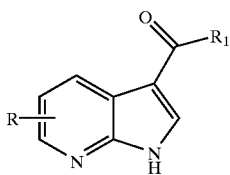

(II)

wherein
R is:
a halogen atom or
is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$, wherein n is either 0 or 1, and wherein
$R_4$ and $R_5$ are, independently from each other, hydrogen or an optionally substituted group selected from alkyl, alkenyl, alkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, aryl, arylalkyl, arylalkenyl, arylalkynyl or, taken together to the nitrogen atom to which they are bonded, form an optionally substituted heterocyclyl group; and $R_1$ is an optionally substituted alkyl group, with the proviso that when R is chlorine at position 6, then $R_1$ is not methyl substituted with chlorine or methyl substituted with dimethylamino.

11. The compound of claim 10, wherein R is a halogen atom.

12. The compound of claim 10, wherein R is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$; and n=1.

13. The compound of claim 10, wherein R is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$; and n=0.

14. The compound of claim 10, wherein R is selected from the group consisting of —CN, —OH, —OCOR$_4$, —(CH$_2$)$_n$NH$_2$, —(CH$_2$)$_n$NHR$_4$, —(CH$_2$)$_n$NHCOR$_4$, —(CH$_2$)$_n$NHCONR$_4$R$_5$, —(CH$_2$)$_n$NHCOOR$_4$, and —(CH$_2$)$_n$NHSO$_2$R$_4$; and $R_4$ and $R_5$ are, independently from each other, an optionally substituted group selected from alkyl, alkenyl, alkynyl, cycloalkyl, cycloalkylalkyl, cycloalkylalkenyl, cycloalkylalkynyl, heterocyclyl, heterocyclylalkyl, heterocyclylalkenyl, heterocyclylalkynyl, aryl, arylalkyl, arylalkenyl, arylalkynyl or, taken together to the nitrogen atom to which they are bonded, form an optionally substituted heterocyclyl group.

15. The compound of claim 14, wherein R is —CN, —OCOR$_4$, (CH$_2$)$_n$NHCOR$_4$, —(CH$_2$)$_n$NHCONR$_4$R$_5$, —(CH$_2$)$_n$NHCOOR$_4$, or —(CH$_2$)$_n$NHSO$_2$R$_4$.

16. The compound of claim 10, wherein $R_1$ is alkyl.

17. The compound of claim 10, wherein $R_1$ is substituted alkyl.

18. A process for preparing a compound of formula (II) as defined in claim 2, wherein $R_1$ is hydrogen, comprising:

reacting a compound of formula (VII):

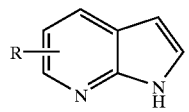

(VII)

with a suitable formylating agent, wherein R is as defined in claim 2.

19. The process of claim 18, wherein said formylating agent is hexmethylenetetramine.

* * * * *